(12) United States Patent
North

(10) Patent No.: US 9,273,024 B2
(45) Date of Patent: Mar. 1, 2016

(54) SYNTHESIS OF CYCLIC CARBONATES

(71) Applicant: UNIVERSITY OF NEW CASTLE UPON TYNE, Newcastle Upon Tyne (GB)

(72) Inventor: Michael North, Newcastle Upon Tyne (GB)

(73) Assignee: University of York, York (GB)

( * ) Notice: Subject to any disclaimer, the term of this patent is extended or adjusted under 35 U.S.C. 154(b) by 0 days.

(21) Appl. No.: 13/887,787

(22) Filed: May 6, 2013

(65) Prior Publication Data

US 2013/0317237 A1 Nov. 28, 2013

Related U.S. Application Data

(63) Continuation of application No. 12/921,264, filed as application No. PCT/GB2009/000624 on Mar. 6, 2009, now abandoned.

(30) Foreign Application Priority Data

Mar. 7, 2008 (GB) .................................. 0804345.7
Nov. 18, 2008 (GB) .................................. 0821092.4

(51) Int. Cl.
C07D 317/38 (2006.01)
C07F 5/06 (2006.01)
C07D 317/34 (2006.01)
C07D 317/36 (2006.01)

(52) U.S. Cl.
CPC ............ *C07D 317/38* (2013.01); *C07D 317/34* (2013.01); *C07D 317/36* (2013.01); *C07F 5/069* (2013.01); *C07B 2200/11* (2013.01)

(58) Field of Classification Search
CPC ..................................................... C07D 317/38
See application file for complete search history.

(56) References Cited

U.S. PATENT DOCUMENTS

| 2,773,070 | A | * | 12/1956 | Lichtenwalter et al. | ...... 549/230 |
| 6,521,561 | B1 | | 2/2003 | Jacobsen et al. | |
| 2008/0214386 | A1 | | 9/2008 | Takahashi et al. | |
| 2013/0317237 | A1 | | 11/2013 | North | |

FOREIGN PATENT DOCUMENTS

| CN | 1789258 | | 6/2006 |
| CN | 1796384 | A | 7/2006 |
| CN | 101020747 | A * | 8/2007 |
| EP | 1 970 199 | A1 | 9/2008 |
| GB | 2008 132474 | A1 | 4/2008 |
| JP | 58222079 | A | 12/1983 |
| JP | 02047134 | A | 2/1990 |
| JP | 2005-202022 | A | 8/1993 |
| JP | 2001 003043 | A | 1/2001 |
| JP | 2001-129397 | | 5/2001 |
| JP | 2005-254068 | A | 9/2005 |
| SK | 0284530 | B6 | 6/2005 |
| WO | 03 29325 | A1 | 4/2003 |
| WO | 2005 084801 | A1 | 9/2005 |
| WO | 2006 032716 | A1 | 3/2006 |
| WO | WO2008/132474 | | 11/2008 |

OTHER PUBLICATIONS

Green, Malcolm, "Converting CO2 into Chemicals", RSC Environment, Sustainability and Energy Forum, Oxford University, Jul. 2006.
Hu, Shaojing, et al., "An Efficient Synthesis of (+)-exo-Brevicomin via Chloroallylboration", J. Org. Chem. 1999, 64, 2524-2526.
Huang, Jin-Wen, et al., "Chemical Fixation of Carbon Dioxide by NaI/PPh3/PhOH", J. Org. Chem. 2003, 68, 6705-6709.
Jiang, Jia-Li, et al., "Re(CO)5Br-Catalyzed Coupling of Epoxides with CO2 Affording Cyclic Carbonates under Solvent-Free Conditions", J. Org. Chem. 2005, 70, 381-383.
Kim, Yong Jin, et al., "Tetrahaloindate(III)-Based Ionic Liquids in the Coupling Reaction of Carbon Dioxide and Epoxides to Generate Cyclic Carbonates: H-Bonding and Mechanistic Studies", J. Org. Chem. 2005, 70, 7882-7891.

(Continued)

Primary Examiner — David K O Dell
(74) Attorney, Agent, or Firm — Steptoe & Johnson LLP

(57) ABSTRACT

A dimeric aluminum(salen) catalyst of formula I:

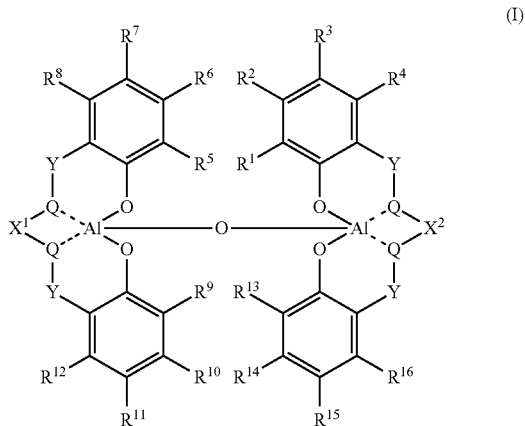

wherein: (a) at least one R group is selected from L-A, and/or (b) at least one of X group is a divalent C3-7 heterocyclene group, containing a ring atom which is a quaternary nitrogen atom paired with a counterion selected from Cl, Br and I; and/or (c) at least one X group is a C2-5 alkylene chain or a C1-3 bisoxyalkylene chain, substituted by a group -Q-L-A; and/or
(ii) (a) one R group is L-A', or (b) one X group is a divalent C3-7 heterocyclene group, containing a ring atom which is a quaternary nitrogen forming part of an ammonium linking group bound to a solid support and paired with a counterion selected from Cl, Br and I; or (c) one X group is a C2-5 alkylene chain or a C1-3 bisoxyalkylene chain, substituted by a group -Q-L-A'.

15 Claims, 1 Drawing Sheet

(56) References Cited

OTHER PUBLICATIONS

Sit, Wing Nga, et al., "Coupling Reactions of CO2 with Neat Epoxides Catalyzed by PPN Salts to Yield Cyclic Carbonates", J. Org. Chem. 2005, 70, 8583-8586.

Lu, Xiao-Bing, et al., "Aluminum phthalocyanine complex covalently bonded to MCM-41 silica as heterogeneous catalyst for the synthesis of cyclic carbonates", Journal of Molecular Catalysis A: Chemical 186 (2002) 33-42.

Doskocil, Eric J., et al., "UV-Vis Spectroscopy of Iodine Adsorbed on Alkali-Metal-Modified Zeolite Catalysts for Addition of Carbon Dioxide to Ethylene Oxide", J. Phys. Chem. B 1999, 103, 6277-6282.

Peng, Jiajian, et al., "Cycloaddition of carbon dioxide to propylene oxide catalyzed by ionic liquids", New J. Chem., 2001, 25, 639-641.

Xie, Haibo, et al., "The effective synthesis of propylene carbonate catalyzed by silica-supported hexaalkylguanidinium chloride", New J. Chem., 2005, 29, 1199-1203.

Calo, Vincenzo, et al., "Cyclic Carbonate Formation from Carbon Dioxide and Oxiranes in Tetrabutylammonium Halides as Solvents and Catalysts", American Chemical Society, Published on Web Jun. 29, 2002.

Berkessel, Albrecht, et al., "Catalytic Asymmetric Addition of Carbon Dioxide to Propylene Oxide with Unprecedented Enantioselectivity", American Chemical Society, Published on Web Aug. 26, 2006.

Zhao, Tiansheng, et al., "Cycloaddition between propylene oxide and CO2 over metal oxide supported KI", Phys. Chem. Chem. Phys., 1999, 1, 3047-3051.

Kasuga, Kuninobu, et al, "Cycloaddition of Carbon Dioxide to Propylene Oxide Catalysed by Tetra-t-Butylphthalocyaninatoaluminium(III) Chloride", Polyhedron vol. 15, No. 1, pp. 69-72, 1996.

Sakharov, A.M., et al., "Copolymerization of propylene oxide with carbon dioxide catalyzed by zinc adipate", Russian Chemical Bulletin, International Edition, vol. 51, No. 8, pp. 1451-1454, Aug. 2002.

Lermontov, S.A., et al., "8-Hydroxyquinolates of trivalent metals as new catalysts for the reaction of CO2 with epoxides", Russian Chemical Bulletin, International Edition, vol. 51, No. 5, pp. 836-838, May 2002.

Rybina, G.V., et al., "Synthesis of Cyclic Organic Carbonates from C3C16 Epoxides", Russian Journal of Applied Chemistry, vol. 76, No. 5, 2003, pp. 842-843. Translated from Zhurnal Prikladnoi Khimii, vol. 76, No. 5, 2003, pp. 870-871.

Lermontov, S.A., et al., "Aluminum 8-Hydroxyquinolate, A New Catalyst for CO2 Reactions with Epoxides", Russian Journal of General Chemistry, vol. 72, No. 9, 2002, pp. 1492-1493. Translated from Zhurnal Obshchei Khimii, vol. 72, No. 9, 2002, pp. 1581-1582.

Zaitseva, V.V., et al., "Synthesis and Structure of 8-Methyl-2-methylene-1,4,6,9-tetraoxaspiro[4.4]nonane", Russian Journal of Organic Chemistry, vol. 38, No. 4, 2002, pp. 588-590. Translated from Zhurnal Organicheskoi Khimii, vol. 38, No. 4, 2002, pp. 614-616.

Jiang, Jia-Li, et al., "Efficient DMF-Catalyzed Coupling of Epoxides with CO2 under Solvent-Free Conditions to Afford Cyclic Carbonates", Synthetic Communicationsw, 36: 3141-3148, 2006.

Tascedda, Patricia, et al., "Electrosynthesis of Benzolactones by Nickel-Catalyzed Carboxylation of Epoxide-Functionalized Aromatic Halides", Synlett 2000, No. 2, 245-247 ISSN 0936-5214.

Qi, Charorong, et al., "Naturally Occurring a-Amino Acid Catalyzed Coupling of Carbon Dioxide with Epoxides to Afford Cyclic Carbonates", SYNLETT 2007, No. 2, pp. 0255-025801.02.207, Advanced online publication: Jan. 24, 2007.

Ochiai, Bungo, et al., "Kinetic and computational studies on aminolysis of bicyclic carbonates bearing alicyclic structure giving alicyclic hydroxyurethanes", Science Direct, Tetrahedron 61 (2005) 1835-1838.

Rodriguez, A., et al., "Total synthesis of lipoxin A4 and lipoxin B4 from butadiene", Tetrahedron Letters 41 (2000) 823-826.

Barbarini, Alessandro, et al., "Cycloaddition of CO2 to epoxides over both homogeneous and silica-supported guanidine catalysts", Tetrahedron Letters 44 (2003) 2931-2934.

Paddock, Robert L., et al., "Co(III) porphyrin/DMAP: an efficient catalyst system for the synthesis of cyclic carbonates from CO2 and epoxides", Science Direct, Tetrahedron Letters 45 (2004) 2023-2026.

Li, Fuwei, et al., "Chemical fixation of CO2 with highly efficient ZnC12/[BMIm]Br catalyst system", Science Direct, Tetrahedron Letters 45 (2004) 8307-8310.

Du, Ya, et al., "A poly(ethylene glycol)-supported quaternary ammonium salt for highly efficient and environmentally friendly chemical fixation of CO2 with epoxides under supercritical conditions", Science Direct, Tetrahedron Letters 47 (2006) 1271-1275.

Chen, Shu-Wei, et al., "Efficient catalytic synthesis of optically active cyclic carbonates via coupling reaction of epoxides and carbon dioxide", Science Direct, Tetrahedron Letters 48 (2007) 297-300.

Lu, Xiao-Bing, et al., "Catalytic formation of ethylene carbonate from supercritical carbon dioxide/ethylene oxide mixture with tetradentate Schiff-base complexes as catalyst", Applied Catalysis A: General 234 (2002) 25-33.

Lu, Xiao-Bing, et al., "Chemical fixation of CO2 to ethylene carbonate under supercritical conditions: continuous and selective", Applied Catalysis A: General 275 (2004) 73-78.

Paddock, Robert L., et al., "Chiral (salen)CoIII catalyst for the synthesis of cyclic carbonates", Chem. Commun., 2004, 1622-1623.

Jing, Huanwang, et al., "(Salen)Tin Complexes: Syntheses, Characterization, Crystal Structures, and Catalytic Activity in the Formation of Propylene Carbonate from CO2 and Propylene Oxide", Inorg. Chem. 2004, 43, 4315-4327.

Chen, Peter, et al., "Binding of Propylene Oxide to Porphyrin- and Salen-M(III) Cations, Where M ) Al, Ga, Cr, and Co", Inorg. Chem. 2005, 44, 2588-2595.

Darensbourg, Donald J., et al., "Comparative Kinetic Studies of the Copolymerization of Cyclohexene Oxide and Propylene Oxide with Carbon Dioxide in the Presence of Chromium Salen Derivatives. In Situ FTIR Measurements of Copolymer vs Cyclic Carbonate Production", JACS Articles, Published on Web Jun. 3, 2003, J. Am. Chem. Soc. 2003, 125, 7586-7591.

Lu, Xiao-Bing, et al., "Asymmetric Catalysis with CO2: Direct Synthesis of Optically Active Propylene Carbonate from Racemic Epoxides", JACS Communications, Published on Web Mar. 5, 2004, J. Am. Chem. Soc. 2004, 126, 3732-3733.

Lu, Xiao-Bing, et al., "Highly active electrophile-nucleophile catalyst system for the cycloaddition of CO2 to epoxides at ambient temperature", Science Direct, Journal of Catalysis 227 (2004) 537-541.

Alvaro, Mercedes, et al., "CO2 fixation using recoverable chromium salen catalysts: use of ionic liquids as cosolvent or high-surface-area silicates as supports", Science Direct, Journal of Catalysis 228 (2004) 254-258.

Lu, Xiao-Bing, et al., "Synthesis of ethylene carbonate from supercritical carbon dioxide/ethylene oxide mixture in the presence of bifunctional catalyst", Journal of Molecular Catalysis A: Chemical 186 (2002) 1-11.

Lu, Xiao-Bing, et al., "Chemical fixation of carbon dioxide to cyclic carbonates under extremely mild conditions with highly active bifunctional catalysts", Science Direct, Journal of Molecular Catalysis A: Chemical 210 (2004) 31-34.

Alvaro, Mercedes, et al., "Polymer-bound aluminium salen complex as reusable catalysts for CO2 insertion into epoxides", Science Direct, Tetrahedron 61 (2005) 12131-12139.

Kroger, Mario, et al., "Alternating Copolymerization of Carbon Dioxide and Cyclohexene Oxide and Their Terpolymerization with Lactide Catalyzed by Zinc Complexes of N,N Ligands", Adv. Synth. Catal. 2006, 348, 1908-1918.

Lu, Xiao-Bing, et al., "Highly Active, Binary Catalyst Systems for the Alternating Copolymerization of CO2 and Epoxides under Mild Conditions", Angew. Chem. Int. Ed. 2004, 43, 3574-3577.

Darensbourg, Donald J., et al., "Probing the mechanistic aspects of the chromium salen catalyzed carbon dioxide/epoxide copolymerization process using in situ ATR/FTIR", Science Direct, Catalysis Today 98 (2004) 485-492.

(56) References Cited

OTHER PUBLICATIONS

Stamp, Louise M., et al., "Polymer supported chromium porphyrin as catalyst for polycarbonate formation in supercritical carbon dioxide", Chem. Commun., 2001, 2502-2503.
Darensbourg, Donald J., et al., "Solid-State Structures of Zinc(II) Benzoate Complexes. Catalyst Precursors for the Coupling of Carbon Dioxide and Epoxides", Inorg. Chem. 2002, 41, 973-980.
Taylor, Mark S., et al., "Highly Enantioselective Conjugate Additions to r,â-Unsaturated Ketones Catalyzed by a (Salen)Al Complex", JACS Articles, Published on Web Jan. 6, 2005.
Maggi, Raimondo, et al., "Synthesis of oxazolidinones in supercritical CO2 under heterogeneous catalysis", Science Direct, Tetrahedron Letters 48 (2007) 2131-2134.
Saito, Mashairo, et al., "Advances in joint research between NIRE and RITE for developing a novel technology for methanol synthesis from CO2 and H2", Applied Organometallic Chemistry Appl. Organometal. Chem. 14, 763-772 (2000).
Nam, Sang-Sung, et al., "Effect of lanthanum loading in Fe±K/La±Al2O3 catalysts for CO2 hydrogenation to hydrocarbons", Applied Organometallic Chemistry Appl. Organometal. Chem. 14, 794-798 (2000).
Ushikoshi, Kenji, et al., "Methanol synthesis from CO2 and H2 in a bench-scale test plant", Applied Organometallic Chemistry Appl. Organometal. Chem. 14, 819-825 (2000).
Ando, Hisanori, et al., "Active phase of iron catalyst for alcohol formation in hydrogenation of carbon oxides", Applied Organometallic Chemistry Appl. Organometal. Chem. 14, 831-835 (2000).
Kusama, Hitoshi, et al., "Alcohol synthesis by catalytic hydrogenation of CO2 over Rh±Co/SiO2", Applied Organometallic Chemistry Appl. Organometal. Chem. 14, 836-840 (2000).
Joo, Ferenc, et al., "NOTE Homogeneous hydrogenation of aqueous hydrogen carbonate to formate under mild conditions with water soluble rhodium(I)± and ruthenium(II)±phosphine catalysts", Applied Organometallic Chemistry Appl. Organometal. Chem. 14, 857-859 (2000).
Kim, Hoon Sik, et al., Isolation of a Pyridinium Alkoxy Ion Bridged Dimeric Zinc complex for the Coupling Reactions of CO2 and Epoxides, Angew. Chem. Int. Ed. 2000, 39, No. 22.
Aresta, Michele, et al., "Direct synthesis of organic carbonates by oxidative carboxylation of ole®ns catalyzed by metal oxides: developing green chemistry based on carbon dioxide", Applied Organometallic Chemistry Appl. Organometal. Chem. 14, 799-802 (2000).
Sun, Jianmin, et al., "Direct oxidative carboxylation of styrene to styrene carbonate in the presence of ionic liquids", Science Direct, Catalysis Communications 5 (2004) 83-87.
Vieville, C., et al., "Synthesis of glycerol carbonate by direct carbonatation of glycerol in supercritical CO2 in the presence of zeolites and ion exchange resins", Catalysis Letters 56 (1998) 245-247.
Srivastava, R., et al., "Synthesis of polycarbonate precursors over titanosilicate molecular sieves", Catalysis Letters vol. 91, Nos. 1-2, Nov. 2003 (# 2003).
Sun, Jianmin, et al., "One-pot synthesis of styrene carbonate from styrene in tetrabutylammonium bromide", Science Direct, Catalysis Today 93-95 (2004) 383-388.
Dibenedetto, Angela, et al., "Synthesis of cyclic carbonates from epoxides: Use of reticular oxygen of Al2O3 or Al2O3-supported CeOx for the selective epoxidation of propene", Science Direct, Catalysis Today 115 (2006) 117-123.
Kisch, Horst, et al., "Bifunktionelle Katalysatoren zur Synthese cyclischer Carbonate aus Oxiranen and Kohlendioxid", Chem. Ber. 119. 1095-1100 (1986).
Tominaga, Ken-Ichi, et al., "Ethylene Oxide-mediated Reduction of C02 to CO and Ethylene Glycol catalysed by Ruthenium Complexes", J. Chem. Soc., Chem. Commun., 1995.
Tascedda, Patricia, et al., "Novel Electrochemical Reactivity of Ni(cyclam)Br2: Catalytic Carbon Dioxide Incorporation into Epoxides", J. Chem. Soc., Chem. Commun., 1995.
Yano, Takashi, et al., "Magnesium oxide-catalysed reaction of carbon dioxide with an epoxide with retention of stereochemistry", pp. 1129-1130, Chem. Commun., 1997.
Kawanami, Hajime, et al., "Chemical fixation of carbon dioxide to styrene carbonate under supercritical conditions with DMF in the absence of any additional catalysts", Chem. Commun., 2000, 2089-2090.
Yang, Hongzhou, et al., "Electrochemical activation of carbon dioxide in ionic liquid: synthesis of cyclic carbonates at mild reaction conditions", Chem. Commun., 2002, 274-275.
Kawanami, Hajime, et al., "A rapid and effective synthesis of propylene carbonate using a supercritical CO2—ionic liquid system", Chem. Commun., 2003, 896-897.
Mori, Kohsuke, et al., "A single-site hydroxyapatite-bound zinc catalyst for highly efficient chemical fixation of carbon dioxide with epoxides", Chem. Commun., 2005, 3331-3333.
Takahashi, Toshikazu, et al., "Synergistic hybrid catalyst for cyclic carbonate synthesis: Remarkable acceleration caused by immobilization of homogeneous catalyst on silica", Chem. Commun., 2006, 1664-1666.
Kim, Hoon Sik, et al., "New Mechanistic Insight into the Coupling Reactions of CO2 and Epoxides in the Presence of Zinc Complexes", Chem. Eur. J. 2003, 9, No. 3.
Man, Lok Man, et al., "Synthesis of Heterobimetallic RuMn Complexes and the Coupling Reactions of Epoxides with Carbon Dioxide Catalyzed by these Complexes", Chem. Eur. J. 2006, 12, 1004-1015.
Aresta, Michele, et al., "Unique Evidence for a RhIII to RhI Reduction by Deoxygenation of a Carbonate Moiety to CO2 by an Out-of-Sphere Phosphane", Eur. J. Inorg. Chem. 2001, 180121806.
Solladie-Cavallo, Arlette, et al., "A Mild Stereo- and Enantiospecific Conversion of 2,3-Diaryl-Substituted Oxiranes into 2,2-Dimethyl-1,3-Dioxolanes by an Acetone/Amberlyst 15 System", Eur. J. Org. Chem. 2006, 3007-3011.
Sako, Takeshi, et al., "Cycloaddition of Oxirane Group with Carbon Dioxide in the Supercritical Homogeneous State", Ind. Eng. Chem. Res. 2002, 41, 5353-5358.
Aida, Takuzo, et al., "Activation of Carbon Dioxide with Aluminum Porphyrin and Reaction with Epoxide. Studies on (Tetraphenylporphinato)aluminum Alkoxide Having a Long Oxyalkylene Chain as the Alkoxide Group", J. Am. Chem. Soc. 1983, 105, 1304-1309.
Trost, Barry M., et al., Palladium-Mediated Vicinal Cleavage of Allyl Epoxides with Retention of Stereochemistry: A Cis Hydroxylation Equivalent, J. Am. Chem. SOC. 1985, 107, 6123-6124.
Myers, Andrew G., "Stereochemical Assignment of Neocarzinostatin Chromophore. Structures of Neocarzinostatin Chromophore-Methyl Thioglycolate Adductst", J. Am. Chem. SOC. 1988, 110, 7212-7214.
Sugimoto, Hiroshi, et al., "Photoresponsive Molecular Switch to Control Chemical Fixation of CO2", J. Am. Chem. Soc. 1999, 121, 2325-2326.
Yamaguchi, Kazuya, et al., "Mg—Al Mixed Oxides as Highly Active Acid-Base Catalysts for Cycloaddition of Carbon Dioxide to Epoxides", J. Am. Chem. Soc. 1999, 121, 4526-4527.
Paddock, Robert L., et al., "Chemical CO2 Fixation: Cr(III) Salen Complexes as Highly Efficient Catalysts for the Coupling of CO2 and Epoxides", J. Am. Chem. Soc. 2001, 123, 11498-11499.
Shi, Feng, et al., "From CO Oxidation to CO2 Activation: An Unexpected Catalytic Activity of Polymer-Supported Nanogold", JACS Communications, Published on Web Mar. 4, 2005.
Doll, Kenneth M., et al., "Synthesis of Carbonated Fatty Methyl Esters Using Supercritical Carbon Dioxide", J. Agric. Food Chem. 2005, 53, 9608-9614.
Tu, Mai, et al., "Cycloaddition of CO2 to Epoxides over Solid Base Catalysts", Journal of Catalysis 199, 85-91 (2001).
Kim, Hoon Sik, et al., "Well-Defined Highly Active Heterogeneous Catalyst System for the Coupling Reactions of Carbon Dioxide and Epoxides", Journal of Catalysis 205, 226-229 (2002).
Yasuda, Hiroyuki, et al., "Cyclic Carbonate Synthesis from Supercritical Carbon Dioxide and Epoxide over Lanthanide Oxychloride", Journal of Catalysis 209, 547-550 (2002).

(56) References Cited

OTHER PUBLICATIONS

Sun, Jianmin, et al., "A direct synthesis of styrene carbonate from styrene with the Au/SiO2—ZnBr2/Bu4NBr catalyst system", Science Direct, Journal of Catalysis 230 (2005) 398-405.

Yasuda, Hiroyuki, et al., "Efficient synthesis of cyclic carbonate from carbon dioxide catalyzed by polyoxometalate: the remarkable effects of metal substitution", Science Direct, Journal of Catalysis 233 (2005) 119-122.

Srivastava, R., et al., "CO2 activation and synthesis of cyclic carbonates and alkyl/aryl carbamates over adenine-modified Ti-SBA-15 solid catalysts", Science Direct, Journal of Catalysis 233 (2005) 1-15.

Aresta, Michele, et al., "Carbon dioxide as building block for the synthesis of organic carbonates Behavior of homogeneous and heterogeneous catalysts in the oxidative carboxylation of olefins", Journal of Molecular Catalysis A: Chemical 182-183 (2002) 399-409.

Nomura, Ryoki, et al., "Synthesis of Cyclic Carbonates from Carbon Dioxide and Epoxides in the Presence of Organoantimony Compounds as Novel Catalysts", J. Org. Chsm. 1980,45, 3735-3738.

Kihara, Nobuhiro, et al., "Catalytic Activity of Various Salts in the Reaction of 2,3-Epoxypropyl Phenyl Ether and Carbon Dioxide under Atmospheric Pressure", J . Org. Chem. 1993,58, 6198-6202.

Kihara, Nobuhiro, et al., "Preparation of 1,3-Oxathiolane-2-thionebsy the Reaction of Oxirane and Carbon Disulfide", J. Org. Chem. 1996,60, 473-475.

Kruper, William J., et al., "Catalytic Formation of Cyclic Carbonates from Epoxides and C02 with Chromium Metalloporphyrinates", J. Org. Chem. 1996,60, 725-727.

Melèndez, Jaisiel, et al: "Synthesis of cyclic carbonates from atmospheric pressure carbon dioxide using exceptionally active aluminum (salen) complexes as catalysts" European Journal of Inorganic Chemistry, vol. 2007, No. 21, 2007, pp. 3323-3326, XP00252661, Wiley-VCH Verlag GmbH & Co., KGaA, Weinheim.

Zhang, Xiang, et al.: "Intramolecularly two-centered cooperation catalysis for the synthesis of cyclic carbonates from CO2 and epoxides" Tetrahedron Letters, No. 49 (2008) pp. 6589-6592, Elsevier Ltd.

Sujith S., et al.: "A highly active and recyclable catalytic system for CO2/Propylene Oxide Copolymerization" Agnew Chem. Int. Ed., 2008, vol. 47, pp. 7306-7309, Wiley-VCH Verlag GmbH & Co., KGaA, Weinheim.

Broadwith: "Waste CO2 turned into useful molecules" Chemistry World, Dec. 2009, p. 29, Royal Society of Chemistry, UK.

Clegg, William, et al.: "Cyclic carbonate synthesis catalysed by bimetallic aluminium-salen complexes" Chem. Eur. J., 2010, vol. 16, pp. 6828-6843, Wiley-VCH Verlag GmbH & Co., KGaA, Weinheim.

Melèndez, Jaisiel, et al: "One-component catalysis for cyclic carbonate synthesis" Chem. Commun., 2009, pp. 2577-2579, The Royal Society of Chemistry, UK.

Metcalfe, Ian S., et al.: "An integrated approach to energy and chemicals production" Energy Environ. Sci., 2010, vol. 3, pp. 212-215, The Royal Society of Chemistry, UK.

North, Michael, et al.: "Mechanism of Cyclic Carbonate Synthesis from Epoxides and CO2" Agneew Chem. Int. Ed., 2009, vol. 48, pp. 2946-2948, Wiley-VCH Verlag GmbH & Co., KGaA, Weinheim.

North, Michael, et al.: "A Gas-Phase Flow Reactor for Ethylene Carbonate Synthesis from Waste Carbon Dioxide" Chem. Eur. J., 2009, vol. 15, pp. 11454-11457, Wiley-VCH Verlag GmbH & Co., KGaA, Weinheim.

North, Michael, et al.: "Synthesis of cyclic carbonates from epoxides and CO2" Green Chemistry, 2010, DOI 10, 1039_c0GC00065e, The Royal Society of Chemistry, UK.

North, Michael, et al."Aluminium(salen) and Tetrabutylammonium Bromide CatalysedSynthesis of Cyclic Di-and Trithiocarbonates from Epoxides and Carbon Disulfide" SYNLETT, 2010, No. 4, pp. 0623-0627, Georg Thieme Verlag Stuttgart, New York.

Darensbourg, Donald J., et al., "The Copolymerization of Carbon Dioxide and [2-(3,4-Epoxycyclohexyl)ethyl] trimethoxysilane Catalyzed by (Salen)CrCl. Formation of a CO2 Soluble Polycarbonate", Inorg. Chem. 2003, 42, 4498-4500.

Darensbourg, Donald J., et al., "Cyclohexene Oxide/CO2 Copolymerization Catalyzed by Chromium(III) Salen Complexes and N-Methylimidazole: Effects of Varying Salen Ligand Substituents and Relative Cocatalyst Loading", Inorg. Chem. 2004, 43, 6024-6034.

Darensbourg, Donald J., et al., "Aluminum Salen Complexes and Tetrabutylammonium Salts: A Binary Catalytic System for Production of Polycarbonates from CO2 and Cyclohexene Oxide", Inorg. Chem. 2005, 44, 1433-1442.

Darensbourg, Donald J., et al., "Effective, Selective Coupling of Propylene Oxide and Carbon Dioxide to Poly(Propylene Carbonate) Using (Salen)CrN3 Catalysts", Inorg. Chem. 2005, 44, 4622-4629.

Darensbourg, Donald J., et al., "Syntheses and Structures of Epoxide Adducts of Soluble Cadmium(I1) Carboxylates. Models for the Initiation Process in EpoxideKOz Coupling Reactions", J. Am. Chem. Soc. 1995,117, 538-539.

Cheng, Ming, et al., "Catalytic Reactions Involving C1 Feedstocks: New High-Activity Zn(II)-Based Catalysts for the Alternating Copolymerization of Carbon Dioxide and Epoxides", J. Am. Chem. Soc. 1998, 120, 11018-11019.

Darensbourg, Donald J., et al., "Bis 2,6-difluorophenoxide Dimeric Complexes of Zinc and Cadmium and Their Phosphine Adducts: Lessons Learned Relative to Carbon Dioxide/Cyclohexene Oxide Alternating Copolymerization Processes Catalyzed by Zinc Phenoxides", J. Am. Chem. Soc. 2000, 122, 12487-12496.

Allen, Scott D., et al., "High-Activity, Single-Site Catalysts for the Alternating Copolymerization of CO2 and Propylene Oxide", JACS Communications, Published on Web Nov. 8, 2002, J. Am. Chem. Soc. 2002, 124, 14284-14285.

Darensbourg, Donald J., et al., "Mechanistic Aspects of the Copolymerization Reaction of Carbon Dioxide and Epoxides, Using a Chiral Salen Chromium Chloride Catalyst", JACS Articles, J. Am. Chem. Soc. 2002, 124, 6335-6342.

Lu, Xiao-Bing, et al., "Design of Highly Active Binary Catalyst Systems for CO2/Epoxide Copolymerization: Polymer Selectivity, Enantioselectivity, and Stereochemistry Control", JACS Articles, J. Am. Chem. Soc. 2006, 128, 1664-1674.

Darensbourg, Donald J., et al., "Supercritical carbon dioxide as solvent for the copolymerization of carbon dioxide and propylene oxide using a heterogeneous zinc carboxylate catalyst", Journal of Molecular Catalysis A: Chemical 104 ( 1995) LI-L4.

Walther, Martin, et al., "Synthesis of Azolyl Carboximidamides as Ligands for Zn(II) and Cu(II): Application of the Zn(II) Complexes as Catalysts for the Copolymerization of Carbon Dioxide and Epoxides1", JOC Article, J. Org. Chem. 2006, 71, 1399-1406.

Darensbourg, Donald J., et al., "Catalytic Activity of Zinc(I1) Phenoxides Which Possess Readily Accessible Coordination Sites. Copolymerization and Terpolymerization of Epoxides and Carbon Dioxide", American Chemical Society, Macromolecules 1995,28, 7577-7579.

Mang, Stephan, et al., "Copolymerization of CO2 and 1,2-Cyclohexene Oxide Using a CO2-Soluble Chromium Porphyrin Catalyst", American Chemical Society, Macromolecules 2000, 33, 303-308.

Darensbourg, Donald J., et al., "Pressure Dependence of the Carbon Dioxide/Cyclohexene Oxide Coupling Reaction Catalyzed by Chromium Salen Complexes. Optimization of the Comonomer-Alternating Enchainment Pathway", American Chemical Society, Organometallics 2005, 24, 144-148.

Darensbourg, Donald J., et al., "Copolymerization of CO2 and Epoxides Catalyzed by Metal Salen Complexes", Acc. Chem. Res. 2004, 37, 836-844.

Coates, Geoffrey W., et al., "Discrete Metal-Based Catalysts for the Copolymerization of CO2 and Epoxides: Discovery, Reactivity, Optimization, and Mechanism", Angew. Chem. Int. Ed. 2004, 43,6618-6639.

Baiker, Alfons, "Utilization of carbon dioxide in heterogeneous catalytic synthesis", Applied Organometallic Chemistry, Appl. Organometal. Chem. 14, 751-762 (2000).

"The contribution of the utilization option to reducing the CO2 atmospheric loading: research needed to overcome existing barriers for a full exploitation of the potential of the CO2 use", Science Direct, Catalysis Today 98 (2004) 455-462.

(56) References Cited

OTHER PUBLICATIONS

Omae, Iwao, "Aspects of carbon dioxide utilization", Science Direct, Catalysis Today 115 (2006) 33-52.
Zevenhoven, Ron, et al., "Chemical fixation of CO2 in carbonates: Routes to valuable products and long-term storage", Science Direct, Catalysis Today 115 (2006) 73-79.
Yoshida, M., et al., Synthesis of Cyclic Carbonates, Recycling of CO2, Chem. Eur. J. 2004, 10, 2886-2893.
Braunstein, Pierre, et al., "Reactions of Carbon Dioxide with Carbon-Carbon Bond Formation Catalyzed by Transition-Metal Complexes", American Chemical Society, Chem. Rev. 1980, 88, 747-764.
Gibson, Dorothy H., "The Organometallic Chemistry of Carbon Dioxide", American Chemical Society, Chem. Rev. 1996, 96, 2063-2095.
Shaikh, Abbas-Alli G., "Organic Carbonates", American Chemical Society, Chem. Rev. 1996, 96, 951-976.
Arakawa, Hironori, et al., "Catalysis Research of Relevance to Carbon Management: Progress, Challenges, and Opportunities", American Chemical Society, Chem. Rev. 2001, 101, 953-996.
Dell'Amico, Daniela Belli, et al., "Converting Carbon Dioxide into Carbamato Derivatives", American Chemical Society, Chem. Rev. 2003, 103, 3857-3897.
Darensbourg, Donald J., et al., "Catalysts for the reactions of epoxides and carbon dioxide", Coordination Chemistry Reviews, 153 (1996) 155-174.
Leitner, W., "The coordination chemistry of carbon dioxide", Coordination Chemistry Reviews, 153 (1996) 257-284.
Ungvary, Ferenc, Application of transition metals in hydroformylation. Annual survey covering the year 1995, Coordination Chemistry Reviews, 160 (1997) 129-159.
Ungvary, Ferenc, Application of transition metals in hydroformylation: annual survey covering the year 1996, Coordination Chemist Reviews, 167 (1997) 233-260.
Ungvary, Ferenc, "Hydroformylation", Coordination Chemist Reviews, 170 (1998) 245-281.
Yin, Xiaolong, et al., "Recent developments in the activation of carbon dioxide by metal complexes", Coordination Chemistry Reviews, 181 (1999) 27-59.
Walther, Dirk, et al., "Carbon dioxide and metal centres: from reactions inspired by nature to reactions in compressed carbon dioxide as solvent", Coordination Chemistry Reviews, 182 (1999) 67-100.
Tanaka, Koji, et al., "Multi-electron reduction of CO2 via Ru—CO2, —C(O)OH, —CO, —CHO, and —CH2OH species", Coordination Chemistry Reviews 226 (2002) 211-218.
Ungvary, Ferenc, "Application of transition metals in hydroformylation annual survey covering the year 2001", Coordination Chemistry Reviews 228 (2002) 61-82.
Ungvary, Ferenc, "Application of transition metals in hydroformylation annual survey covering the year 2002", Science Direct, Coordination Chemistry Reviews 241 (2003) 295-312.
Jessop, Philip G., et al., "Recent advances in the homogeneous hydrogenation of carbon dioxide", Science Direct, Coordination Chemistry Reviews 248 (2004) 2425-2442.
Ungvary, Ferenc, "Application of transition metals in hydroformylation annual survey covering the year 2003", Science Direct, Coordination Chemistry Reviews 248 (2004) 867-880.
Xiaoding, Xu, et al., "Mitigation of CO2 by Chemical Conversion: Plausible Chemical Reactions and Promising Products", American Chemical Society, Energy & Fuels 1996, 10, 305-325.
Pacheco, Michael A., et al., "Review of Dimethyl Carbonate (DMC) Manufacture and Its Characteristics as a Fuel Additive", American Chemical Society, Energy & Fuels 1997, 11, 2-29.
"Green Chemical Processing Using CO2", American Chemical Society, Ind. Eng. Chem. Res. 2003, 42, 1598-1602.
Sun, Jianmin, et al., "Development in the green synthesis of cyclic carbonate from CO2 using ionic liquids", Science Direct, Journal of Organometallic Chemistry 690 (2005) 3490-3497.
Sugimoto, Hiroshi, et al., "Copolymerization of Carbon Dioxide and Epoxide", Journal of Polymer Science: Part A: Polymer Chemistry, vol. 42, 5561-5573 (2004).

Carmona, Ernesto, et al., "Electron-rich metal complexes for C02 and CS2 incorporation", Pure & Appl. Chem., vol. 61, No. 10, pp. 1701-1706, 1989.
Aresta, Michele, "Carbon dioxide asa building-block for molecular organic compounds", The Chemical Society, RSC Wokshop, Burlington House, Jul. 27, 2006.
Rayner, Prof. Chris, "Converting carbon dioxide to chemicals", Burlington House, Jul. 27, 2006, RSC Advancing the Chemical Sciences.
Vanderwal, Christopher D., et al.: "Enantioselective Formal Hydration of a,β-Unsaturated Imides by Al—Catalyzed Conjugate Addition of Oxime Nucleophiles" J.Am. Chem. Soc. 2004, vol. 126, 14724-14725, American Chemical Society.
Larrow, Jay F., et al.: "A Practical Method for the Large-Scale Preparation of [N,N'-Bis(3,5-di-tert-buty lsalicylidene)-1,2-cyclohexanediaminato(2-) ]manganese (III) Chloride, a Highly Enantioselective Epoxidation Catalyst" J. Org. Chem. 1994, vol. 59, 1939-1942, American Chemical Society.
Shen, Yu-Mei, et al.: "Chemical Fixation of Carbon Dioxide Catalyzed by Binaphthyldiamino Zn, Cu, and Co Salen-Type Complexes" J. Org. Chem. 2003, vol. 68, 1559-1562, American Chemical Society.
Wang, Yuhong, et al.: "Five-coordinate organoaluminum acetylides and crystal structure of the hydrosylate, [Salophen(tBu)Al]2O", J. of Organic Chemistry, 2004, vol. 689, 759-765.
Matsumoto, Kazuhiro, et al.: "Catalytic Enantioselective Epoxidation of Unfunctionalized Olefins: Utility of a Ti(Oi-Pr)4-Salan-H2O2 System," Synlett 2006, vol. 20, 3545-3547, Georg Thieme Verlag Stuttgart, New York.
Shitama, Hiroaki, et al.: "Asymmetric epoxidation using aqueous hydrogen peroxide as oxidant: bio-inspired construction of pentacoordinated Mn-salen complexes and their catalysis," Tetrahedron Letters 2006, vol. 47, 3203-3207, Elsevier Ltd.
Gandelman, Mark, et al.: "Highly Enantioselective Catalytic Conjugate Addition of N-Heterocycles to a,β- Unsaturated Ketones and Imides," Chem. Int. Ed. 2005, vol. 44, 2393-2397, Wiley-VCH Verlag GmbH & Co. KGaC, Weinheim.
Kureshy, R.I., et al.: "Environment friendly protocol for enantioselective epoxidation of non-functionalized alkenes catalyzed by recyclable homochiral dimeric Mn(III) salen complexes with hydrogen peroxide and UHP adduct as oxidants," Catalysis Letters, 2006, vol. 107, Nos. 1-2, Springer Science + Business Media, Inc.
Nomura, Nobuyoshi, et al.: "Stereoselective Ring-Opening Polymerization of a Racemic Lactide by Using Achiral Salen— and Homosalen—Aluminum Complexes," Chem Eur. J., 2007, vol. 13, 4433-4451, Wiley-VCH Verlag GmbH & Co. KGaA, Weinheim.
Gurian, Patrick L., et al.: "Aluminium Complexes of N,N,'-Ethylenebis(salicylideneimine)-( H2salen). X-Ray Crystal Structures of [{Al(salen)},2(u-O)].MeCN and [Al(OC6H2Me3,-2,4,6)(salen)]," J. Chem. Soc., Dalton Trans. (Inorganic), 1991, vol. 6, 1449-1456.
Atwood, David, et al.: "Group 13 Compounds Incorporating Salen Ligands," Chem. Rev. 2001, vol. 101, 37-52, American Chemical Society.
Gisch, Nicolas, et al.: "Enzymatically Activated cycloSal-d4T-monophosphates: The Third Generation of cycloSal-Pronucleotides," J. Med. Chem. 2007, vol. 50, 1658-1667, American Chemical Society.
Rutherford, Drew, et al.: "Five-Coordinate Aluminum Amides," Organometallics 1996, vol. 15, 4417-4422, American Chemical Society.
Pervaiz, Muhammad, et al.: "Carbon storage potential in natural fiber composites," Resources, Conservation and Recycling 2003, vol. 39, 325-340, Elsevier Science B.V.
Irie, Ryo, et al.: "Enantioselective Expoxidation of Chromene Derivatives using Hydrogen peroxide as a Terminal Oxidant," Synlett 1994, 255-256 (Japan).
Achard, Theirry, R.J., et al.: "Asymmetric Catalysis of Carbon-Carbon Bond-Forming Reactions Using Metal(salen) Complexes," Synlett 2005, No. 12, 1828-1847, Georg Thieme Verlag Stuttgart, New York.

(56) References Cited

OTHER PUBLICATIONS

Iida, Takehiko, et al.: "Cyclocondensation of Oxalyl Chloride with 1,2-Glycols," Tetrahedron, 1993, vol. 49, No. 46, 10511-10530, Ferguson Pres, Ltd. UK.

North, Michael, "Synthesis and applications of non-racemic cyanohydrins," Tetrahedron: Asymmetry 2003, vol. 14 147-176, Elsevier Science Ltd.

Dzugan, Sharlene J., et al.: "Factors Affecting Al—C Bond Reactivity of Tetradentate Schiff-Base Organoaluminum Complexes," Inorg. Chem 1986, vol. 25, 2858-2864, American Chemical Society.

Sammis, Glenn M., et al.: "Highly Enantioselective, Catalytic Conjugate Addition of Cyanide to a,β-Unsaturated Imides," J. Am. Chem. Soc. 2003, vol. 125, 4442-4443, American Chemical Society.

Taylor, Mark S., et al.: "Enantioselective Michael additions to a,β-unsaturated imides catalyzed by a Salen-Al complex," Sep. 2003 vol. 125, Issue 37, 11204-11205.

Nakano, Koji, et al.: "Selective Formation of Polycarbonate over Cyclic Carbonate: Copolymerization of Epoxides with Carbon Dioxide Catalyzed by a Cobalt(III) Complex with a Piperidinium End-Capping Arm," Chem. Int. Ed. 2006, vol. 45, 7274-7277, Wiley-VCH Verlag GmbH & Co. KGaA, Weinheim.

Maroto, A., et al.: "Relationship between surface properties of PtSn±SiO2 catalysts and their catalytic performance for the CO2 and propylene reaction to yield hydroxybutanoic acid," Appl. Organometal. Chem. 2000, vol. 14, 783-788, John Wiley & Sons, Ltd.

Balskus, Emily P., et al.: "a,β--Unsaturated β-Silyl Imide Substrates for Catalytic, Enantioselective Conjugate Additions: A Total Synthesis of (+)-Lactacystin and the Discovery of a New Proteasome Inhibitor," J.. Am. Chem. Soc. 2006, vol. 128, 6810-6812, American Chemical Society.

Sung-Suh, Hyung Mi, et al.: "Photoinduced activation of CO2 by rhenium complexes encapsulated in molecular sieves," Appl. Organometal. Chem. 2000 vol. 14, 826-830, John Wiley & Sons, Ltd.

Kosugi, Yoshio, et al.: "Carboxylation of alkali metal phenoxide with carbon dioxide at terrestrial temperature," Appl. Organometal. Chem. 2000, vol. 14, 841-843, John Wiley & Sons, Ltd.

Ballivet-Tkatchenko, Danielle, et al.: "Electrocatalytic reduction of CO2 for the selective carboxylation of olefins," Appl. Organometal. Chem., 2000, vol. 14, 847-849, John Wiley & Sons, Ltd.

Tanaka, Koji, et al.: "Selective formation of ketones by electrochemical reduction of CO2 catalyzed by ruthenium complexes," Appl. Organometal. Chem., 2000, vol. 14, 863-866, John Wiley & Sons, Ltd.

Styring, Peter, et al.: "A polymer-supported nickel(II) catalyst for room temperature Tamao-Kumada-Corriu coupling reactions," Catalysis Letters 2001, vol. 77, No. 4, Plenum Publishing Corporation.

Molnar, Ferenc, et al.: Multisite Catalysis: A Mechanistic Study of β-Lactone Synthesis from Epoxides and CO-Insights into a Difficult Case of Homogeneous Catalysis, Chem. Eur. J., 2003, vol. 9, No. 6, 1273-1280, Wiley-VCH Verlag GmbH & Co. KGaA, Weinheim.

Phan, Nam, T.S., et al.: "Solid-supported cross-coupling catalysts derived from homogeneous nickel and palladium coordination complexes," Appl. Organometal Chem., 2000, vol. 14, 794-798, The Royal Society of Chemistry, UK.

Shen, Yu-Mei, "Chemical Fixation of Carbon Dioxide Co-Catalyzed by a Combination of Schiff Bases or Phenols and Organic Bases," Eur. J. Org. Chem. 2004, 3080-3089, Wiley-VCH Verlag GmbH & co. KGaA, Weinheim.

Braunstein, Pierre, et al.: "Carbon Dioxide Activation and Catalytic Lactone Synthesis by Telomerization of Butadiene and CO2," J. Am. Chem. Soc., 1988, vol. 110, 3207-3212, American Chemical Society.

Tsuda, Tetsuo, et al.: "Nickel(0)-Catalyzed Alternating Copolymerization of Carbon Dioxide with Diynes to Poly ( 2-pyrones)," J. Am. Chem. Soc. 1992, vol. 114, 1498-1499, American Chemical Society.

Hoffman, William A., III: "Convenient Preparation of Carbonates from Alcohols and Carbon Dioxide," J. Org. Chem. 1982, vol. 47, 5209-5210, American Chemical Society.

Tsuda, Tetsuo, et al.: "Nickel(O)-Catalyzed Cycloaddition of Diynes and Carbon Dioxide to Bicyclic α-Pyrones," J. Org. Chem. 1988, vol. 53, 3140-3145, American Chemical Society.

Shi, Min, et al.: "Transition-Metal-Catalyzed Reactions of Propargylamine with Carbon Dioxide and Carbon Disulfide," J. Org. Chem. 2002, vol. 67, 16-21, American Chemical Society.

Lefeber, C., et al.: "Regioselektive Reaktionen der fremdligandfreien Titanocen-Alkin-Komplexe Cp,Ti( RC,SiMe,) (R = Me,3, Ph, 1Bu, nBu)," J. Organometallic Chemistry, 1995 vol. 501, 179-188, Elsevier Science S.A.

Tsuda, Tetsuo, et al.: "Nickel(0)-Catalyzed Cycloaddition Copolymerization of Ether Diynes with Carbon Dioxide to Poly(2-pyrone)s," Macromolecules 1996, vol. 28, 1356-1359, American Chemical Society.

McGee, William, et al.: "Palladium-Catalyzed Generation of 0-Allylic Urethanes and Carbonates from Amines/Alcohols, Carbon Dioxide, and Allylic Chlorides," Organometallics 1993, vol. 12, 1429-1433, American Chemical Society.

Bartoli, Giuseppe, et al.: "Direct Catalytic Synthesis of Enantiopure 5-Substituted Oxazolidinones from Racemic Terminal Epoxides," Organic Letters 2005, vol. 7, No. 10, 1983-1985, American Chemical Society.

Mizojiri, Ryo, et al.: Regioselectivity in the nickel-catalysed coupling of cyclic carbonates of but-3-ene-1,2-diols with organoborates, J. Chem. Soc. Perkin Trans. 1995, 2073-2075.

Gholamkhass, Bobak, et al.: "Architecture of Supramolecular Metal Complexes for Photocatalytic CO2 Reduction: Ruthenium—Rhenium Bi— and Tetranuclear Complexes," Inorganic Chemistry, 2005, vol. 44, No. 7, American Chemical Society.

Takavec, Thomas N., et al.: "Regioselectivity in nickel(0) catalyzed cycloadditions of carbon dioxide with diynes," Tetrahedron 60, 2004, 7431-7437, Elsevier Ltd. UK.

Phan, Nam T.S., et al: "Polymer-supported palladium catalysed Suzuki-Miyaura reactions in batch and a mini-continuous flow reactor system," Tetrahedron 61, 2005, 12065-12073, Elsevier Science Ltd. UK.

Matsumoto, Kazutsugu, et al.: "Enzyme-Mediated Enantioselective Hydrolysis of Cyclic Carbonates," Tetrahedron Letters, 1995, vol. 36, No. 36, 6499-6502, Elsevier Science Ltd. UK.

Chang, Han-Ting, et al.: "A Practical Route to Enantiopure 1,2-Aminoalcohols." Tetrahedron Letters, 1996, vol. 37, No. 19, 3219-3222, Elsevier Science Ltd. UK.

Schultze, Lisa M., et al.: "Practical Synthesis of the anti-HIV Drug, PMPA," Tetrahedron Letters 39, 1998, 1853-1856, Elsevier Science Ltd. UK.

S. Jegham, et al.: "Use of Chiral Glycerol 2,3-Carbonate in the Synthesis of 3-Aryl-2-oxazolidinones," Tetrahedron Letters 39, 1998, 4453-4454, Elsevier Science Ltd. UK.

Phan, Nam, T.S., et al.: "A polymer-supported salen-type palladium complex as a catalyst for the Suzuki—Miyaura cross-coupling reaction," Tetrahedron Letters 45, 2004, 7915-7919, Elsevier Science Ltd. UK.

Hall, Peter, et al., "Converting CO2 Into Fuels and Chemicals: The Formic Acid Economy" (2006).

Brunner, M., et al., "Kinetic Resolution of Oxiranes by Use of Chiral Lewis Acid Catalysts", Institute of Technical Chemistry and Petrolchemistry. RWTH Aachen, Templegraben 55. 52056 Aachen, FRO; Received Oct. 1, 1993; Published Dec. 1993.

Huntsman, "JEFFSOL Alkylene Carbonates," Huntsman Corporation copyright 2001.

Huntsman, Technical Bulletin, "JEFFSOL® Alkylene Carbonates Synthesis of Polycarbonates and 6-Membered Carbonates", JSPOLYCARB-0905, Huntsman Corporation copyright 2005.

Clements, John H., "Reactive Applications of Cyclic Alkylene Carbonates", Copyright 2003 American Chemical Society, Ind. Eng. Chem. Res. 2003, 42, 663-674.

Huntsman, Technical Bulletin, "UltraPure® Ethylene Carbonate", [CAS 96-49-1], 1124-1205; Copyright 2005 Huntsman Corporation.

Shen, Yu-Mei, et al., "Phenol and Organic Bases Co-Catalyzed Chemical Fixation of Carbon Dioxide with Terminal Epoxides to Form Cyclic Carbonates", State Key Laboratory of Organometallic Chemistry, Shanghai Institute of Organic Chemistry, Chinese Acad-

(56) References Cited

OTHER PUBLICATIONS emy of Sciences, 354 Fenglin Lu, Shanghai 200032, P.R. China; Received Oct. 28, 2002; Accepted: Dec. 9, 2002.

Takata, Toshikazu, et al., "Synthesis of Calix[4]arene and Porphyrin Tethering Four Chiral Five-Membered Cyclic Carbonates", Enantiomer, vol. 7, pp. 129-132; Department of Applied Chemistry, Graduate School of Engineering, Osaka Prefecture University, Osaka, Japan; Received Dec. 18, 2001; accepted Feb. 9, 2002.

Clegg, William, et al., "A Bimetallic Aluminum(salen) complex for the synthesis of 1.3-oxathiolane-2-thiones and 1.3-dithiolane-2-thiones" J. Org. Chem., DOI 10_1021_io101121h JOC, vol. XXX, No. XX, XXXX, American Chemical Society, Jun. 21, 2010.

Williams, Charlotte K., "CO2 as a feedstock in polymer synthesis", Imperial College London, Science, 2006, 311-484.

Maroto-Valer, M. Mercedes, "Photochemical transformation of carbon dioxide", School of Chemical, Environmental and Mining Engineering (SChEME) Nottingham Fuel and Energy Centre (NFEC), 2006.

Donald J. Darensbourg; Making Plastics from Carbon Dioxide: Salen Metal Complexes as Catalysts for the Production of Polycarbonates from Epoxides and C02: Chemical Review: 2007, vol. 107, No. 6 pp. 2388-2410; D American Chemical Society; Published on Web Apr. 21, 2007.

Donald J. Darensbourg, Paolo Bottarelli, Jeremy R. Andreatta; Inquiry into the Formation of Cyclic Carbonates during the (Salen)CrX Catalyzed C02/Cyciohexene Oxide Copolymerization Process in the Presense of Ionic Initiators; Macromolecules; 2007, vol. 40, No. 21, pp. 7727-7729: American Chemical Society; Published on D Web 9118/2007.

North M .. Young C. Bimetallic aluminium(acen) complexes as catalysts for the synthesis of cyclic carbonates from carbon dioxide and epoxides. Catalysis Science & Technology Jan. 2011(1).93-99.

Melendez, J., North M, Villuendas P, Young C. One-component bimetallic aluminium(salen)-based catalysts for cyclic carbonate synthesis and their immobilization. Dalton Transactions 2011, 40(15), 3885-3902.

Taylor, "Enantioselective Michael Additions to .alpha.,.beta.—Unsaturated Imides Catalyzed by Salen-Al Complex." Journal of the American Chemical Society, 2003 125(37), 11204-11205.

* cited by examiner

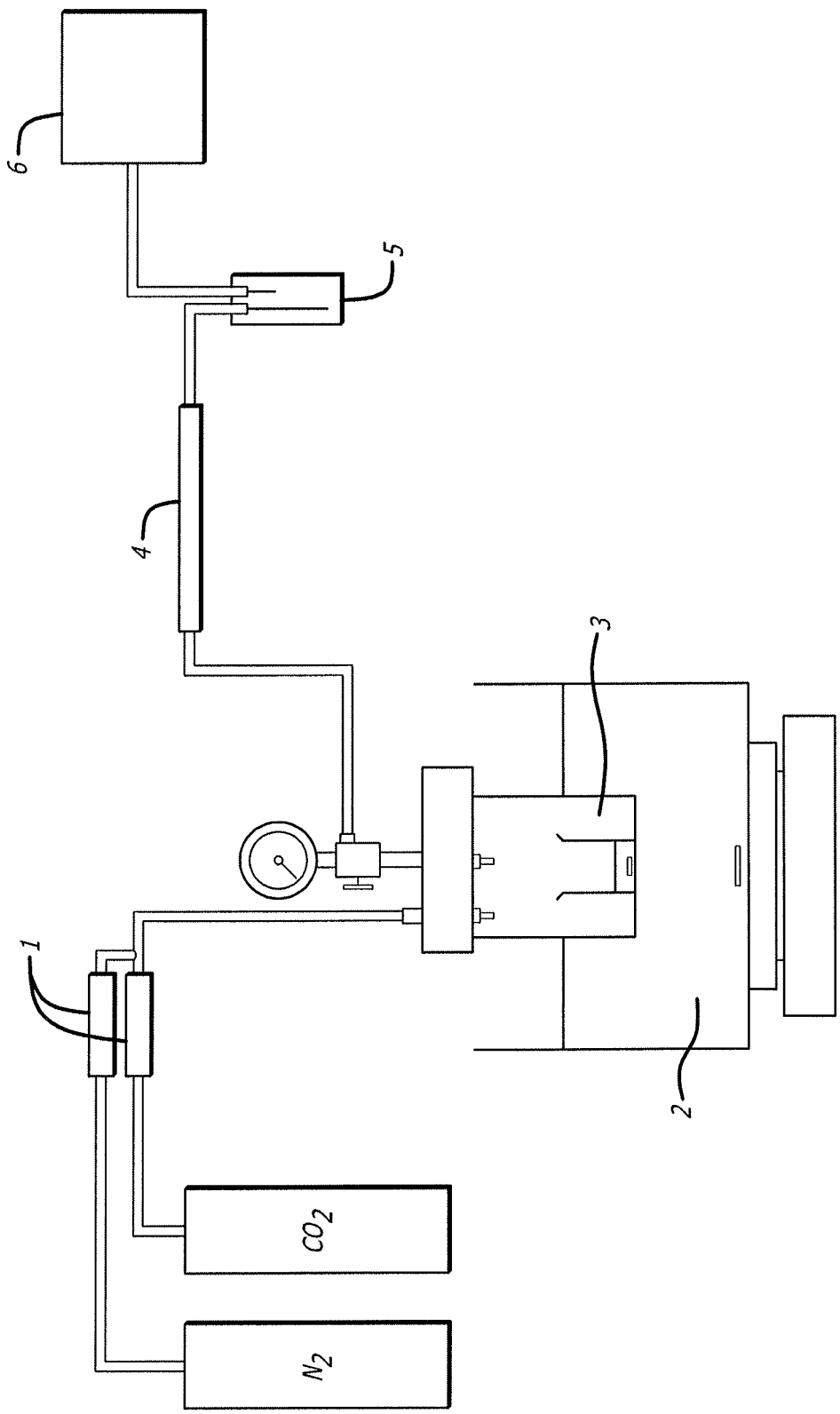

SYNTHESIS OF CYCLIC CARBONATES

CROSS-REFERENCE TO RELATED APPLICATIONS

This application is a continuation of U.S. patent application Ser. No. 12/921,264, Filed Sep. 7, 2010, which claims priority to International Application No. PCT/GB2009/000624, filed on Mar. 6, 2009, which claims priority to (1) Great Britain Patent Application No. 0804345.7, filed Mar. 7, 2008, and (2) Great Britain Patent Application No. 0821092.4, filed Nov. 18, 2008, each of which is incorporated by reference in its entirety.

COPYRIGHT NOTICE

A portion of the disclosure of this patent document contains material that is subject to copyright protection. The copyright owner has no objection to the facsimile reproduction by anyone of the patent document or the patent disclosure, as it appears in the Patent and Trademark Office patent files or records, but otherwise reserves all copyright rights whatsoever.

FIELD OF THE DISCLOSURE

This disclosure relates to a process for synthesising cyclic carbonates from epoxides and carbon dioxide using aluminium(salen) complexes as catalysts. The disclosure also provides novel aluminium(salen) complexes, and their synthesis.

BACKGROUND

Cyclic carbonates are commercially important products currently manufactured on a multi-tonne scale for use as polar aprotic solvents, additives, antifoam agents for anti-freeze, plasticisers, and monomers for polymer synthesis (see Darensbourg, et al., *Coord. Chem. Rev.*, 153 (1996), 155-174; Coates, et al., *Angew. Chem. Int. Ed.*, 43 (2004), 6618-6639).

The synthesis of cyclic carbonates generally involves the reaction of epoxides with carbon dioxide, and hence could be used to sequestrate carbon dioxide, thus reducing the level of greenhouse gases in the atmosphere.

Catalysts for the synthesis of cyclic carbonates from epoxides and carbon dioxide are known in the art (see Darensbourg, et al., *Coord. Chem. Rev.*, 153 (1996), 155-174; Yoshida, et al., *Chem. Eur. J*, 10 (2004), 2886-2893; Sun, et al., *J. Organomet. Chem.*, 690 (2005), 3490-3497) although these require elevated reaction temperatures and/or high pressures of carbon dioxide, the reaction often being conducted in supercritical carbon dioxide (see Lu, et al., *App. Cat. A*, 234 (2002), 25-33).

Ratzenhofer, et al., (*Angew. Chemie Int. Ed. Engl.*, 19 (1980), 317-318) succeeded in carrying out the reaction between 2-methyloxirane and carbon dioxide at room temperature and atmospheric pressure using catalysts consisting of a mixture of a metal halide and a Lewis base. However, a long reaction time of 7 days was required. Kisch, et al., (*Chem. Ber.*, 119 (1986), 1090-1094), carrying out the same reaction under the same conditions and also using catalysts of this type, reports a reaction time of 3.5 to 93 hours using up to 4 mol % of a $ZnCl_2$ catalyst and up to 16 mol % of a $(nButyl)_4NI$ catalyst.

Lu, et al., (*J. Mol. Cat. A*, 210 (2004), 31-34; *J. Cat.*, 227 (2004), 537-541) describe the use of tetradentate Schiff-base aluminium complexes in conjunction with a quaternary ammonium salt or polyether-KY complexes as catalyst systems for the reaction of various epoxides with carbon dioxide at room temperature and about 6 atmospheres.

Metal(salen) complexes, including aluminium(salen) complexes, are well-known in the art for their use as catalysts. Lu, et al., *App. Cat. A*, 234 (2002), 25-33, describes the use of a monomeric aluminium(salen) catalyst.

Also known in the art is the method of synthesising aluminium(salen) catalysts by treating a salen ligand with $Me_3Al$, $Et_3Al$, $Me_2AlCl$, $Me_2AlOTf$, $Et_2AlBr$ or $Et_2AlCl$ in a two-stage process (reviewed in Atwood and Harvey, *Chem. Rev.*, 2001, 101, 37-52).

The present inventor has previously found that, in the presence of a tetraalkylammonium halide cocatalyst, dimeric aluminium(salen) complexes are highly active catalysts for the reaction of epoxides with carbon dioxide to produce cyclic carbonates, and allow the reaction to be carried out at room temperature and atmospheric pressure, using short reaction times and commercially viable amounts of catalyst, as described in Melendez, J., et al., *Eur. J. Inorg Chem*, 2007, 3323-3326 and co-pending UK patent application No. 0708016.1, filed 25 Apr. 2007, now published as WO 2008/132474.

SUMMARY

Briefly stated, the disclosed embodiments illustrate a process that incorporates the co-catalyst required in this work into the catalyst molecule, so as to reduce or eliminate the amount of separate components needed. Furthermore, the disclosed embodiments illustrate a process that immobilises the combined catalyst and co-catalyst on a solid support.

Accordingly, a first aspect of a disclosed embodiment provides a dimeric aluminium(salen) catalyst of formula I:

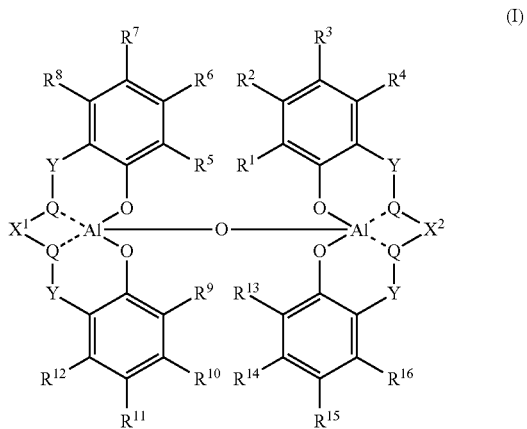

wherein:

Y-Q is $CR^{C1}=N$ or $CR^{C1}R^{C2}—NR^{N1}$, where $R^{C1}$, $R^{C2}$ and $R^{N1}$ are independently selected from H, halo, optionally substituted $C_{1-20}$ alkyl, optionally substituted $C_{5-20}$ aryl, ether and nitro;

each of the substituents $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, and $R^{16}$, is independently selected from H, halo, optionally substituted $C_{1-20}$ alkyl (including $CAr_3$, where Ar is a $C_{5-20}$ aryl group), optionally substituted $C_{5-20}$ aryl, optionally substituted $C_{3-20}$ heterocyclyl, ether and nitro;

$X^1$ and $X^2$ are independently either (i) a $C_{2-5}$ alkylene chain, which is optionally substituted by one or more groups selected from $C_{1-4}$ alkyl and $C_{5-7}$ aryl, or a $C_{1-3}$ bisoxyalkylene chain, which is optionally substituted by one or more groups selected from $C_{1-4}$ alkyl and $C_{5-7}$ aryl or (ii) represent a divalent group selected from $C_{5-7}$ arylene, $C_{5-7}$ cyclic alkylene and $C_{3-7}$ heterocyclylene, which may be optionally substituted;

(i) (a) at least one of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, and $R^{16}$ is selected from L-A, where L is a single bond or a $C_{1-10}$ alkylene group and A is an ammonium group paired with a counterion selected from Cl, Br and I; and/or (b) at least one of $X^1$ and $X^2$ is a divalent $C_{3-7}$ heterocyclene group, containing a ring atom which is a quaternary nitrogen atom paired with a counterion selected from Cl, Br and I; and/or (c) at least one of $X^1$ and $X^2$ is a $C_{2-5}$ alkylene chain or a $C_{1-3}$ bisoxyalkylene chain, substituted by a group -Q-L-A, where Q is either —C(=O)—NH—, or a single bond; and/or (ii) (a) one of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, and $R^{16}$ is L-A', where L is as defined above and A' is a ammonium linking group bound to a solid support and paired with a counterion selected from Cl, Br and I; or (b) one of $X^1$ and $X^2$ is a divalent $C_{3-7}$ heterocyclene group, containing a ring atom which is a quaternary nitrogen forming part of an ammonium linking group bound to a solid support and paired with a counterion selected from Cl, Br and I; or (c) one of $X^1$ and $X^2$ is a $C_{2-5}$ alkylene chain or a $C_{1-3}$ bisoxyalkylene chain, substituted by a group -Q-L-A'.

Thus, when the catalyst is covalently bound to a solid support, only one linking group to the solid support is present. However, one or more ammonium groups/quaternary nitrogen atoms may be present.

The catalysts of formula I where: (a) at least one of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, and $R^{16}$ is selected from L-A; and/or (b) at least one of $X^1$ and $X^2$ is a divalent $C_{3-7}$ heterocyclene group, containing a ring atom which is a quaternary nitrogen atom paired with a counterion selected from Cl, Br and I; and/or (c) at least one of $X^1$ and $X^2$ is a $C_{2-5}$ alkylene chain or a $C_{1-3}$ bisoxyalkylene chain, substituted by a group -Q-L-A, where Q is either —C(=O)— or a single bond, may be immobilized on a solid support, either by the use of steric effects or by electrostatic binding.

If the catalyst of formula I includes one or more chiral centres, then it may be a (wholly or partially) racemic mixture or other mixture thereof, for example, a mixture enriched in one enantiomer or diastereoisomer, a single enantiomer or diastereoisomer, or a mixture of the stereoisomers. Methods for the preparation (e.g., asymmetric synthesis) and separation (e.g., fractional crystallisation and chromatographic means) of such isomeric forms are either known in the art or are readily obtained by adapting the methods taught herein, or known methods, in a known manner. Preferably the catalyst of formula I is a single enantiomer, if a chiral centre is present.

The dimeric aluminium(salen) catalysts of the first aspect may be of formula Ia:

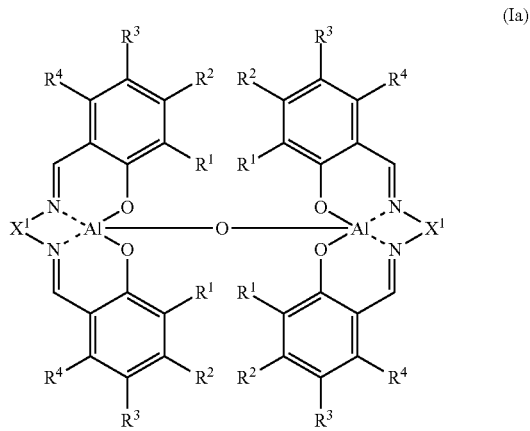

(Ia)

where $R^1$, $R^2$, $R^3$, $R^4$ and $X^1$ are as defined above; and (a) at least one of $R^1$, $R^2$, $R^3$ and $R^4$ is selected from L-A, where L is a single bond or a $C_{1-10}$ alkylene group and A is an ammonium group paired with a counterion selected from Cl, Br and I; and/or (b) $X^1$ is a divalent $C_{3-7}$ heterocyclene group, containing a ring atom which is a quaternary nitrogen atom paired with a counterion selected from Cl, Br and I; or (c) $X^1$ is a $C_{2-5}$ alkylene chain or a $C_{1-3}$ bisoxyalkylene chain, substituted by a group -Q-L-A, where Q is either —C(=O)— or a single bond.

A second aspect of a disclosed embodiment provides a process for the production of cyclic carbonates comprising contacting an epoxide with carbon dioxide in the presence of a dimeric aluminium(salen) catalyst according to the first aspect of a disclosed embodiment.

The reaction of the second aspect may be defined as follows:

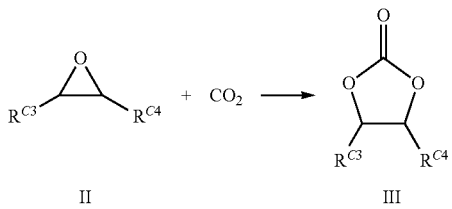

wherein $R^{C3}$ and $R^{C4}$ are independently selected from H, optionally substituted $C_{1-10}$ alkyl, optionally substituted $C_{3-20}$ heterocyclyl and optionally substituted $C_{5-20}$ aryl, or $R^{C3}$ and $R^{C4}$ form an optionally substituted linking group between the two carbon atoms to which they are respectively attached. The linking group, together with the carbon atoms to which it is attached, may form an optionally substituted $C_{5-20}$ cycloalkyl or $C_{5-20}$ heterocylyl group. The $C_{5-20}$ cycloalkyl or $C_{5-20}$ heterocylyl group may be substituted only in a single position on the ring, for example, adjacent the epoxide. Suitable substituents, include optionally substituted $C_{1-10}$ alkyl, optionally substituted $C_{3-20}$ heterocyclyl and optionally substituted $C_{5-20}$ aryl.

A possible substituent for the $C_{1-10}$ alkyl group is a $C_{5-20}$ aryl group.

The second aspect of a disclosed embodiment also provides the use of a dimeric aluminium(salen) catalyst of the first aspect of a disclosed embodiment for the production of cyclic carbonates from epoxides.

A third aspect of a disclosed embodiment provides a process for the synthesis of a dimeric aluminium(salen) catalyst of formula I.

BRIEF DESCRIPTION OF DRAWINGS

FIG. 1 shows a flow reactor for use with the disclosed catalysts.

DETAILED DESCRIPTION OF THE EMBODIMENTS

Definitions

Epoxide: The term "epoxide", as used herein, may pertain to a compound of the formula:

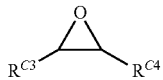

wherein $R^{C3}$ and $R^{C4}$ are independently selected from H, optionally substituted $C_{1-10}$ alkyl, optionally substituted $C_{3-20}$ heterocyclyl and optionally substituted $C_{5-20}$ aryl, or $R^{C3}$ and $R^{C4}$ form an optionally substituted linking group between the two carbon atoms to which they are respectively attached. The linking group, together with the carbon atoms to which it is attached, may form an optionally substituted $C_{5-20}$ cycloalkyl or $C_{5-20}$ heterocylyl group. The $C_{5-20}$ cycloalkyl or $C_{5-20}$ heterocylyl group may be substituted only in a single position on the ring, for example, adjacent the epoxide. Suitable substituents, include optionally substituted $C_{1-10}$ alkyl, optionally substituted $C_{3-20}$ heterocyclyl and optionally substituted $C_{5-20}$ aryl.

The optional substituents may be selected from: $C_{1-10}$ alkyl, $C_{3-20}$ heterocyclyl, $C_{5-20}$ aryl, halo, hydroxy, ether, cyano, nitro, carboxy, ester, amido, amino, acylamido, ureido, acyloxy, thiol, thioether, sulfoxide, sulfonyl, thioamido and sulfonamino.

In some embodiments, the $C_{1-10}$ alkyl group is substituted by a $C_{5-20}$ aryl group.

Preferably, the epoxide is a terminal epoxide, i.e. $R^{C4}$=H.

In some embodiments, $R^{C3}$ is selected from optionally substituted $C_{1-4}$ alkyl and optionally substituted $C_{5-7}$ aryl. In some of these embodiments $R^{C3}$ is unsubstituted.

Preferred epoxides are ethylene oxide ($R^{C3}$=$R^{C4}$=H), propylene oxide ($R^{C3}$=methyl, $R^{C4}$=H) butylene oxide ($R^{C3}$=ethyl, $R^{C4}$=H), and styrene oxide ($R^{C3}$=phenyl, $R^{C4}$=H).

Cyclic carbonate: the term "cyclic carbonate", as used herein, may pertain to a compound of the formula:

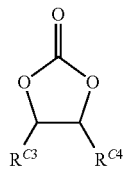

wherein $R^{C3}$ and $R^{C4}$ are as defined above.

Solid support: Catalysts of a disclosed embodiment may be immobilized on a solid support by:
(a) covalent binding (those where one of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, and $R^{16}$ is selected from L-A');
(b) steric trapping; or
(c) electrostatic binding.

These various methods are reviewed by Carlos Baleizão and Hermenegildo Garcia in "Chiral Salen Complexes: An Overview to Recoverable and Reusable Homogeneous and Heterogeneous Catalysts" (*Chem. Rev.* 2006, 106, 3987-4043).

For covalent binding, the solid support needs to contain or be derivatized to contain reactive functionalities which can serve for covalently linking a compound to the surface thereof. Such materials are well known in the art and include, by way of example, silicon dioxide supports containing reactive Si—OH groups, polyacrylamide supports, polystyrene supports, polyethyleneglycol supports, and the like. A further example is sol-gel materials. Silica can be modified to include a 3-chloropropyloxy group by treatment with (3-chloropropyl)triethoxysilane. Another example is Al pillared clay, which can also be modified to include a 3-chloropropyloxy group by treatment with (3-chloropropyl)triethoxysilane. Such supports will preferably take the form of small beads, pins/crowns, laminar surfaces, pellets or disks. They may also take the form of powders. Solid supports for covalent binding of particular interest in a disclosed embodiment include siliceous MCM-41 and MCM-48 (modified with 3-aminopropyl groups), ITQ-2 and amorphous silica, SBA-15 and hexagonal mesoporous silica. Also of particular interest are sol-gels. Other conventional forms may also be used.

For steric trapping, the most suitable class of solid support is zeolites, which may be natural or modified. The pore size must be sufficiently small to trap the catalyst but sufficiently large to allow the passage of reactants and products to and from the catalyst. Suitable zeolites include zeolites X, Y and EMT as well as those which have been partially degraded to provide mesopores, that allow easier transport of reactants and products.

For the electrostatic binding of the catalyst to a solid support, typical solid supports may include silica, Indian clay, Al-pillared clay, Al-MCM-41, K10, laponite, bentonite, and zinc-aluminum layered double hydroxide. Of these silica and montmorillonite clay are of particular interest.

Alkyl: The term "alkyl", as used herein, pertains to a monovalent moiety obtained by removing a hydrogen atom from a carbon atom of a hydrocarbon having from 1 to 20 carbon atoms (unless otherwise specified), which may be aliphatic or alicyclic and which may be saturated or unsaturated (e.g. partially saturated, fully unsaturated). Thus, the term "alkyl" includes the sub-classes alkenyl, alkynyl, cycloalkyl, cycloalkenyl, cycloalkynyl, etc., as discussed below.

Alkylene: The term "alkylene", as used herein, pertains to a divalent moiety obtained by removing two hydrogen atoms from one or two carbon atoms of a hydrocarbon having from 1 to 20 carbon atoms (unless otherwise specified), which may be aliphatic or alicyclic and which may be saturated or unsaturated (e.g. partially saturated, fully unsaturated). Thus, the term "alkylene" includes the sub-classes alkenylene, alkynylene, cycloalkylene, cycloalkenylene, cycloalkynylene, etc., as discussed below.

In the context of alkyl and alkylene groups, the prefixes (e.g. $C_{1-4}$, $C_{1-7}$, $C_{1-20}$, $C_{2-7}$, $C_{3-7}$, etc.) denote the number of carbon atoms, or the range of number of carbon atoms. For example, the term "$C_{1-4}$ alkyl", as used herein, pertains to an alkyl group having from 1 to 4 carbon atoms. Examples of groups of alkyl groups include $C_{1-4}$ alkyl ("lower alkyl"), $C_{1-7}$ alkyl and $C_{1-20}$ alkyl. Note that the first prefix may vary according to other limitations; for example, for unsaturated alkyl groups, the first prefix must be at least 2; for cyclic alkyl groups, the first prefix must be at least 3; etc. For example, the term "$C_{1-7}$ alkylene", as used herein, pertains to an alkylene group having from 1 to 7 carbon atoms.

Examples of (unsubstituted) saturated alkyl groups include, but are not limited to, methyl ($C_1$), ethyl ($C_2$), propyl ($C_3$), butyl ($C_4$), pentyl ($C_5$), hexyl ($C_6$), and heptyl ($C_7$).

Examples of (unsubstituted) saturated linear alkyl groups include, but are not limited to, methyl ($C_1$), ethyl ($C_2$), n-propyl ($C_3$), n-butyl ($C_4$), n-pentyl (amyl) ($C_5$), n-hexyl ($C_6$), and n-heptyl ($C_7$).

Examples of (unsubstituted) saturated branched alkyl groups include iso-propyl ($C_3$), iso-butyl ($C_4$), sec-butyl ($C_4$), tert-butyl ($C_4$), iso-pentyl ($C_5$), and neo-pentyl ($C_5$).

Examples of (unsubstituted) saturated alkylene groups include, but are not limited to, methylene ($C_1$), ethylene ($C_2$), propylene ($C_3$), butylene ($C_4$), pentylene ($C_5$), hexylene ($C_6$), and heptylene ($C_7$).

Examples of (unsubstituted) saturated linear alkylene groups include, but are not limited to, methylene ($C_1$), ethylene ($C_2$), n-propylene ($C_3$), n-butylene ($C_4$), n-pentylene (amylene) ($C_5$), n-hexylene ($C_6$), and n-heptylene ($C_7$).

Examples of (unsubstituted) saturated branched alkyl groups include iso-propylene ($C_3$), iso-butylene ($C_4$), sec-butylene ($C_4$), tert-butylene ($C_4$), iso-pentylene ($C_5$), and neo-pentylene ($C_5$).

Alkenyl: The term "alkenyl", as used herein, pertains to an alkyl group having one or more carbon-carbon double bonds. Examples of groups of alkenyl groups include $C_{2-4}$ alkenyl, $C_{2-7}$ alkenyl, $C_{2-20}$ alkenyl.

Examples of (unsubstituted) unsaturated alkenyl groups include, but are not limited to, ethenyl (vinyl, —CH=CH$_2$), 1-propenyl (—CH=CH—CH$_3$), 2-propenyl (allyl, —CH$_2$—CH=CH$_2$), isopropenyl (1-methylvinyl, —C(CH$_3$)=CH$_2$), butenyl ($C_4$), pentenyl ($C_5$), and hexenyl ($C_6$).

Alkenylene: The term "alkenylene", as used herein, pertains to an alkylene group having one or more carbon-carbon double bonds. Examples of groups of alkenylene groups include $C_{2-4}$ alkenylene, $C_{2-7}$ alkenylene, $C_{2-20}$ alkenylene.

Alkynyl: The term "alkynyl", as used herein, pertains to an alkyl group having one or more carbon-carbon triple bonds. Examples of groups of alkynyl groups include $C_{2-4}$ alkynyl, $C_{2-7}$ alkynyl, $C_{2-20}$ alkynyl.

Examples of (unsubstituted) unsaturated alkynyl groups include, but are not limited to, ethynyl (ethinyl, —C≡CH) and 2-propynyl (propargyl, —CH$_2$—C≡CH).

Alkynylene: The term "alkynyl", as used herein, pertains to an alkylene group having one or more carbon-carbon triple bonds. Examples of groups of alkynylene groups include $C_{2-4}$ alkynylene, $C_{2-7}$ alkynylene, $C_{2-20}$ alkynylene.

Cycloalkyl: The term "cycloalkyl", as used herein, pertains to an alkyl group which is also a cyclyl group; that is, a monovalent moiety obtained by removing a hydrogen atom from an alicyclic ring atom of a carbocyclic ring of a carbocyclic compound, which carbocyclic ring may be saturated or unsaturated (e.g. partially unsaturated, fully unsaturated), which moiety has from 3-20 carbon atoms (unless otherwise specified), including from 3 to 20 ring atoms. Thus, the term "cycloalkyl" includes the sub-classes cycloalkenyl and cycloalkynyl. Preferably, each ring has from 3 to 7 ring atoms. Examples of groups of cycloalkyl groups include $C_{3-20}$ cycloalkyl, $C_{3-15}$ cycloalkyl, $C_{3-10}$ cycloalkyl, $C_{3-7}$ cycloalkyl.

Cycloalkylene: The term "cycloalkylene", as used herein, pertains to an alkylene group which is also a cyclyl group; that is, a divalent moiety obtained by removing two hydrogen atoms from one or two alicyclic ring atoms of a carbocyclic ring of a carbocyclic compound, which carbocyclic ring may be saturated or unsaturated (e.g. partially unsaturated, fully unsaturated), which moiety has from 3-20 carbon atoms (unless otherwise specified), including from 3 to 20 ring atoms. Thus, the term "cycloalkylene" includes the sub-classes cycloalkenylene and cycloalkynylene. Preferably, each ring has from 3 to 7 ring atoms. Examples of groups of cycloalkylene groups include $C_{3-20}$ cycloalkylene, $C_{3-15}$ cycloalkylene, $C_{3-10}$ cycloalkylene, $C_{3-7}$ cycloalkylene.

Cyclic alkylene: The term "cyclic alkylene" as used herein pertains to a divalent moiety obtained by removing a hydrogen atom from each of two adjacent alicyclic ring atoms of a carbocyclic ring of a carbocyclic compound, which carbocyclic ring may be saturated or unsaturated (e.g. partially saturated, fully unsaturated), which moiety has from 3 to 20 carbon atoms (unless otherwise specified), including from 3 to 20 ring atoms. Preferably each ring has from 5 to 7 ring atoms. Examples of groups of cyclic alkylene groups include $C_{3-20}$ cyclic alkylenes, $C_{3-15}$ cyclic alkylenes, $C_{3-10}$ cyclic alkylenes, $C_{3-7}$ cyclic alkylenes.

Examples of cycloalkyl groups and cyclic alkylene groups include, but are not limited to, those derived from:

saturated monocyclic hydrocarbon compounds:
cyclopropane ($C_3$), cyclobutane ($C_4$), cyclopentane ($C_5$), cyclohexane ($C_6$), cycloheptane ($C_7$), methylcyclopropane ($C_4$), dimethylcyclopropane ($C_5$), methylcyclobutane ($C_5$), dimethylcyclobutane ($C_6$), methylcyclopentane ($C_6$), dimethylcyclopentane ($C_7$), methylcyclohexane ($C_7$), dimethylcyclohexane ($C_8$), menthane ($C_{10}$);

unsaturated monocyclic hydrocarbon compounds:
cyclopropene ($C_3$), cyclobutene ($C_4$), cyclopentene ($C_5$), cyclohexene ($C_6$), methylcyclopropene ($C_4$), dimethylcyclopropene ($C_5$), methylcyclobutene ($C_5$), dimethylcyclobutene ($C_6$), methylcyclopentene ($C_6$), dimethylcyclopentene ($C_7$), methylcyclohexene ($C_7$), dimethylcyclohexene ($C_8$);

saturated polycyclic hydrocarbon compounds:
thujane ($C_{10}$), carane ($C_{10}$), pinane ($C_{10}$), bornane ($C_{10}$), norcarane ($C_7$), norpinane ($C_7$), norbornane ($C_7$), adamantane ($C_{10}$), decalin (decahydronaphthalene) ($C_{10}$);

unsaturated polycyclic hydrocarbon compounds:
camphene ($C_{10}$), limonene ($C_{10}$), pinene ($C_{10}$);

polycyclic hydrocarbon compounds having an aromatic ring:
indene ($C_9$), indane (e.g., 2,3-dihydro-1H-indene) ($C_9$), tetralin (1,2,3,4-tetrahydronaphthalene) ($C_{10}$), acenaphthene ($C_{12}$), fluorene ($C_{13}$), phenalene ($C_{13}$), acephenanthrene ($C_{15}$), aceanthrene ($C_{16}$), cholanthrene ($C_{20}$).

Heterocyclyl: The term "heterocyclyl", as used herein, pertains to a monovalent moiety obtained by removing a hydrogen atom from a ring atom of a heterocyclic compound, which moiety has from 3 to 20 ring atoms (unless otherwise specified), of which from 1 to 10 are ring heteroatoms. Preferably, each ring has from 3 to 7 ring atoms, of which from 1 to 4 are ring heteroatoms.

Heterocyclylene: The term "heterocyclylene", as used herein, pertains to a divalent moiety obtained by removing a hydrogen atom from each of two adjacent ring atoms of a heterocyclic compound, which moiety has from 3 to 20 ring atoms (unless otherwise specified), of which from 1 to 10 are ring heteroatoms. Preferably, each ring has from 3 to 7 ring atoms, of which from 1 to 4 are ring heteroatoms.

The heterocyclyl or heterocyclylene group may be bonded via carbon or hetero ring atoms. Preferably, the heterocyclylene group is bonded via two carbon atoms.

When referring to heterocyclyl or heterocyclylene groups, the prefixes (e.g. $C_{3-20}$, $C_{3-7}$, $C_{5-6}$, etc.) denote the number of ring atoms, or range of number of ring atoms, whether carbon atoms or heteroatoms. For example, the term "$C_{5-6}$ heterocyclyl", as used herein, pertains to a heterocyclyl group having 5 or 6 ring atoms. Examples of groups of heterocyclyl groups include $C_{3-20}$ heterocyclyl, $C_{5-20}$ heterocyclyl, $C_{3-15}$ heterocyclyl, $C_{5-15}$ heterocyclyl, $C_{3-12}$ heterocyclyl, $C_{5-12}$ heterocyclyl, $C_{3-10}$ heterocyclyl, $C_{5-10}$ heterocyclyl, $C_{3-7}$ heterocyclyl, $C_{5-7}$ heterocyclyl, and $C_{5-6}$ heterocyclyl.

Similarly, the term "$C_{5-6}$ heterocyclylene", as used herein, pertains to a heterocyclylene group having 5 or 6 ring atoms. Examples of groups of heterocyclylene groups include $C_{3-20}$ heterocyclylene, $C_{5-20}$ heterocyclylene, $C_{3-15}$ heterocyclylene, $C_{5-15}$ heterocyclylene, $C_{3-12}$ heterocyclylene, $C_{5-12}$ heterocyclylene, $C_{3-10}$ heterocyclylene, $C_{5-10}$ heterocyclylene, $C_{3-7}$ heterocyclylene, $C_{5-7}$ heterocyclylene, and $C_{5-6}$ heterocyclylene.

Examples of monocyclic heterocyclyl and heterocyclylene groups include, but are not limited to, those derived from:

$N_1$: aziridine ($C_3$), azetidine ($C_4$), pyrrolidine (tetrahydropyrrole) ($C_5$), pyrroline (e.g., 3-pyrroline, 2,5-dihydropyrrole) ($C_5$), 2H-pyrrole or 3H-pyrrole (isopyrrole, isoazole) ($C_5$), piperidine ($C_6$), dihydropyridine ($C_6$), tetrahydropyridine ($C_6$), azepine ($C_7$);

$O_1$: oxirane ($C_3$), oxetane ($C_4$), oxolane (tetrahydrofuran) ($C_5$), oxole (dihydrofuran) ($C_5$), oxane (tetrahydropyran) ($C_6$), dihydropyran ($C_6$), pyran ($C_6$), oxepin ($C_7$);

$S_1$: thiirane ($C_3$), thietane ($C_4$), thiolane (tetrahydrothiophene) ($C_5$), thiane (tetrahydrothiopyran) ($C_6$), thiepane ($C_7$);

$O_2$: dioxolane ($C_5$), dioxane ($C_6$), and dioxepane ($C_7$);

$O_3$: trioxane ($C_6$);

$N_2$: imidazolidine ($C_5$), pyrazolidine (diazolidine) ($C_5$), imidazoline ($C_5$), pyrazoline (dihydropyrazole) ($C_5$), piperazine ($C_6$);

$N_1O_1$: tetrahydrooxazole ($C_5$), dihydrooxazole ($C_5$), tetrahydroisoxazole ($C_5$), dihydroisoxazole ($C_5$), morpholine ($C_6$), tetrahydrooxazine ($C_6$), dihydrooxazine ($C_6$), oxazine ($C_6$);

$N_1S_1$: thiazoline ($C_5$), thiazolidine ($C_5$), thiomorpholine ($C_6$);

$N_2O_1$: oxadiazine ($C_6$);

$O_1S_1$: oxathiole ($C_5$) and oxathiane (thioxane) ($C_6$); and, $N_1O_1S_1$: oxathiazine ($C_6$).

Examples of substituted (non-aromatic) monocyclic heterocyclyl and heterocyclylene groups include those derived from saccharides, in cyclic form, for example, furanoses ($C_5$), such as arabinofuranose, lyxofuranose, ribofuranose, and xylofuranse, and pyranoses ($C_6$), such as allopyranose, altropyranose, glucopyranose, mannopyranose, gulopyranose, idopyranose, galactopyranose, and talopyranose.

$C_{5-20}$ aryl: The term "$C_{5-20}$ aryl", as used herein, pertains to a monovalent moiety obtained by removing a hydrogen atom from an aromatic ring atom of a $C_{5-20}$ aromatic compound, said compound having one ring, or two or more rings (e.g., fused), and having from 5 to 20 ring atoms, and wherein at least one of said ring(s) is an aromatic ring. Preferably, each ring has from 5 to 7 carbon atoms.

The ring atoms may be all carbon atoms, as in "carboaryl groups" in which case the group may conveniently be referred to as a "$C_{5-20}$ carboaryl" group.

$C_{5-20}$ arylene: The term "$C_{5-20}$ arylene", as used herein, pertains to a divalent moiety obtained by removing a hydrogen atom from each of two adjacent ring atoms of a $C_{5-20}$ aromatic compound, said compound having one ring, or two or more rings (e.g., fused), and having from 5 to 20 ring atoms, and wherein at least one of said ring(s) is an aromatic ring. Preferably, each ring has from 5 to 7 carbon atoms.

The ring atoms may be all carbon atoms, as in "carboarylene groups" in which case the group may conveniently be referred to as a "$C_{5-20}$ carboarylene" group.

Examples of $C_{5-20}$ aryl and $C_{5-20}$ arylene groups which do not have ring heteroatoms (i.e. $C_{5-20}$ carboaryl and $C_{5-20}$ carboarylene groups) include, but are not limited to, those derived from benzene (i.e. phenyl) ($C_6$), naphthalene ($C_{10}$), anthracene ($C_{14}$), phenanthrene ($C_{14}$), and pyrene ($C_{16}$).

Alternatively, the ring atoms may include one or more heteroatoms, including but not limited to oxygen, nitrogen, and sulfur, as in "heteroaryl groups" or "heteroarylene groups". In this case, the group may conveniently be referred to as a "$C_{5-20}$ heteroaryl" or "$C_{5-20}$ heteroarylene" group, wherein "$C_{5-20}$" denotes ring atoms, whether carbon atoms or heteroatoms. Preferably, each ring has from 5 to 7 ring atoms, of which from 0 to 4 are ring heteroatoms.

The heteroaryl or heteroarylene group may be bonded via carbon or hetero ring atoms. Preferably, the heteroarylene group is bonded via two carbon atoms.

Examples of $C_{5-20}$ heteroaryl and $C_{5-20}$ heteroarylene groups include, but are not limited to, $C_5$ heteroaryl and $C_5$ heteroarylene groups derived from furan (oxole), thiophene (thiole), pyrrole (azole), imidazole (1,3-diazole), pyrazole (1,2-diazole), triazole, oxazole, isoxazole, thiazole, isothiazole, oxadiazole, tetrazole and oxatriazole; and $C_6$ heteroaryl groups derived from isoxazine, pyridine (azine), pyridazine (1,2-diazine), pyrimidine (1,3-diazine; e.g., cytosine, thymine, uracil), pyrazine (1,4-diazine) and triazine.

Examples of $C_{5-20}$ heteroaryl and $C_{5-20}$ heteroarylene groups which comprise fused rings, include, but are not limited to, $C_9$ heteroaryl and $C_9$ heteroarylene groups derived from benzofuran, isobenzofuran, benzothiophene, indole, isoindole; $C_{10}$ heteroaryl and $C_{10}$ heteroarylene groups derived from quinoline, isoquinoline, benzodiazine, pyridopyridine; $C_{14}$ heteroaryl and $C_{14}$ heteroarylene groups derived from acridine and xanthene.

Bisoxy$C_{1-3}$ alkylene: —O—$(CH_2)_m$—O—, where m is 1 to 3.

The above alkyl, alkylene, cyclic alkylene, bisoxyalkylene, heterocyclyl, heterocyclylene, aryl, and arylene groups, whether alone or part of another substituent, may themselves optionally be substituted with one or more groups selected from themselves and the additional substituents listed below.

Halo: —F, —Cl, —Br, and —I.

Hydroxy: —OH.

Ether: —OR, wherein R is an ether substituent, for example, a $C_{1-7}$ alkyl group (also referred to as a $C_{1-7}$ alkoxy group), a $C_{3-20}$ heterocyclyl group (also referred to as a $C_{3-20}$ heterocyclyloxy group), or a $C_{5-20}$ aryl group (also referred to as a $C_{5-20}$ aryloxy group), preferably a $C_{1-7}$ alkyl group.

Nitro: —$NO_2$.

Cyano (nitrile, carbonitrile): —CN.

Acyl (keto): —C(=O)R, wherein R is an acyl substituent, for example, H, a $C_{1-7}$ alkyl group (also referred to as $C_{1-7}$ alkylacyl or $C_{1-7}$ alkanoyl), a $C_{3-20}$ heterocyclyl group (also referred to as $C_{3-20}$ heterocyclylacyl), or a $C_{5-20}$ aryl group (also referred to as $C_{5-20}$ arylacyl), preferably a $C_{1-7}$ alkyl group. Examples of acyl groups include, but are not limited to, —C(=O)CH$_3$ (acetyl), —C(=O)CH$_2$CH$_3$ (propionyl), —C(=O)C(CH$_3$)$_3$ (pivaloyl), and —C(=O)Ph (benzoyl, phenone).

Carboxy (carboxylic acid): —COOH.

Ester (carboxylate, carboxylic acid ester, oxycarbonyl): —C(=O)OR, wherein R is an ester substituent, for example, a $C_{1-7}$ alkyl group, a $C_{3-20}$ heterocyclyl group, or a $C_{5-20}$ aryl group, preferably a $C_{1-7}$ alkyl group. Examples of ester groups include, but are not limited to, —C(=O)OCH$_3$, —C(=O)OCH$_2$CH$_3$, —C(=O)OC(CH$_3$)$_3$, and —C(=O)OPh.

Amido (carbamoyl, carbamyl, aminocarbonyl, carboxamide): —C(=O)NR$^1$R$^2$, wherein R$^1$ and R$^2$ are independently amino substituents, as defined for amino groups. Examples of amido groups include, but are not limited to, —C(=O)NH$_2$, —C(=O)NHCH$_3$, —C(=O)N(CH$_3$)$_2$, —C(=O)NHCH$_2$CH$_3$, and —C(=O)N(CH$_2$CH$_3$)$_2$, as well as amido groups in which R$^1$ and R$^2$, together with the nitrogen atom to which they are attached, form a heterocyclic structure as in, for example, piperidinocarbonyl, morpholinocarbonyl, thiomorpholinocarbonyl, and piperazinylcarbonyl.

Amino: —NR$^1$R$^2$, wherein R$^1$ and R$^2$ are independently amino substituents, for example, hydrogen, a $C_{1-7}$ alkyl group (also referred to as $C_{1-7}$ alkylamino or di-$C_{1-7}$ alkylamino), a $C_{3-20}$ heterocyclyl group, or a $C_{5-20}$ aryl group, preferably H or a $C_{1-7}$ alkyl group, or, in the case of a "cyclic" amino group, R$^1$ and R$^2$, taken together with the nitrogen atom to which they are attached, form a heterocyclic ring having from 4 to 8 ring atoms. Examples of amino groups include, but are not limited to, —NH$_2$, —NHCH$_3$, —NHCH(CH$_3$)$_2$, —N(CH$_3$)$_2$, —N(CH$_2$CH$_3$)$_2$, and —NHPh. Examples of cyclic amino groups include, but are not limited to, aziridinyl, azetidinyl, pyrrolidinyl, piperidino, piperazinyl, perhydrodiazepinyl, morpholino, and thiomorpholino. In particular, the cyclic amino groups may be substituted on their ring by any of the substituents defined here, for example carboxy, carboxylate and amido.

Ammonium: —NR$^{N1}$R$^{N2}$R$^{N3}$, wherein R$^{N1}$, R$^{N2}$ and R$^{N3}$ are independently ammonium substituents, for example, a $C_{1-7}$ alkyl group, a $C_{3-20}$ heterocyclyl group, or a $C_{5-20}$ aryl group and where one or two of R$^{N1}$, R$^{N2}$ and R$^{N3}$ may also be H. One of R$^{N1}$, R$^{N2}$ and R$^{N3}$ may be a $C_{1-3}$ alkoxy (—(CH$_2$)$_{1-3}$—OH)group. Two or three of the ammonium substituents may join together to form cyclic or cage-like structures. Examples of ammonium groups include, but are not limited to, —NH(CH$_3$)$_2$, —NH(CH(CH$_3$)$_2$)$_2$, —N(CH$_3$)$_3$, —N(CH$_2$CH$_3$)$_3$, and —NH$_2$Ph.

Ammonium linking group: —NR$^{N1}$R$^{N2}$R$^{N4}$—, wherein R$^{N1}$ and R$^{N2}$ are independently ammonium substituents, for example, a $C_{1-7}$ alkyl group, a $C_{3-20}$ heterocyclyl group, or a $C_{5-20}$ aryl group and where one or both of R$^{N1}$ and R$^{N2}$ may also be H. The two ammonium substituents may join together to form a cyclic structure. R$^{N4}$ is a divalent ammonium substituent, for example, a $C_{1-7}$ alkylene group, a $C_{3-20}$ heterocyclylene group, or a $C_{5-20}$ arylene group or a divalent $C_{1-3}$ alkyloxylene (—(CH$_2$)$_{1-3}$—O—) group. Examples of ammonium linking groups include, but are not limited to, —NH(CH$_3$)(CH$_2$)—, —NH(CH(CH$_3$)$_2$)(C(CH$_3$)$_2$)—, —N(CH$_3$)$_2$(CH$_2$)—, —N(CH$_2$CH$_3$)$_2$(CH$_2$CH$_2$)—, and —NHPh(CH$_2$)—.

Acylamido (acylamino): —NR$^1$C(=O)R$^2$, wherein R$^1$ is an amide substituent, for example, hydrogen, a $C_{1-7}$ alkyl group, a $C_{3-20}$ heterocyclyl group, or a $C_{5-20}$ aryl group, preferably H or a $C_{1-7}$ alkyl group, most preferably H, and R$^2$ is an acyl substituent, for example, a $C_{1-7}$ alkyl group, a $C_{3-20}$ heterocyclyl group, or a $C_{5-20}$ aryl group, preferably a $C_{1-7}$ alkyl group. Examples of acylamide groups include, but are not limited to, —NHC(=O)CH$_3$, —NHC(=O)CH$_2$CH$_3$, and —NHC(=O)Ph. R$^1$ and R$^2$ may together form a cyclic structure, as in, for example, succinimidyl, maleimidyl, and phthalimidyl:

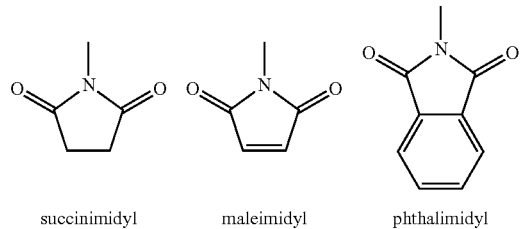

succinimidyl   maleimidyl   phthalimidyl

Ureido: —N(R$^1$)CONR$^2$R$^3$ wherein R$^2$ and R$^3$ are independently amino substituents, as defined for amino groups, and R$^1$ is a ureido substituent, for example, hydrogen, a $C_{1-7}$alkyl group, a $C_{3-20}$heterocyclyl group, or a $C_{5-20}$aryl group, preferably hydrogen or a $C_{1-7}$alkyl group. Examples of ureido groups include, but are not limited to, —NHCONH$_2$, —NHCONHMe, —NHCONHEt, —NHCONMe$_2$, —NHCONEt$_2$, —NMeCONH$_2$, —NMeCONHMe, —NMeCONHEt, —NMeCONMe$_2$, —NMeCONEt$_2$ and —NHCONHPh.

Acyloxy (reverse ester): —OC(=O)R, wherein R is an acyloxy substituent, for example, a $C_{1-7}$ alkyl group, a $C_{3-20}$ heterocyclyl group, or a $C_{5-20}$ aryl group, preferably a $C_{1-7}$ alkyl group. Examples of acyloxy groups include, but are not limited to, —OC(=O)CH$_3$ (acetoxy), —OC(=O)CH$_2$CH$_3$, —OC(=O)C(CH$_3$)$_3$, —OC(=O)Ph, —OC(=O)C$_6$H$_4$F, and —OC(=O)CH$_2$Ph.

Thiol: —SH.

Thioether (sulfide): —SR, wherein R is a thioether substituent, for example, a $C_{1-7}$ alkyl group (also referred to as a $C_{1-7}$ alkylthio group), a $C_{3-20}$ heterocyclyl group, or a $C_{5-20}$ aryl group, preferably a $C_{1-7}$ alkyl group. Examples of $C_{1-7}$ alkylthio groups include, but are not limited to, —SCH$_3$ and —SCH$_2$CH$_3$.

Sulfoxide (sulfinyl): —S(=O)R, wherein R is a sulfoxide substituent, for example, a $C_{1-7}$ alkyl group, a $C_{3-20}$ heterocyclyl group, or a $C_{5-20}$ aryl group, preferably a $C_{1-7}$ alkyl group. Examples of sulfoxide groups include, but are not limited to, —S(=O)CH$_3$ and —S(=O)CH$_2$CH$_3$.

Sulfonyl (sulfone): —S(=O)$_2$R, wherein R is a sulfone substituent, for example, a $C_{1-7}$ alkyl group, a $C_{3-20}$ heterocyclyl group, or a $C_{5-20}$ aryl group, preferably a $C_{1-7}$ alkyl group. Examples of sulfone groups include, but are not limited to, —S(=O)$_2$CH$_3$ (methanesulfonyl, mesyl), —S(=O)$_2$CF$_3$, —S(=O)$_2$CH$_2$CH$_3$, and 4-methylphenylsulfonyl (tosyl).

Thioamido (thiocarbamyl): —C(=S)NR$^1$R$^2$, wherein R$^1$ and R$^2$ are independently amino substituents, as defined for amino groups. Examples of amido groups include, but are not limited to, —C(=S)NH$_2$, —C(=S)NHCH$_3$, —C(=S)N(CH$_3$)$_2$, and —C(=S)NHCH$_2$CH$_3$.

Sulfonamino: —NR$^1$S(=O)$_2$R, wherein R$^1$ is an amino substituent, as defined for amino groups, and R is a sulfonamino substituent, for example, a $C_{1-7}$alkyl group, a $C_{3-20}$heterocyclyl group, or a $C_{5-20}$aryl group, preferably a $C_{1-7}$alkyl group. Examples of sulfonamino groups include, but are not limited to, —NHS(=O)$_2$CH$_3$, —NHS(=O)$_2$Ph and —N(CH$_3$)S(=O)$_2$C$_6$H$_5$.

As mentioned above, the groups that form the above listed substituent groups, e.g. $C_{1-7}$ alkyl, $C_{3-20}$ heterocyclyl and $C_{5-20}$ aryl, may themselves be substituted. Thus, the above definitions cover substituent groups which are substituted.

$C_{1-3}$ alkylene: —(CH$_2$)$_m$—, where m is 1 to 3.

Chemically Protected Forms

It may be convenient or desirable to prepare, purify, handle and/or use the active compound in a chemically protected form. The term "chemically protected form" is used herein in the conventional chemical sense and pertains to a compound in which one or more reactive functional groups are protected from undesirable chemical reactions under specified conditions (e.g., pH, temperature, radiation, solvent, and the like). In practice, well known chemical methods are employed to reversibly render unreactive a functional group, which otherwise would be reactive, under specified conditions. In a chemically protected form, one or more reactive functional groups are in the form of a protected or protecting group (also known as a masked or masking group or a blocked or blocking group). By protecting a reactive functional group, reactions involving other unprotected reactive functional groups can be performed, without affecting the protected group; the protecting group may be removed, usually in a subsequent step, without substantially affecting the remainder of the molecule. See, for example, *Protective Groups in Organic Synthesis* (T. Green and P. Wuts; 3rd Edition; John Wiley and Sons, 1999).

Unless otherwise specified, a reference to a particular compound also includes chemically protected forms thereof.

A wide variety of such "protecting," "blocking," or "masking" methods are widely used and well known in organic synthesis. For example, a compound which has two non-equivalent reactive functional groups, both of which would be reactive under specified conditions, may be derivatized to render one of the functional groups "protected," and therefore unreactive, under the specified conditions; so protected, the compound may be used as a reactant which has effectively only one reactive functional group. After the desired reaction (involving the other functional group) is complete, the protected group may be "deprotected" to return it to its original functionality.

For example, a hydroxy group may be protected as an ether (—OR) or an ester (—OC(=O)R), for example, as: a t-butyl ether; a benzyl, benzhydryl (diphenylmethyl), or trityl (triphenylmethyl)ether; a trimethylsilyl or t-butyldimethylsilyl ether; or an acetyl ester (—OC(=O)CH$_3$, —OAc).

For example, an aldehyde or ketone group may be protected as an acetal (R—CH(OR)$_2$) or ketal (R$_2$C(OR)$_2$), respectively, in which the carbonyl group (>C=O) is converted to a diether (>C(OR)$_2$), by reaction with, for example, a primary alcohol. The aldehyde or ketone group is readily regenerated by hydrolysis using a large excess of water in the presence of acid.

For example, an amine group may be protected, for example, as an amide (—NRCO—R) or a urethane (—NRCO—OR), for example, as: a methyl amide (—NHCO—CH$_3$); a benzyloxy amide (—NHCO—OCH$_2$C$_6$H$_5$, —NH-Cbz); as a t-butoxy amide (—NHCO—OC(CH$_3$)$_3$, —NH-Boc); a 2-biphenyl-2-propoxy amide (—NHCO—OC(CH$_3$)$_2$C$_6$H$_4$C$_6$H$_5$, —NH-Bpoc), as a 9-fluorenylmethoxy amide (—NH-Fmoc), as a 6-nitroveratrylmethoxy amide (—NH-Nvoc), as a 2-trimethylsilylethyloxy amide (—NH-Teoc), as a 2,2,2-trichloroethyloxy amide (—NH-Troc), as an allyloxy amide (—NH-Alloc), as a 2(-phenylsulphonyl)ethyloxy amide (—NH-Psec); or, in suitable cases (e.g., cyclic amines), as a nitroxide radical (>N—O.).

For example, a carboxylic acid group may be protected as an ester for example, as: a $C_{1-7}$alkyl ester (e.g., a methyl ester; a t-butyl ester); a $C_{1-7}$haloalkyl ester (e.g., a $C_{1-7}$trihaloalkyl ester); a triC$_{1-7}$alkylsilyl-C$_{1-7}$alkyl ester; or a $C_{5-20}$aryl-C$_{1-7}$alkyl ester (e.g., a benzyl ester; a nitrobenzyl ester); or as an amide, for example, as a methyl amide.

For example, a thiol group may be protected as a thioether (—SR), for example, as: a benzyl thioether; an acetamidomethyl ether (—S—CH$_2$NHC(=O)CH$_3$).

In particular application in a disclosed embodiment is the protection of hydroxy and amino groups.

Catalysed Reactions

In one aspect of a disclosed embodiment, there is provided a process for the production of cyclic carbonates comprising contacting an epoxide with carbon dioxide in the presence of a dimeric aluminium(salen) catalyst of formula I.

This reaction has the advantage that it may be carried out at easily accessible temperatures of between 0 and 40° C. and pressures of between 0.5 and 2 atm. The reaction may even be carried out at temperatures of between 0 and 140° C. and pressures of between 0.5 and 5 atm. Preferably, the reaction temperature lies between 20 and 30° C. Yields of over 50% may be achieved with short reaction times of 3 to 24 hours, using commercially viable amounts of catalyst, that is, from 0.1 to 10 mol %, preferably 0.1 to 2.5 mol %. In some cases, yields of over 70% or over 90% may be achieved under these conditions.

The reaction may also be carried out in a flow reactor, wherein the reaction is continuous.

In some embodiments, the carbon dioxide may be supplied heated, and in other embodiments, the reaction may be heated by a conventional or microwave system.

Catalysts

The embodiments and preferences expressed below may be combined with one another, where appropriate.

In some aspects of a disclosed embodiment, L is selected from a single bond and $C_{1-7}$ alkylene.

In some aspects of a disclosed embodiment, the aluminium (salen) catalyst of formula I is symmetrical, such that $X^1=X^2$, $R^1=R^{13}$, $R^2=R^{14}$, $R^3=R^{15}$, $R^4=R^{16}$, $R^5=R^9$, $R^6=R^{10}$, $R^7=R^{11}$, and $R^8=R^{12}$. More preferably $R^1$, $R^5$, $R^9$, and $R^{13}$ are identical, $R^2$, $R^6$, $R^{10}$ and $R^{14}$ are identical, $R^3$, $R^7$, $R^{11}$, and $R^{15}$ are identical, and $R^4$, $R^8$, $R^{12}$ and $R^{16}$ are identical. Such catalysts are of formula Ia, which may be preferred.

If the catalyst is bound to a solid support, then it will not be fully symmetrical.

In some embodiments, $X^1$ and $X^2$ are the same.

In some embodiments, $X^1$ and $X^2$ are independently selected from a $C_{2-5}$ alkylene chain, which is preferably unsubstituted, and a $C_{1-3}$ bisoxylakylene chain, which is preferably unsubstituted. These groups can be represented as —(CH$_2$)$_n$— or —O—(CH$_2$)$_p$—O—, where n is 2, 3, 4, or 5 and p is 1, 2, or 3. In these embodiments, n is preferably 2 or 3 and p is preferably 1 or 2. n is more preferably 2. In these embodiments $X^1$ and $X^2$ are preferably selected from —(CH$_2$)$_n$— (e.g. —C$_2$H$_4$—).

In other embodiments, $X^1$ and $X^2$ independently represent a divalent group selected from $C_{5-7}$ arylene, $C_{5-7}$ cyclic alkylene and $C_{3-7}$ heterocyclylene, which may be optionally substituted. Preferably $X^1$ and $X^2$ independently represent $C_{5-7}$ cyclic alkylene, and more preferably $C_6$ cyclic alkylene. This group is preferably saturated, and therefore is the group:

In other preferred embodiments, $X^1$ and $X^2$ independently represent $C_{5-7}$ arylene, which is more preferably $C_6$ arylene, and in particular, benzylene:

When $X^1$ and $X^2$ independently represent a divalent group selected from $C_{5-7}$ arylene, $C_{5-7}$ cyclic alkylene and $C_{3-7}$ heterocyclylene, it may preferably be unsubstituted. If it is substituted, then the substituents may be selected from nitro, halo, $C_{1-4}$ alkyl, including substituted $C_{1-4}$ alkyl, (e.g. methyl, benzyl), $C_{1-4}$ alkoxy (e.g. methoxy) and hydroxy.

Preferably Y-Q is $CR^{C1}$=N, wherein $R^{C1}$ is as defined above. $R^{C1}$ is preferably selected from H and $C_{1-4}$ alkyl. More preferably Y-Q is CH=N.

If Y-Q is $CR^{C1}R^{C2}$—$NR^{N1}$, then in some embodiments $R^{C1}$, $R^{C2}$ and $R^{N1}$ are H Preferably $R^4$=$R^8$=$R^{12}$=$R^{16}$=H.

In some embodiments, $R^1$=$R^5$=$R^9$=$R^{13}$=H.

In some embodiments, it is one or more of $R^3$, $R^7$, $R^{11}$ and $R^{15}$ that is -L-A or L-A'. In some of these embodiments, if one of these groups is -L-A', the other groups are -L-A. Alternatively, the other groups may be -L-$A^M$, where $A^M$ is a tertiary amine group, i.e. an amino group where the amino substituents are both not hydrogen, for example, $C_{1-7}$ alkyl (ethyl). The L in all these groups may be the same.

Preferably those of $R^1$, $R^2$, $R^3$, $R^5$, $R^6$, $R^7$, $R^9$, $R^{10}$, $R^{11}$, $R^{13}$, $R^{14}$, $R^{15}$ and $R^{16}$ which do not comprise -L-A or -L-A' are independently selected from H, $C_{1-7}$ alkyl, ether and nitro.

If a group selected from $R^1$, $R^2$, $R^3$, $R^5$, $R^6$, $R^7$, $R^9$, $R^{10}$, $R^{11}$, $R^{13}$, $R^{14}$, $R^{15}$ and $R^{16}$ is ether, then the ether group is preferably a $C_{1-7}$ alkoxy group and more preferably $C_{1-4}$ alkoxy group, e.g. methoxy.

If a group selected from $R^1$, $R^2$, $R^3$, $R^5$, $R^6$, $R^7$, $R^9$, $R^{10}$, $R^{11}$, $R^{13}$, $R^{14}$, and $R^{15}$ is $C_{1-7}$ alkyl, it is preferably butyl, more preferably tert-butyl.

L is preferably unsubstituted.

L may preferably be a $C_{1-3}$ alkylene group, e.g. methylene, ethylene, propylene, and in some embodiments is methylene.

A may preferably be selected from ammonium groups where $R^{N1}$, $R^{N2}$ and $R^{N3}$ are independently selected from $C_{1-7}$ alkyl groups and $C_{5-20}$ aryl groups, and where one or two of $R^{N1}$, $R^{N2}$ and $R^{N3}$ may also be H. Ammonium groups of particular interest in a disclosed embodiment include, but are not limited to, —NH(CH$_3$)$_2$, —NH(CH(CH$_3$)$_2$)$_2$, —N(CH$_3$)$_3$, —N(CH$_2$CH$_3$)$_3$, and —NH$_2$Ph.

A' may preferably be selected from ammonium linking groups where $R^{N1}$ and $R^{N2}$ are independently selected from $C_{1-7}$ alkyl groups and $C_{5-20}$ aryl groups, where one or both of $R^{N1}$ and $R^{N2}$ may also be H and where $R^{N4}$ is a $C_{1-7}$ alkylene group. Ammonium linking groups of particular interest in a disclosed embodiment include, but are not limited to, —NH(CH$_3$)(CH$_2$)—, —NH(CH(CH$_3$)$_2$)(C(CH$_3$)$_2$)—, —N(CH$_3$)$_2$(CH$_2$)—, —N(CH$_2$CH$_3$)$_2$(CH$_2$CH$_2$)—, and —NHPh(CH$_2$)—.

In some embodiments, Q may be —C(=O)—O— or —C(=O)—NH—.

When $X^1$ and/or $X^2$ is substituted by -Q-L-A or -Q-L-A', it is preferably a $C_2$ or $C_3$ alkylene group, more preferably a $C_2$ alkylene group, and may be of the formula:

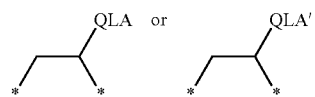

If $X^1$ or $X^2$ is a divalent $C_{3-7}$ heterocyclene group containing a ring atom which is a quaternary nitrogen atom, then it is preferably of the formula:

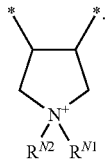

If $X^1$ or $X^2$ is a divalent $C_{3-7}$ heterocyclene group containing a ring atom which is a quaternary nitrogen forming part of an ammonium linking group, then it is preferably of the formula:

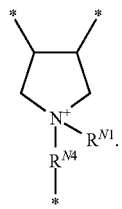

In some aspects of a disclosed embodiment, the catalyst is of formula Ib:

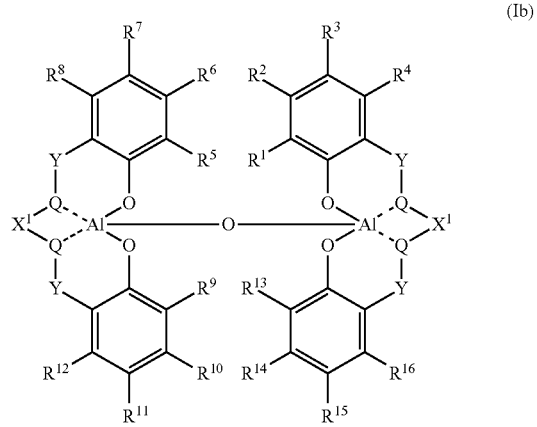

wherein:

Y-Q is $CR^{C1}$=N or $CR^{C1}R^{C2}$—$NR^{N1}$, where $R^{C1}$, $R^{C2}$ and $R^{N1}$ are independently selected from H, halo, optionally substituted $C_{1-20}$ alkyl, optionally substituted $C_{5-20}$ aryl, ether and nitro;

each of the substituents $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, and $R^{16}$, is independently selected from H, halo, optionally substituted $C_{1-20}$ alkyl (including $CAr_3$, where Ar is a $C_{5-20}$ aryl group), optionally substituted $C_{5-20}$ aryl, optionally substituted $C_{3-20}$ heterocyclyl, ether and nitro;

X is either of the formula —$(CH_2)_n$— or —O—$(CH_2)_p$—O—, where n is 2, 3, 4, or 5 and p is 1, 2, or 3, or represents a divalent group selected from $C_{5-7}$ arylene, $C_{5-7}$ cyclic alkylene and $C_{3-7}$ heterocyclylene, which may be optionally substituted;

at least one of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, and $R^{16}$ is selected from L-A, where L is a single bond or a $C_{1-7}$ alkylene group and A is an ammonium group paired with a counterion selected from Cl, Br and I;

and/or one of $R^1$, $R^2$, $R^3$, $R^4$, $R_5$, $R^6$, $R^7$, $R^8$, $R^9$, $R^{10}$, $R^{11}$, $R^{12}$, $R^{13}$, $R^{14}$, $R^{15}$, and $R^{16}$ is L-A', where L is as defined above and A' is a ammonium linking group bound to a solid support and paired with a counterion selected from Cl, Br and I.

The preferences expressed above also apply to the catalysts of formula Ib, where appropriate.

The reaction may be carried out under solvent-free conditions, depending on the epoxides used. In some cases, the epoxides or the cyclic carbonates may act as a solvent for the catalyst. In particular, the disclosed embodiments show that propylene carbonate acts a suitable reaction solvent.

Some reactions may need the addition of a co-catalyst, $Y^-$, and in particular MY, where M is a suitable cation, such as onium halides, which include, but are not limited to, $R_4NY$, $R_3SY$, $R_4PY$ and $R_4SbY$, where each R is independently selected from optionally substituted $C_{1-10}$ alkyl, $C_{3-20}$ heterocyclyl and $C_{5-20}$ aryl groups and one R can be an acyl group, and simple halides, e.g. NaCl, KI.

It is preferred that the co-catalyst for this reaction is of the form $R_4NY$, where each R is independently $C_{1-10}$ alkyl and Y is selected from I, Br and Cl. R is preferably selected from $C_{3-5}$ alkyl, and more preferably is butyl. Y is preferably Br. Therefore, a particularly preferred co-catalyst is $Bu_4NBr$ (TBAB). The amount of co-catalyst is preferably less than 2.5%, more preferably less than 1.0 mol % and most preferably less than 0.5 mol %. In some embodiments, no separate co-catalyst is present.

Manufacture of Dimeric Aluminium(Salen) Complexes

In a third aspect of a disclosed embodiment, there is provided a process for the production of dimeric aluminium (salen) catalysts of formula I.

When the catalyst of formula I comprises one or more ammonium group paired with a counterion, it may be synthesised from a precursor comprising the corresponding ammonia groups by reaction with a organic halide (i.e. a $C_{1-7}$ alkyl, $C_{3-20}$ heterocyclyl or $C_{5-20}$ aryl halide), or an organic group with another leaving group (e.g. tosylate).

When the catalyst of formula I comprises an ammonium linking group bound to a solid support, it may be synthesised from a precursor catalyst comprising a corresponding ammonia group by reaction with a halide derived solid support or a solid support derivatized with another leaving group (e.g. tosylate).

EXAMPLES

General Experimental Methods

IR spectroscopy

IR spectra of liquids or of solids dissolved in a solvent were recorded between NaCl plates on a PE Spectrum 1 spectrometer. IR spectra of pure solids were recorded on a Nicolet380 FTIR spectrometer fitted with a 'Smart orbit' attachment.

NMR

All NMR spectra were recorded at ambient temperature on a Bruker Avance 300 spectrometer. The sample was dissolved in $CDCl_3$ unless specified otherwise.

Mass Spectroscopy

Low resolution EI and CI spectra were recorded on a Varian Saturn 2200 GC-mass spectrometer. Low and high resolution electrospray spectra (ESI) were recorded on a Waters LCT Premier mass spectrometer.

Synthesis of Key Intermediates

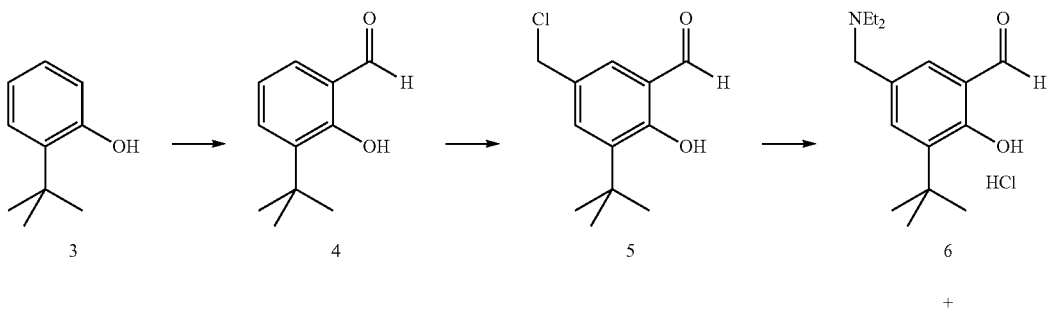

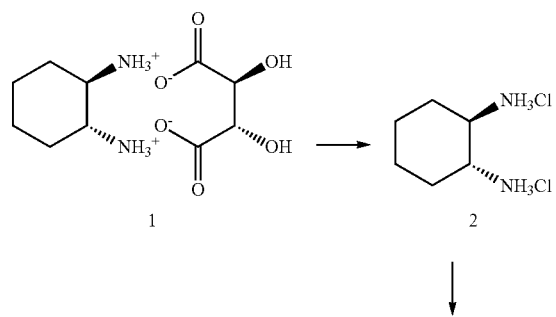

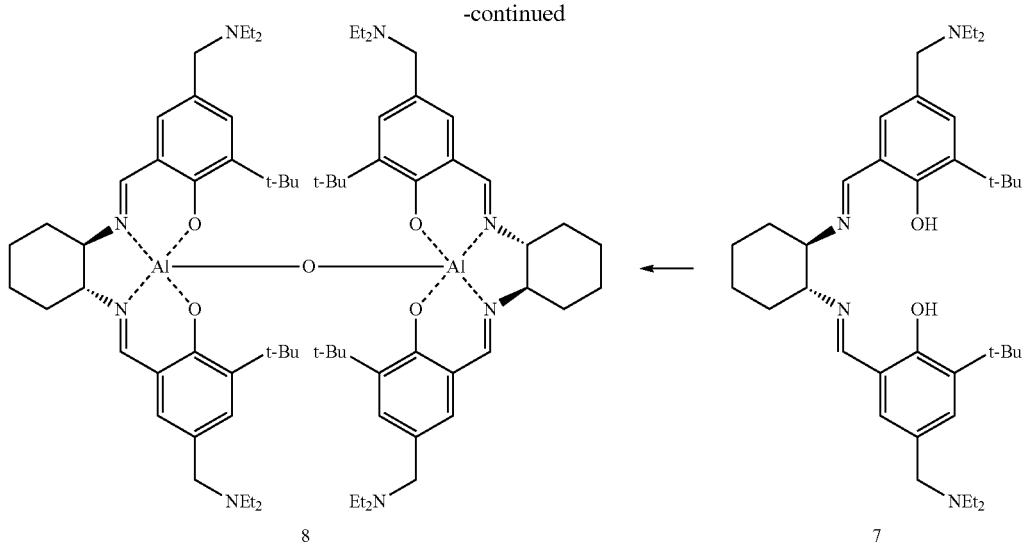

(a) (1R,2R)-Cyclohexane-1,2-diammonium dichloride (2)

(Larrow, J. F, et al., *J. Org. Chem.* 1994, 59, 193)

To a suspension of (1R,2R)-cyclohexane-1,2-diammonium L-tartrate (1)(13.7 g, 52 mmol) in MeOH (50 mL) was added a cooled solution (0° C.) of acetyl chloride (27.4 mL, 385 mmol) in MeOH (50 mL). The solution was stirred at room temperature overnight. The resulting precipitate was filtered off, washed with Et$_2$O (10 mL) and dried by suction to leave the desired product as a white powder. A second crop was obtained by diluting the mother liquor with Et$_2$O (200 mL) and cooling for half an hour. The product was collected and dried to yield a white powder. Yield: 80%. Crystalline white powder. $[\alpha]^{20}_D$-16 (c 5.0, aq. 1M HCl). $^1$H-NMR $\delta_H$ (DMSO-d$_6$): 1.05-1.25 (2H, m, CH$_2$CH$_2$CHN), 1.30-1.55 (2H, m, CH$_2$CH$_2$CHN), 1.60-1.75 (2H, m, CH$_2$CHN), 2.00-2.15 (2H, m, CH$_2$CHN), 3.13-3.30 (2H, m, CHN), 8.70 (6H, br s, NH$_3$).

(b) 3-tert-Butylsalicylaldehyde (4)

(Gisch, N.; Balzarini, J.; Meier, C. *J. Med. Chem.* 2007, 50, 1658)

To a stirred suspension of 2-tert-butylphenol (3)(4.55 g, 30 mmol), magnesium chloride (5.71 g, 60 mmol) and paraformaldehyde (2.08 g, 66 mmol) in THF (120 mL) at room temperature, was added triethylamine (8.35 mL, 60 mmol) dropwise. The reaction was heated to reflux for 3 hours to give an orange suspension. This was extracted using EtOAc (3×50 mL). A small amount of diluted HCl can be added if a permanent emulsion is formed. The organic layers were dried over MgSO$_4$ and the volatiles evaporated under low pressure to yield a pale yellow oil which did not need any further purification. It can become dark green on storage. Yield: 90%. Pale yellow oil. $^1$H-NMR $\delta_H$: 1.44 (9H, s, 3×CH$_3$), 6.97 (1H, t, J=7.5 Hz, H$_{Ar}$), 7.41 (1H, dd, J=1.5 Hz, J=7.5 Hz, H$_{Ar}$), 7.54 (1H, dd, J=1.2 Hz, J=7.5 Hz, H$_{Ar}$), 9.88 (1H, s, CHO), 11.82 (1H, s, OH).

(c) 3-tert-Butyl-5-chloromethylsalicylaldehyde (5)

A mixture of 3-tert-butylsalicylaldehyde (4)(3.56 g, 20 mmol) and paraformaldehyde (1.20 g, 40 mmol) was stirred with concentrated HCl (15 mL) for 14 days, although with the first drops of concentrated HCl, the emulsion became red. The mixture was then neutralized by treatment with a saturated solution of Na$_2$CO$_3$. The mixture was extracted with EtOAc (3×30 mL). Organic layers were dried over MgSO$_4$ and the volatiles were evaporated under low pressure to give a beige solid which did not require further purification. Yield: 97%. Beige to red solid. $^1$H-NMR $\delta_H$: 1.43 (9H, s, 3×CH$_3$), 4.59 (2H, s, CH$_2$), 7.43 (1H, d, J=2.1 Hz, H$_{Ar}$), 7.52 (1H, d, J=2.1 Hz, H$_{Ar}$), 9.87 (1H, s, CHO), 11.86 (1H, s, OH).

(d) 3-tert-Butyl-5-diethylaminomethylsalicylaldehyde hydrochloride (6)

To a solution of 3-tert-butyl-5-chloromethylsalicylaldehyde (5)(226.5 mg, 1 mmol) in acetonitrile (60 mL), diethylamine (1 mmol) was added dropwise to give a greenish solution. The reaction was stirred at 30° C. overnight. After evaporation of volatiles, a green oil was obtained which was used without any purification for the next step. Yield: 77%. Green oil. $\square_{max}$ 3300, 2899 and 1720 cm$^{-1}$. 1H-NMR $\delta_H$: 1.35 (9H, s, C(CH$_3$)$_3$), 1.45 (6H, t, J=7.2 Hz, 2×CH$_2$CH$_3$), 3.43 (4H, q, J=7.2 Hz, 2×CH$_2$CH$_3$), 4.90 (2H, s, CCH$_2$N), 7.57 (1H, d, J=2.1 Hz, H$_{Ar}$), 8.03 (1H, d, J=2.1 Hz, H$_{Ar}$), 9.98 (1H, s, CHO), 12.00 (1H, br s, OH). 13C-NMR $\delta_C$(CDCl$_3$, 75 MHz): 10.8, 28.3, 33.7, 45.8, 56.0, 119.5, 129.8, 130.3, 133.7, 137.0, 159.0, 195.9.

HRMS: Calcd. for C$_{16}$H$_{26}$NO$_2$$^+$ 264.1964. Found 264.1953.

(e) (1R,2R)—N,N'-Bis(3-tert-butyl-5-diethylaminomethylsalicylidene)cyclohexane-1,2-diamine (7)

(1R,2R)-cyclohexane-1,2-diammonium dichloride (2)(93.5 mg, 0.5 mmol) and NaOMe (55 mg, 1 mmol) were stirred in MeOH (10 mL) for 30 min. Then, a solution of 3-tert-butyl-5-diethylaminomethylsalicylaldehyde hydrochloride (6)(299.8 mg, 1 mmol) in MeOH (5 mL) was added and the solution, which became rapidly yellow, was stirred overnight at 30° C. Evaporation of MeOH was followed by addition of a saturated solution of $Na_2CO_3$ (20 mL). Organic compounds were extracted using dichloromethane (3×15 mL). It is important that the aqueous phase remains completely colourless and that the organic layer changes colour from orange to green. Organic layers were dried over $MgSO_4$ and volatiles were removed under vacuum to give a greenish slurry oil which was used without any purification in the next step.

Yield: 55%. Yellow-green oil. $[\alpha]^{20}_D$-184.5 (c 1.0, $CHCl_3$). $\square_{max}$ 3410, 2899, 1610, 1550 and 830 $cm^{-1}$. $^1$H-NMR $\delta_H$: 0.99 (12H, t, J=7.2 Hz, 4×$CH_2CH_3$), 1.40 (18H, s, 2×C$(CH_3)_3$), 1.50-2.05 (8H, m, $(CH_2)_4$), 2.44 (8H, q, J=7.2 Hz, 4×$CH_2CH_3$), 3.40-3.50 (6H, m, 2×CHN, 2×$CCH_2N$), 6.95 (2H, d, J=1.8 Hz, 2×$H_{Ar}$), 7.17 (2H, d, J=1.8 Hz, 2×$H_{Ar}$), 8.28 (2H, s, 2×HC=N), 13.77 (2H, br s, 2×OH). 13C-NMR $\delta_C$: 11.9, 24.4, 29.6, 33.2, 34.8, 46.8, 57.3, 72.5, 118.4, 128.8, 129.8, 130.1, 136.9, 159.3, 165.7. HRMS (ESI): Calcd. for $C_{38}H_{61}N_4O_2^+$ 605.4795. found 605.4783.

(f) Bis[(1R,2R)—N,N'-Bis(3-tert-butyl-5-diethylaminomethylsalicylidene)cyclohexane-1,2-diaminoaluminium(III)]oxide (8)

This reaction has to be performed under an inert atmosphere in dry conditions. Ligand (7)(1 mmol) and $Al(OEt)_3$ (324.1 mg, 2 mmol) were dissolved in toluene (10 mL). The reacting mixture was heated to reflux for 5 hours. An occasional residue of alumina could be removed by filtering through a sinter. The mother liquor was evaporated and then, $H_2O$ (30 mL) and dichloromethane (30 mL) were added. The complex was extracted using dichloromethane (3×20 mL) and organic layers were dried over $MgSO_4$. Volatiles were remover under low pressure to give a pale solid, which was recrystallised using acetonitrile. Yield: 40%. Pale green solid. $[\alpha]^{20}_D$-522 (c 1.0, $CHCl_3$). $\square_{max}$ 2865, 1626, 1548, 1440, 1027, 836 and 577 $cm^{-1}$. $^1$H-NMR $\delta_H$: 1.02 (24H, t, J=7.2 Hz, 8×$CH_2CH_3$), 1.46 (36H, s, 4×$C(CH_3)_3$), 1.50-2.15 (16H, m, 2×$(CH_2)_4$), 2.52-2.7 (16H, m, 8×$CH_2CH_3$), 3.10-3.15 (2H, m, 2×CHN), 3.50-3.60 (8H, m, 4×$CCH_2N$), 3.80-3.85 (2H, m, 2×CHN), 7.09 (4H, d, J=5.7 Hz, 4×$H_{Ar}$), 7.35 (4H, d, J=5.7 Hz, 4×$H_{Ar}$), 8.19 (2H, s, 2×HC=N), 8.37 (2H, s, 2×1-1CN). 13C-NMR $\delta_C$: 10.2, 24.7, 29.9, 30.1, 35.0, 47.1, 57.6, 73.2, 118.9, 119.2, 128.9, 135.3, 141.7, 157.2, 165.1. m/z (ESI) 661.5 (100), 1275.9 (80), 1276.9 (72), 1277.9 (32), 1278.9 (16), 1279.9 (4)

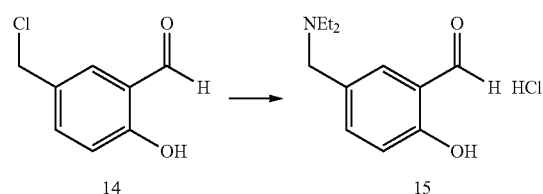

(g) 5-Diethylaminomethylsalicylaldehyde 15

To a solution of 5-(chloromethyl)salicylaldehyde (14)(345 mg, 2 mmol) in acetonitrile (70 mL), diethylamine (0.21 mL, 2 mmol) was added and the mixture refluxed overnight. Then, the solvent was evaporated to give compound 15 (625 mg, 99%) as a yellow oil. $\square_{max}$ 3383, 2648 and 1653 $cm^{-1}$. $^1$H-NMR $\delta_H$ 1.37 (6H, t, J=7.2 Hz, 2×$CH_2CH_3$), 3.43 (4H, q, J=7.2 Hz, 2×$CH_2CH_3$), 4.09 (2H, s, $CCH_2N$), 7.05 (1H, d, J=8.6 Hz, $H_{Ar}$), 8.03 (1H, d, J=8.6 Hz, $H_{Ar}$), 8.14 (1H, s, $H_{Ar}$), 9.98 (1H, s, CHO), 12.32 (1H, br s, OH). $^{13}$C-NMR $\delta_C$ 11.4, 46.4, 56.0, 118.8, 121.3, 136.7, 139.0, 162.7, 196.5. m/z(ESI) 208 (MH$^+$, 100), 293 (30), 317 (10). HRMS (ESI): Calculated for M$^+$ ($C_{12}H_{17}NO_2^+$) 208.1338. Found 208.1355.

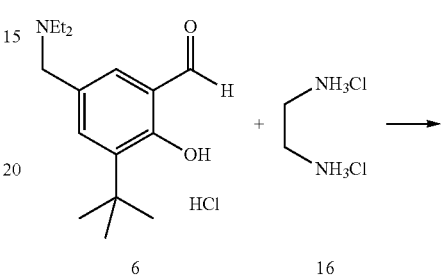

(h) N,N'-Bis(3-tert-butyl-5-diethylaminomethylsalicylidene)ethane-1,2-diamine 17

Compound 17 was synthesised from compounds 6 and 16 in an analogous manner to step (e) above. A yellow oil was obtained in 56% yield. $\square_{max}$ 2965, 2524 and 1629 $cm^{-1}$. 1H-NMR $\delta_H$ 1.44 (12H, t J=7.5 Hz, 4×$CH_2CH_3$), 1.51 (18H, s, 2×$C(CH_3)_3$), 2.70-2.80 (4H, m, $CCH_2N$), 3.02 (8H, q J=7.2 Hz, 4×$CH_2CH_3$), 3.60-3.80 (4H, m, 2×$CH_2$), 7.07-7.35 (4H, m, 4×$H_{Ar}$), 8.25 (2H, s, 2×HC=N), 13.99 (2H, br s, 2×OH). 13C-NMR $\delta_C$ 10.4, 28.0, 33.3, 45.2, 55.7, 58.1, 116.8, 128.2, 128.8, 135.6, 157.7, 165.3, 165.8. m/z(ESI) 551 (MH$^+$, 100), 524 (30).

HRMS (ESI): Calculated for MH$^+$ ($C_{34}H_{55}N_4O_2^+$) 551.4325. Found 551.4294.

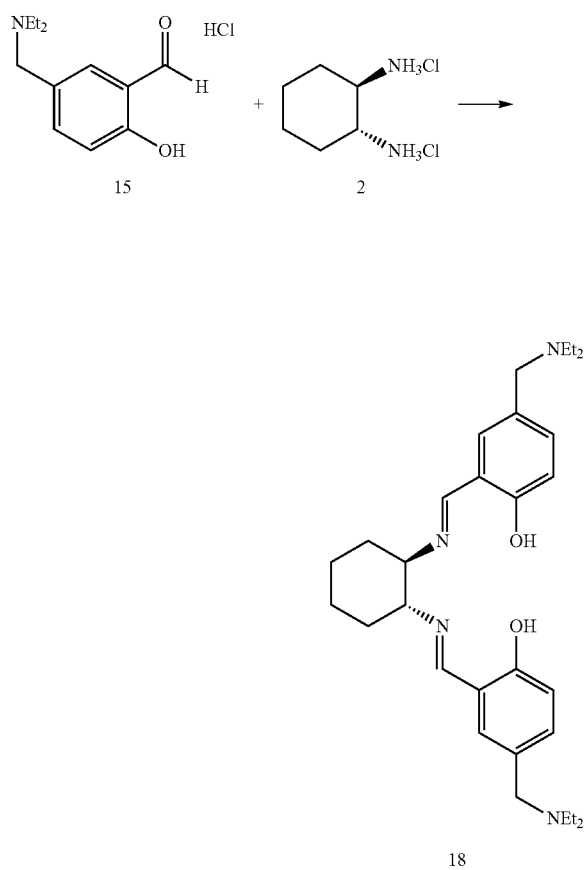

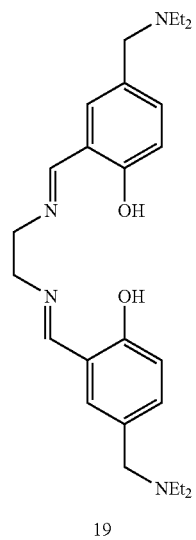

19

(j) N,N'-Bis(5-diethylaminomethylsalicylidene)ethane-1,2-diamine 19

Compound 19 was synthesised from compounds 15 and 16 in an analogous manner to step (e) above. A yellow oil was obtained in 53% yield. $\bar{v}_{max}$ 2801, 1632, and 1083 cm$^{-1}$. $^1$H-NMR $\delta_H$ 1.21 (12H, t J=7.5 Hz, 4×CH$_2$CH$_3$), 2.70-2.80 (4H, m, CCH$_2$N), 2.96 (8H, q J=7.2 Hz, 4×CH$_2$CH$_3$), 3.85-3.95 (4H, m, 2×CH$_2$), 6.83 (2H, d J=8.6 Hz, 2×H$_{Ar}$), 7.26 (2H, d J=8.6 Hz, 2×H$_{Ar}$), 7.42 (2H, s, 2×H$_{Ar}$), 8.34 (2H, s, 2×HC=N), 13.21 (2H, br s, 2×OH). $^{13}$C-NMR $\delta_C$ 11.9, 43.5, 47.8, 57.2, 117.0, 129.6, 126.5, 130.4, 132.0, 133.4, 166.9. m/z(ESI) 439 (MH$^+$, 100), 420 (20). HRMS (ESI): Calculated for MH$^+$ (C$_{34}$H$_{55}$N$_4$O$_2{}^+$) 439.3073. Found 439.3090.

(i) (1R,2R)—N,N'-Bis(5-diethylaminomethylsalicylidene)cyclohexane-1,2-diamine 18

Compound 18 was synthesised from compounds 15 and 2 in an analogous manner to step (e) above. A yellow oil was obtained in 65% yield. $[\alpha]^{20}{}_D$-302 (c 0.1, CHCl$_3$). $\bar{v}_{max}$ 2939, 1631 and 1089 cm$^{-1}$. $^1$H-NMR $\delta_H$ 1.25 (12H, t J=7.2 Hz, 4×CH$_2$CH$_3$), 1.50-2.00 (8H, m, (CH$_2$)$_4$) 2.89 (8H, q J=7.6 Hz, 4×CH$_2$CH$_3$), 2.90-3.00 (4H, m, 2×CCH$_2$N), 3.90-4.00 (2H, m, 2×CH), 6.83 (2H, d J=8.3 Hz, 2×H$_{Ar}$), 7.36 (2H, d J=8.4 Hz, 2×H$_{Ar}$), 7.43 (2H, s, 2×H$_{Ar}$) 8.25 (2H, s, 2×HC=N), 13.40 (2H, br s, 2×OH). $^{13}$C-NMR $\delta_C$ 9.5, 24.4, 33.0, 46.9, 56.0, 72.6, 117.7, 118.9, 120.8, 134.3, 134.8, 161.4, 165.3. m/z(ESI) 493 (MH$^+$, 100), 420 (20). HRMS (ESI): Calculated for MH$^+$ (C$_{30}$H$_{45}$N$_4$O$_2{}^+$) 493.3542. Found 493.3544.

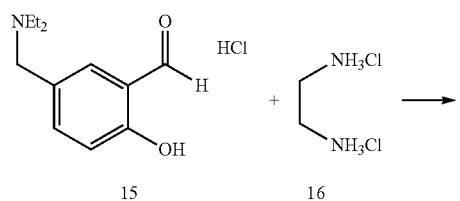

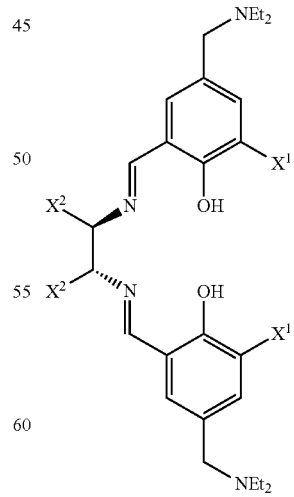

17: X$^1$ = $^t$Bu, X$^2$ = H
18: X$^1$ = H, X$^2$ = (CH$_2$)$_4$
19: X$^1$ = H, X$^2$ = H

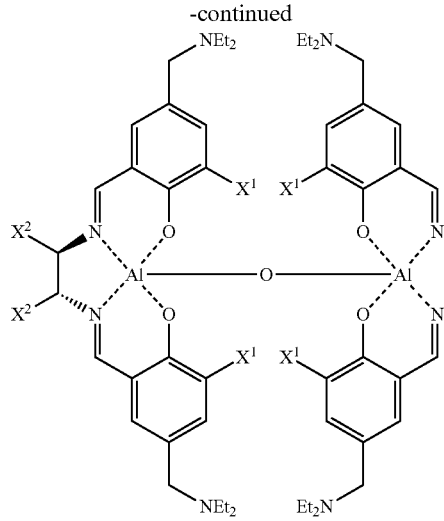

22: X¹ = ᵗBu, X² = H
23: X¹ = H, X² = (CH₂)₄
24: X¹ = H, X² = H (k) Bis[N,N'-Bis(3-tert-butyl-5-diethylaminomethyl-salicylidene)ethane-1,2-diaminoaluminium(III)]oxide 22, Bis[(1R,2R)—N,N'-Bis(5-diethylaminomethylsalicylidene)-cyclohexane-1,2-diaminoaluminium(III)]oxide 23 and Bis[N,N'-Bis(5-diethylaminomethylsalicylidene)ethane-1,2-diaminoaluminium(III)]oxide 24

Ligands 17-19 were converted to complexes 22-24 in an analogous manner to step (f) above.

22: pale yellow solid obtained in 55% yield. $\square\square_{max}$ 2522 and 2159 cm$^{-1}$. $^1$H-NMR $\delta_H$ 1.10-1.20 (24H, m, 8×CH₂CH₃), 1.43 (36H, s, 4×C(CH₃)₃), 2.90-3.15 (16H, m, 8×CH₂CH₃), 3.50-3.60 (8H, m, 4×CCH₂N), 3.70-4.00 (8H, m, 4×CH₂N), 7.19 (4H, s, 4×H$_{Ar}$), 7.30 (4H, s, 4×H$_{Ar}$), 8.33 (4H, s, 4×HC=N). $^{13}$C-NMR $\delta_C$ 11.2, 24.2, 33.6, 46.5, 55.3, 55.9, 120.9, 135.5, 137.5, 137.8, 139.6, 140.9, 162.0. m/z (ESI) 1170 (10), 1169 (35), 1168 (90), 1167 (MH⁺, 100).

HRMS (ESI): Calculated for MH⁺ ($C_{68}H_{104}N_8O_5Al_2^+$) 1167.7839. Found 1167.7799.

23: pale yellow solid obtained in 67% yield. $[\alpha]^{20}_D$ -170 (c 0.01, DMSO). $\square_{max}$ 2859, 1631 and 1084 cm$^{-1}$. $^1$H-NMR $\delta_H$ (DMSO-d₆): 1.04-1.99 (24H, m, 8×CH₂CH₃), 1.50-2.15 (16H, m, 2×(CH₂)₄), 2.5-2.6 (16H, m, 8×CH₂CH₃), 3.1-4.5 (12H, m, 4×CHN+4×CCH₂N), 6.91 (4H, d, J=7.6 Hz, 4×H$_{Ar}$), 7.40 (4H, d J=7.6 Hz, 4×H$_{Ar}$), 7.55 (4H, s, 4×H$_{Ar}$), 8.43 (4H, s, 4×HC=N).

24: pale yellow solid obtained in 65% yield. $\square\square_{max}$ 2971, 2225 and 1634 cm$^{-1}$. $^1$H-NMR $\delta_H$ (DMSO-d₆): 1.05 (24H, m, 8×CH₂CH₃), 2.15-3.5 (24H, m, 8×CH₂CH₃+4×CCH₂N), 3.90 (8H, m, CH₂N), 6.81 (4H, d J=5.7 Hz, 4×H$_{Ar}$), 7.32 (8H, m, 8×H$_{Ar}$), 8.50 (4H, s, HC=N).

Example 1

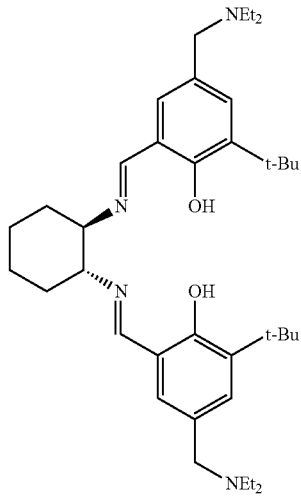

7

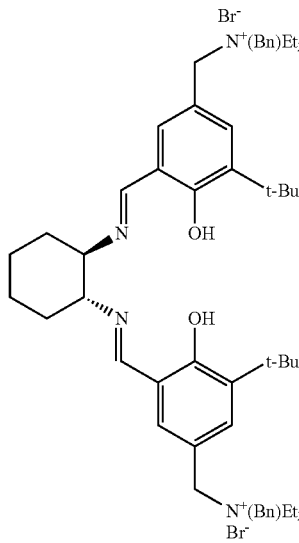

9

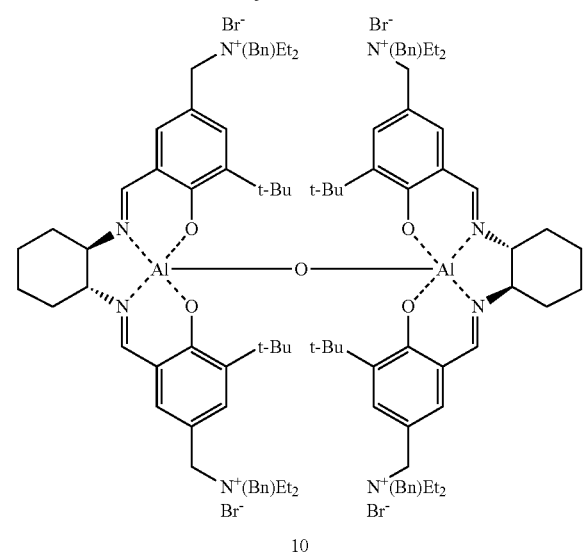

10

(a) (1R,2R)—N,N'-Bis[3-tert-butyl-5-(N-benzyl-N, N-diethylaminomethyl)salicylidene]cyclohexane-1, 2-diamine dibromide (9)

To a solution of (1R,2R)—N,N'-bis(3-tert-butyl-5-diethylaminomethylsalicylidene)-cyclohexane-1,2-diamine (7)(604.9 mg, 1 mmol) in acetonitrile (60 mL), benzyl bromide (342.1 mg, 2 mmol) was added dropwise to give a yellow solution. The reaction was stirred at 30° C. overnight. After evaporation of volatiles, a yellow oil was obtained which was recrystallised from n-hexane. Yield: 55%. Bright yellow solid. $[\alpha]^{20}_D$-38.6 (c 1.0, CHCl$_3$). $\square\square_{max}$ 3392, 2960, 1608, 1545 and 1470 cm$^{-1}$. $^1$H-NMR $\delta_H$: 1.00-2.00 (38H, m, 10×CH$_3$, (CH$_2$)$_4$), 3.40-3.50 (2H, m, 2×CHN), 3.56 (8H, q, J=7.5 Hz, 4×CH$_2$CH$_3$), 4.20 (4H, 2×CCH$_2$N), 4.99 (4H, 2×CCH$_2$N), 6.44 (2H, d, J=2.4 Hz, 2×H$_{Ar}$), 7.65 (2H, d, J=2.4 Hz, 2×H$_{Ar}$), 8.38 (2H, s, 2×HC=N), 14.30 (2H, br s, 2×OH). $^{13}$C-NMR $\delta_C$: 11.3, 23.4, 29.3, 31.2, 35.1, 51.1, 60.3, 60.4, 72.7, 120.2, 128.6, 128.8, 129.2, 129.9, 130.6, 134.9, 157.2, 163.9.

(b) Bis[(1R,2R)—N,N'-Bis(3-tert-butyl-5-(N-benzyl-N,N-diethylaminomethyl)salicylidene bromide]cyclohexane-1,2-diaminoaluminium(III) oxide (10)

This reaction has to be performed under an inert atmosphere in dry conditions. Ligand (9)(1 mmol) and Al(OEt)$_3$ (324.1 mg, 2 mmol) were dissolved in a mixture of toluene (5 mL) and ethanol (5 mL). The reacting mixture was heated to reflux for 5 hours. An occasional residue of alumina could be removed by filtering through a sinter. The mother liquor was evaporated, then H$_2$O (30 mL) and dichloromethane (30 mL) were added. The complex was extracted using dichloromethane (3×20 mL) and organic layers were dried over MgSO$_4$. Volatiles were remover under low pressure to give a pale solid, which was recrystallised using Et$_2$O. Yield: 33%. Pale yellow solid. $[\alpha]^{20}_D$-281 (c 1.0, CHCl$_3$). IR 2946, 1624, 1551, 1470, 1208 and 1030 cm$^{-1}$. $^1$H-NMR $\delta_H$: 1.05 (24H, t, J=7.3 Hz, 8×CH$_2$CH$_3$), 1.45 (36H, s, 4×C(CH$_3$)$_3$), 1.50-2.20 (16H, m, 2×(CH$_2$)$_4$), 2.45-2.50 (16H, m, 8×CH$_2$CH$_3$), 3.10-3.15 (2H, m, 2×CHN), 3.40-3.50 (16H, m, 8×CCH$_2$N), 3.80-3.85 (2H, m, 2×CHN), 7.10-7.50 (28H, m, 28×H$_{Ar}$), 8.20 (2H, s, 2×HC=N), 8.35 (2H, s, 2×HC=N). $^{13}$C-NMR $\delta_C$: 10.3, 24.5, 30.0, 30.2, 34.6, 48.3, 57.6, 60.2, 73.8, 119.1, 119.6, 124.6, 127.4, 127.9, 128.9, 135.2, 141.6, 156.5, 166.1.

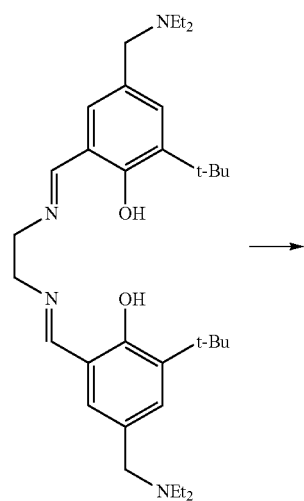

17

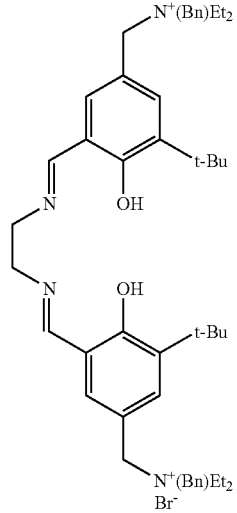

20

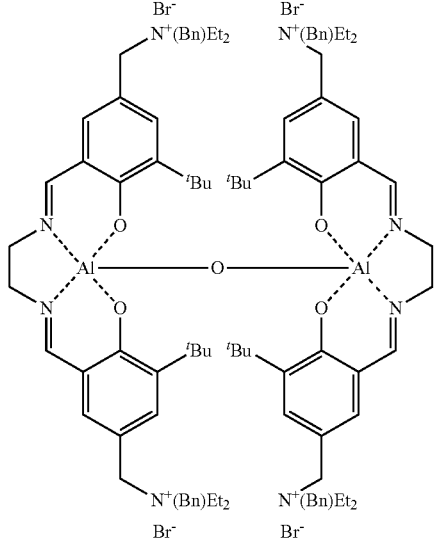

21

(c) N,N'-Bis[3-tert-butyl-5-(N-benzyl-N,N-diethylaminomethyl)salicylidene]ethane-1,2-diamine dibromide (20)

The bis-ammonium salt (20) was synthesised from the salen ligand (17) in an analogous manner to step (a) above. $\square_{max}$ 3383, 2648 and 1647 cm$^{-1}$. $^1$H-NMR $\delta_H$ 1.44 (12H, t J=7.5 Hz, 4×CH$_2$CH$_3$), 1.51 (18H, s, 2×C(CH$_3$)$_3$), 2.78 (8H, q J=7.2 Hz, 4×CH$_2$CH$_3$), 3.6-3.8 (4H, m, 2×CH$_2$N), 3.9-4.1 (4H, m, CCH$_2$N), 7.0-7.4 (4H, m, 4×H$_{Ar}$), 8.25 (2H, s, 2×HC=N), 13.99 (2H, br s, 2×OH). $^{13}$C-NMR $\delta_C$ 10.9, 29.6, 35.1, 46.5, 56.6, 59.7, 65.7, 118.8, 121.1, 127.5, 128.8, 129.0, 129.5, 135.5, 137.3, 139.6, 141.0, 162.6.

(d) Bis[N,N'-Bis(3-tert-butyl-5-(N-benzyl-N,N-diethylaminomethyl)salicylidene bromide]ethane-1,2-diaminoaluminium(III) oxide (21)

The catalyst (21) was synthesised from the bis-ammonium salt (20) in an analogous manner to step (b) above. A pale yellow solid was obtained in 42% yield. ☐$_{max}$ 2950, 1634 and 1029 cm$^{-1}$. $^1$H-NMR δ$_H$ 1.05 (24H, t J=7.3 Hz, 8×CH$_2$CH$_3$), 1.45 (36H, s, 4×C(CH$_3$)$_3$), 2.95-3.15 (16H, m, 8×CH$_2$CH$_3$), 3.20-3.45 (4H, m, 2×CH$_2$N), 3.90-4.30 (4H, m, 2×CH$_2$N), 4.50 (8H, s, 4×CCH$_2$N), 7.10-7.50 (28H, m, 28×H$_{Ar}$), 8.00 (2H, s, 2×HC=N), 8.13 (2H, s, 2×HC=N). $^{13}$C-NMR δ$_C$ 11.5, 30.0, 35.7, 46.91, 55.4, 57.3, 65.7, 119.2, 119.6, 126.3, 131.1, 132.5, 132.6, 134.4, 141.9, 164.9, 170.1.

for 16 hours. The solvent was evaporated in vacuo to give compound (25) or (26) as a pale orange powder.

25: pale orange solid obtained in 52% yield. [α]$^{20}_D$-240 (c 0.01, DMSO). ☐$_{max}$ 2923, 1625 and 1088 cm$^{-1}$. $^1$H-NMR δ$_H$ (DMSO-d$_6$): 1.04-1.99 (24H, m, 8×CH$_2$CH$_3$), 1.50-2.15 (16H, m, 2×(CH$_2$)$_4$), 2.5-2.6 (16H, m, 8×CH$_2$CH$_3$), 3.1-3.9 (12H, m, 4×CHN+4×CCH$_2$N), 4.50 (8H, s, 4×CCH$_2$N), 6.74 (4H, d, J=7.3 Hz, 4×H$_{Ar}$), 6.82 (4H, d, J=7.3 Hz, 4×H$_{Ar}$), 7.13-7.46 (24H, m, 24×H$_{Ar}$), 8.43 (4H, s, 4×HC=N).

26: pale orange solid obtained in 40% yield. ☐$_{max}$ 2960, 1644 and 1032 cm$^{-1}$. $^1$H-NMR δ$_H$ (DMSO-d$_6$): 0.99 (12H, m, 4×CH$_3$CH$_2$), 1.52 (12H, m, 4×CH$_3$CH$_2$), 3.21 (16H, q J=7.1 Hz, 8×CH$_2$CH$_3$), 4.1-4.3 (16H, m, 4×CCH$_2$N+4×CH$_2$N), 4.57 (8H, s, 4×CCH$_2$N), 6.97 (4H, d, J=8.3 Hz, 4×H$_{Ar}$), 7.1-7.4 (24H, m, 24×H$_{Ar}$), 7.5-7.6 (4H, m, 4×H$_{Ar}$), 7.60 (4H, s, 4×HC=N).

Example 2

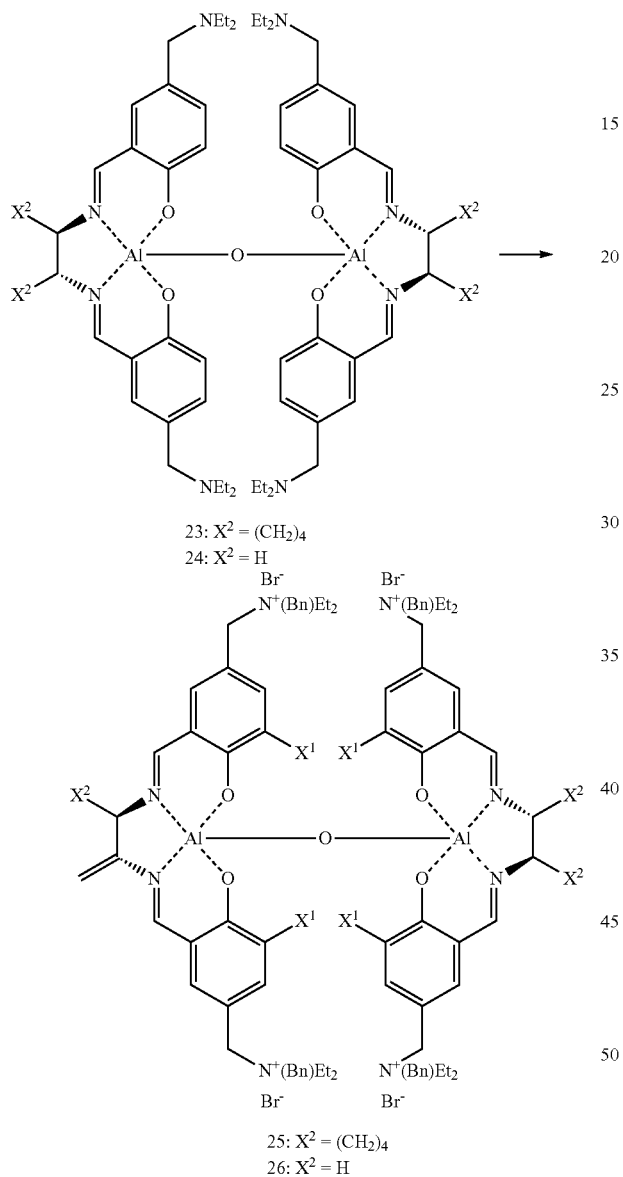

23: X$^2$ = (CH$_2$)$_4$
24: X$^2$ = H

25: X$^2$ = (CH$_2$)$_4$
26: X$^2$ = H

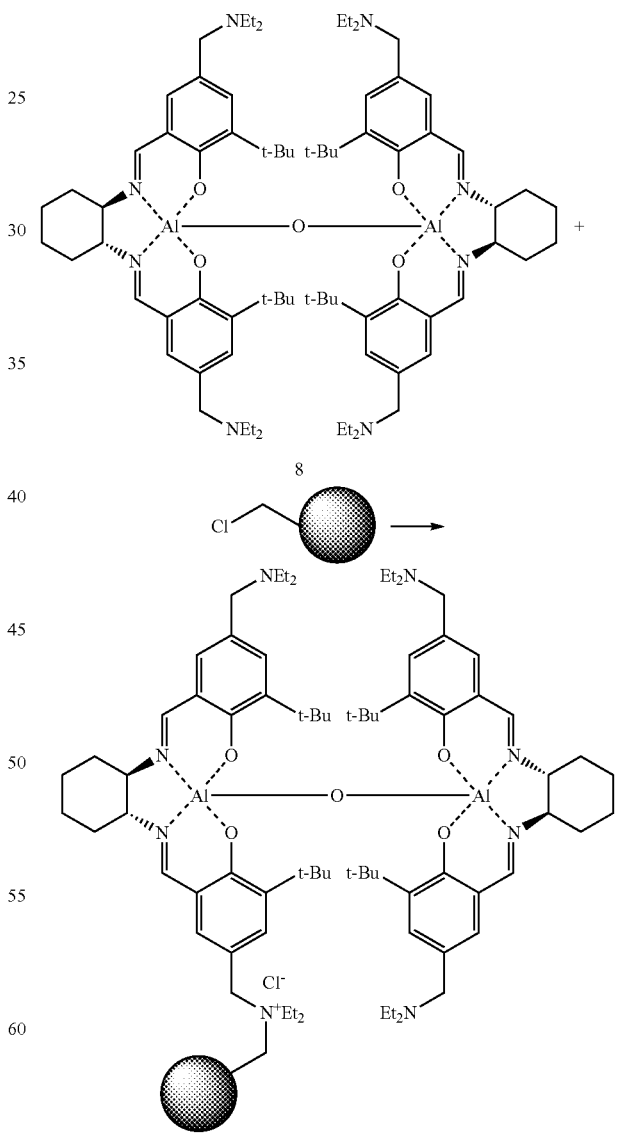

(e) Bis[(1R,2R)—N,N'-Bis(5-(N-benzyl-N,N-diethylaminomethyl)salicylidene bromide]cyclohexane-1,2-diaminoaluminium(III) oxide (25) and Bis[N,N'-Bis(5-(N-benzyl-N,N-diethylaminomethyl)salicylidene bromide]ethane-1,2-diaminoaluminium (III) oxide (26)

Benzyl bromide (0.07 mL, 0.6 mmol) was added to a solution of bimetallic complex (23) or (24) (0.1 mmol) in propylene carbonate (10 mL) and the reaction stirred at 85° C.

Merrifield resin (120 mg, 0.2 mmol) was swollen in a minimal amount of DMF/dichloromethane. Complex (8)(240 mg, 0.4 mmol) was added and the mixture was stirred for 24 hours at 30° C. The resin was filtered off and washed using DMF (10 mL), DMF/dichloromethane (1:1) (10 mL), dichloromethane (10 mL), then it was dried under vacuum to give compound (12) as a yellow-coloured resin.

Example 3

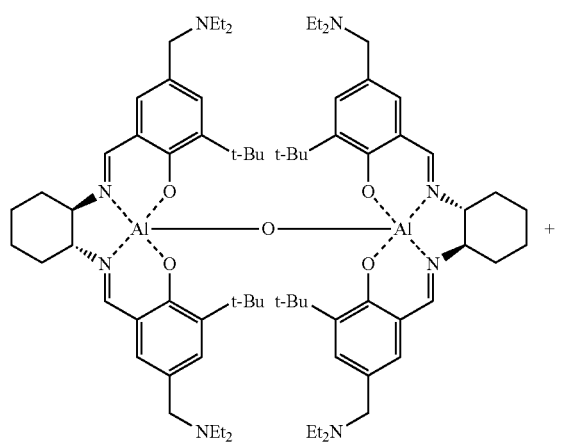

8

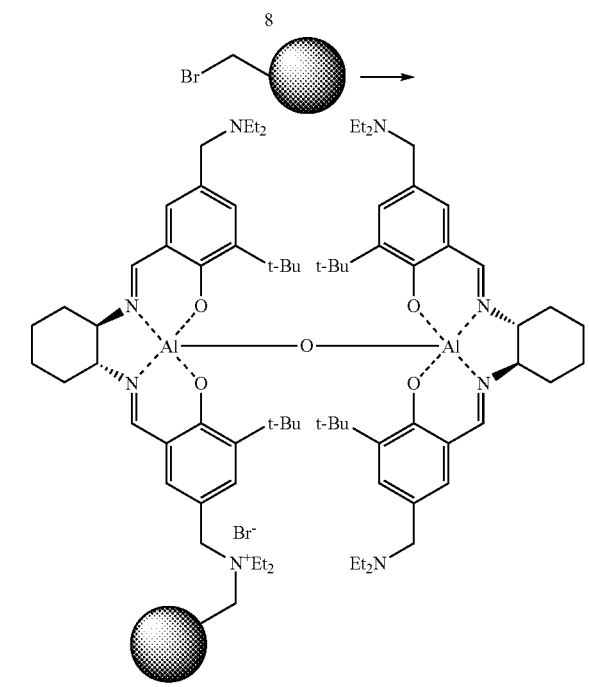

13

(a) Merrifield resin (120 mg, 0.2 mmol) was converted into the corresponding bromomethyl resin by treatment with a large excess of tetrabutylammonium bromide for several days in dichloromethane/DMF. Complex (8)(240 mg, 0.4 mmol) was added to this resin and the mixture was stirred for 24 hours at 30° C. The resin was filtered off and was washed using DMF (10 mL), DMF/dichloromethane (1:1) (10 mL), dichloromethane (10 mL), then dried under vacuum to give yellow-coloured resin (13). $\square_{max}$ 2920, 2160, 1634, 1450 and 1066 cm$^{-1}$, (b) Immobilized catalyst 27 was synthesised from complex (22) in an analogous manner to step (a) above. 75% yield. $\square_{max}$ 2963, 2159, 1634, 1451 and 1091 cm$^{-1}$.

Example 4

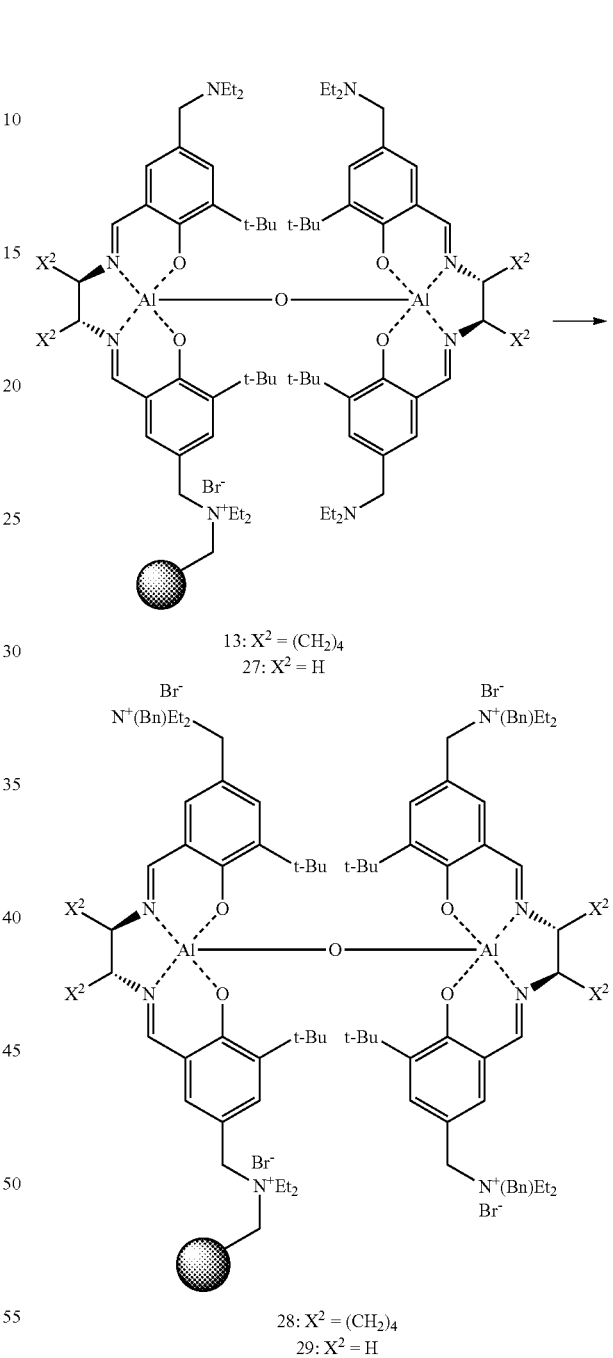

13: $X^2 = (CH_2)_4$
27: $X^2 = H$

28: $X^2 = (CH_2)_4$
29: $X^2 = H$

A sample of resin (13) or (27) (0.04 mmol) was swollen in DMF/CH$_2$Cl$_2$ and a large excess of benzyl bromide (40 mg, 0.24 mmol) was added. The mixture was stirred at room temperature for 24 hours, then the reaction was filtered and the resin washed with DMF (10 mL), DMF/dichloromethane (1:1) (10 mL), dichloromethane (10 mL), then dried in vacuo to give a yellow-coloured resin.
(28): $\square_{max}$ 2922, 2158, 1634, 1635, 1450 and 1028 cm$^{-1}$
(29): 83% yield. $\square_{max}$ 2961, 2153, 1636, 1544 and 1023 cm$^{-1}$

Example 5 a) Complexes (10), (21), (25) and (26)

Complexes (10), (21), (25) and (26) were tested in the reaction of some terminal epoxides with carbon dioxide at room temperature and atmospheric pressure.

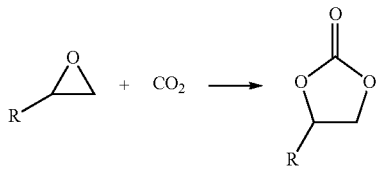

TABLE 1

Cyclic carbonate formation from epoxides.

| Entry | Complex | R | TBAB (mol-%) | Time (h) | Conversion (%)[a] |
|---|---|---|---|---|---|
| 1 | 10 | Ph | 0 | 3 | 71 |
| 2 | 10 | Ph | 0 | 6 | 97 |
| 3 | 10 | Ph | 2.5 | 3 | 74 |
| 4 | 10 | n-Bu | 0 | 3 | 30[b] |
| 5 | 10 | n-Bu | 0 | 6 | 63[b] |
| 6 | 10 | n-Octyl | 0 | 3 | 44 |
| 7 | 10 | n-Octyl | 0 | 6 | 81 |
| 8 | 10 | CH$_2$OH | 0 | 3 | 55 |
| 9 | 10 | CH$_2$OH | 0 | 6 | 79 |
| 10 | 10 | CH$_2$Cl | 0 | 3 | 59[b] |
| 11 | 10 | CH$_2$Cl | 0 | 6 | 81[b] |
| 12[c] | 10 | Me | 0 | 3 | 50[b] |
| 13[c] | 10 | Me | 0 | 6 | 62[b] |
| 14 | 21 | Ph | 0 | 3 | 69 |
| 15 | 21 | Ph | 0 | 6 | 88 |
| 16 | 21 | Ph | 0 | 24 | 99 |
| 17 | 25 | Ph | 0 | 3 | 48 |
| 18 | 25 | Ph | 0 | 6 | 60 |
| 19 | 25 | Ph | 0 | 24 | 73 |
| 20 | 26 | Ph | 0 | 3 | 54 |
| 21 | 26 | Ph | 0 | 6 | 69 |
| 22 | 26 | Ph | 0 | 24 | 89 |

Reactions carried out neat with dimeric Al(salen) complex (2.5 mol-%) and the corresponding epoxide (1 mmol) under carbon dioxide at 26° C. and 1 atm unless otherwise stated.
[a]Determined by $^1$H-NMR spectroscopy.
[b]Volatile starting material was removed and the yield was determined by difference of weight.
[c]Reaction performed at 0° C.

b) Complexes 12 & 13

These complexes were used at 2.5 mol % in propylene carbonate (5 eq.) and styrene oxide (1 mmol) under carbon dioxide at 26° C. and 1 atmosphere pressure unless otherwise stated below. The reaction was carried out by dissolving the complexes (0.0415 mmol) in propylene carbonate (0.85 g) in a sample vial fitted with a magnetic stirrer bar. Styrene oxide (200 mg, 1.66 mmol) was then added and the sample vial was placed in a large conical flask. The conical flask was placed in an oil bath thermostatted at 26° C. Cardice pellets were added to the conical flask which was fitted with a rubber stopper pierced by a deflated balloon. The reaction was stirred for the required length of time, then filtered to remove the supported catalyst which was washed thoroughly with CH$_2$Cl$_2$ (20 mL). The filtrate and washings were combined and evaporated in vacuo and the residue analysed by $^1$H NMR spectroscopy to determine the conversion of styrene oxide to styrene carbonate. The immobilized catalyst could be returned to the sample vial and reused, as shown with the repeated runs below.

| Entry | Catalyst | Run | Time (h) | Conversion (%)[a] |
|---|---|---|---|---|
| 1[b,c] | 12 | 1st | 3 | 0 |
| 2[b,c,d] | 12 | 1st | 3 | 17 |
| 3[b,c,d] | 12 | 2nd | 3 | 9 |
| 4[c] | 12 | 1st | 3 | 37 |
| 5[c] | 12 | 1st | 6 | 67 |
| 6[c] | 12 | 1st | 20 | 100 |
| 7[c] | 12 | 2nd | 3 | 5 |
| 8[c] | 12 | 2nd | 6 | 37 |
| 9[c] | 12 | 2nd | 20 | 86 |
| 10[c] | 12 | 3rd | 3 | 0 |
| 11[c] | 12 | 3rd | 6 | 20 |
| 12[c] | 12 | 3rd | 20 | 63 |
| 13 | 13 | 1st | 3 | 11 |
| 14 | 13 | 1st | 6 | 69 |
| 15 | 13 | 1st | 20 | 100 |
| 16 | 13 | 2nd | 3 | 0 |
| 17 | 13 | 2nd | 6 | 37 |
| 18 | 13 | 2nd | 20 | 94 |
| 19 | 13 | 3rd | 3 | 5 |
| 20 | 13 | 3rd | 6 | 25 |
| 21 | 13 | 3rd | 20 | 70 |

[a]Determined by GC.
[b]Reaction performed solvent-free.
[c]Reaction performed in the presence of 2.5 mol % of TBAB.
[d]Only 0.5 mol % of the complex (12) was used.

The use of propylene carbonate as a solvent is compatible with the catalytic system.

c) Complexes (28) and (29)

Complexes (28) and (29) were tested at 2.5 mol % in the in the reaction of styrene oxide (1 mmol) with carbon dioxide at 26° C. and 1 atmosphere pressure in the presence of propylene carbonate (5 eq.) as a solvent, with 20 hours for each reaction. The complexes were found to be recyclable. The method is as in step b) above.

Complex (28) gave styrene carbonate yields of 79, 73, 66 and 60% over four consecutive reactions.

Complex (29) gave styrene carbonate yields of 79, 71, 67 and 64% over four consecutive reactions.

Example 6

(a) Synthesis of [Al(salen)]$_2$O Electrostatically Supported on Clays

Clays (0.5 g) were activated at 120° C. for three days prior to use. After the activation, the clay (0.5 g) was added to a solution of aluminium complex (21) (0.140 g, 0.08 mmol) in DMF (30 mL) and refluxed for 30 hours. Subsequently, the mixture was filtered and washed with DMF (4×20 mL), EtOAc (4×20 mL) and dichloromethane (3×20 mL) to yield a powder which was dried under vacuum for 24 hours.

[Al(salen)]$_2$O supported on Bentonite (30): Pale brown solid, yield 99%. $\square_{max}$ 3540, 2150, 1987 and 1659 cm$^{-1}$.

[Al(salen)]$_2$O supported on Montmorillonite K10 (31): Purple solid, yield 99%. $\square_{max}$ 3500, 1659 and 922 cm$^{-1}$.

[Al(salen)]$_2$O supported on Al pillared clay (32): Pale brown solid, yield 99%. $\square_{max}$ 3500, 1654 and 1034 cm$^{-1}$.

(b) Synthesis of Styrene Carbonate Using [Al(salen)]$_2$O Electrostatically Supported on Clays Styrene oxide (0.2 g, 1.66 mmol) and catalyst (30-32) (0.5 g, 0.1 mmol/g support) in propylene carbonate (0.84 g) were placed in a sample vial fitted with a magnetic stirrer bar and placed in a large conical flask. The conical flask was placed in an oil bath thermostatted at 26° C. Cardice pellets were added to the conical flask which was fitted with a rubber stopper pierced by a deflated balloon. The contents of the reaction vial were stirred for 24 hours during which time the balloon inflated as the cardice pellets evaporated. The reaction was filtered to remove supported catalyst and the solution analysed by GC to determine the conversion of styrene oxide into styrene carbonate.

| Catalyst | Conversion (%) |
|----------|----------------|
| 30 | 5% |
| 31 | 3% |
| 32 | 7% |

Example 7

(a) Synthesis of Modified $SiO_2$ (3-Chloropropyl)-triethoxysilane (0.16 mL, 2 mmol) was added to a mixture of activated $SiO_2$ (2 g) in dry toluene (25 mL) and refluxed under $N_2$ for 24 hours. Subsequently, the mixture was filtered and washed with EtOAc (4×50 mL) to yield a yellow powder (95%). $\square_{max}$ 2505, 2160 and 1975 cm$^{-1}$.

(b) Synthesis of [Al(salen)]$_2$O$^+$Cl$^-$ Supported on Modified $SiO_2$ (33)

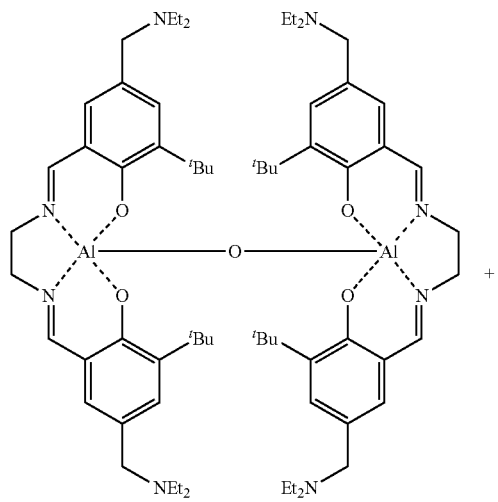

22

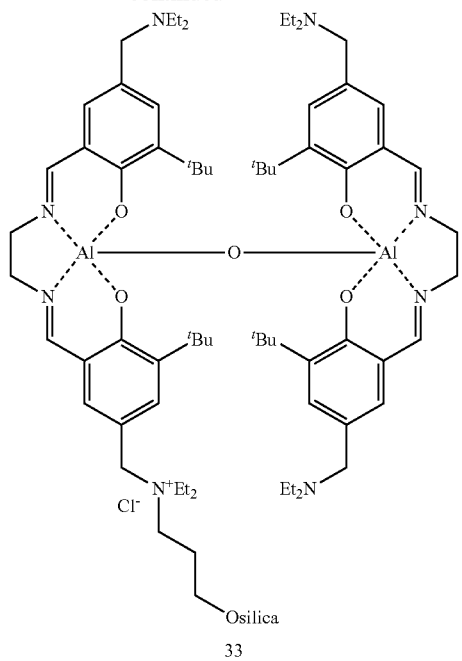

33

Modified $SiO_2$ (0.1 g) was added to a solution of aluminium complex (22) (0.175 g, 0.15 mmol) in $CH_3CN$ (40 mL) and the mixture was refluxed overnight. Then, the mixture was filtered and washed with EtOAc (4×50 mL) to give silica supported complex (33) as a yellow powder. $\square\square_{max}$ 3500, 1649 and 1070 cm$^{-1}$.

(c) Synthesis of [Al(salen)]$_2$O$^+$Br$^-$ Supported on Modified $SiO_2$ (34)

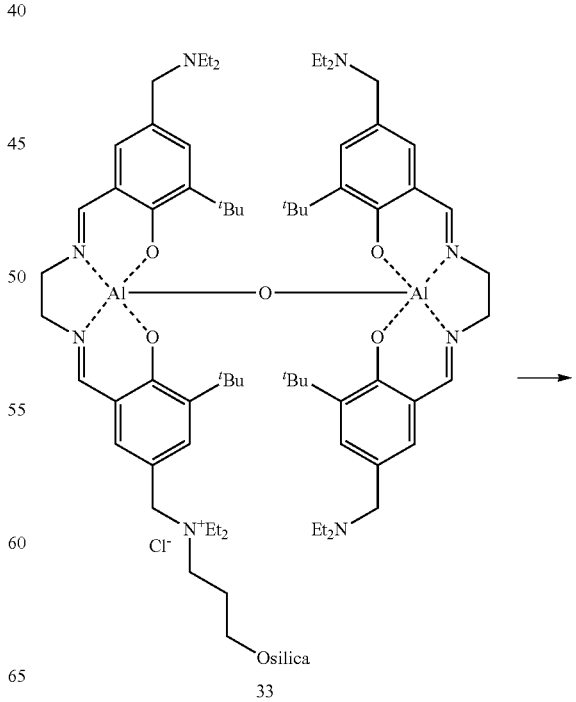

33

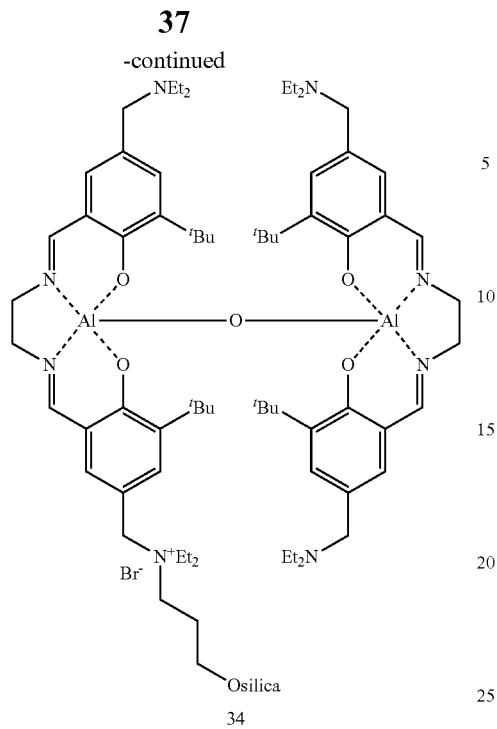

34

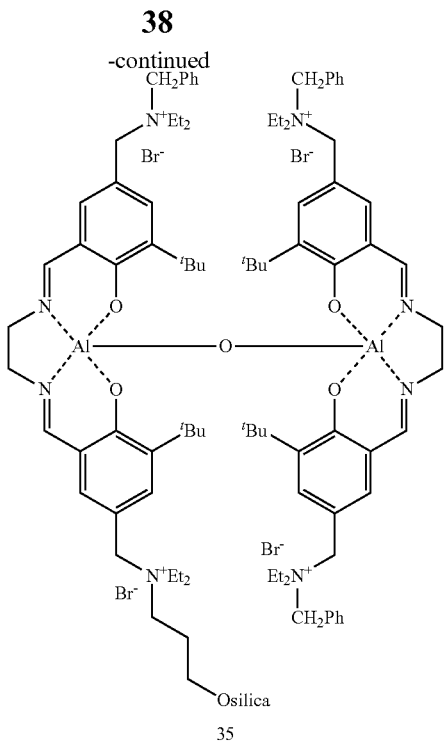

35

Tetrabutylammonium bromide (193 mg, 6 mmol) was added to a suspension of supported complex (33) (0.220 g, 1 mmol) in CH$_3$CN (40 mL) and the resulting mixture was refluxed overnight. Then, the mixture was filtered and washed with EtOAc (4×50 mL) to give silica supported complex (34) as a yellow powder. $\square_{max}$ 3427, 1628 and 1070 cm$^{-1}$.

(d) Synthesis of Benzylated [Al(salen)]$_2$O$^+$Br$^-$ Supported on Modified SiO$_2$(35)

Benzyl bromide (0.09 mL, 0.72 mmol) was added to a suspension of supported catalyst (34) (0.240 g, 1 mmol) in CH$_3$CN (40 mL) and the resulting mixture was refluxed overnight. Subsequently, the mixture was filtered and washed with EtOAc (4×50 mL) to give silica supported complex (35) as a yellow powder. $\square_{max}$ 3410, 1633 and 1078 cm$^{-1}$.

Example 8

(a) Synthesis of Modified Al Pillared Clay (3-Chloropropyl)-triethoxysilane (0.16 mL, 2 mmol) was added to a mixture of activated Al pillared clay (2 g) in dry toluene (25 mL) and the mixture was refluxed under N$_2$ for 24 hours. Then, the mixture was filtered and washed with EtOAc (4×50 mL) to give a yellow powder (95%). $\square_{max}$ 3512 and 1028 cm$^{-1}$.

(b) Synthesis of [Al(salen)]$_2$O$^+$Cl$^-$ Supported on Modified Al Pillared Clay (36)

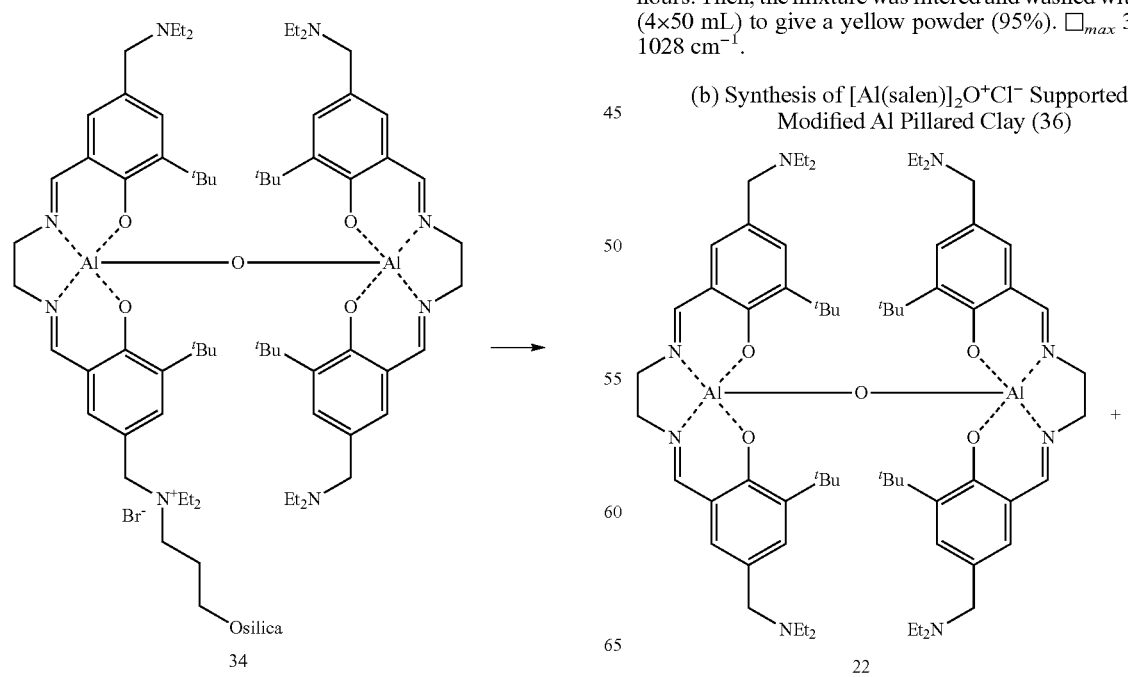

-continued

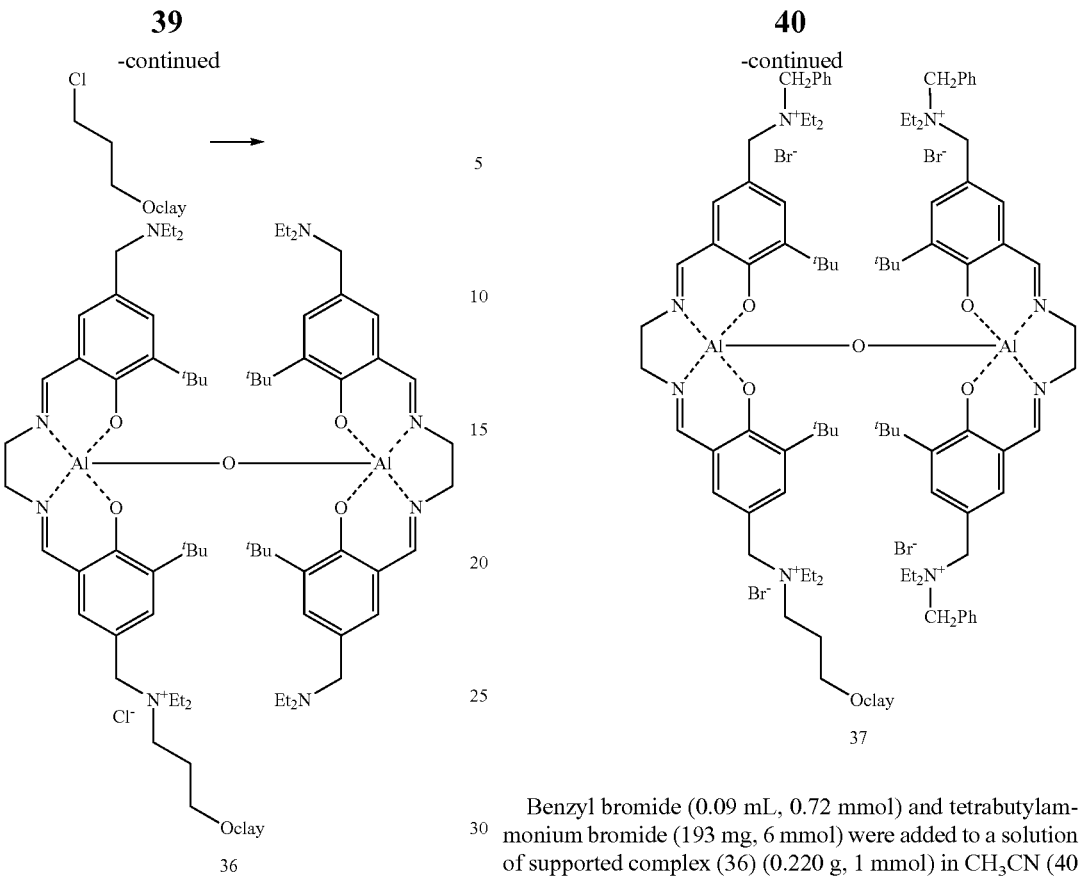

36

Modified Al pillared clay (0.1 g) was added to a solution of aluminium complex (22) (0.175 g, 0.15 mmol) in CH$_3$CN (40 mL) and the mixture was then refluxed overnight. Subsequently, the mixture was filtered and washed with EtOAc (4×50 mL) and dichloromethane (3×50 mL) to give clay supported complex (36) as a yellow powder. $\square_{max}$ 3410, 1627 and 1031 cm$^{-1}$.

(c) Synthesis of Benzylated [Al(salen)]$_2$O$^+$Br$^-$ Supported on Modified Al Pillared Clay (37)

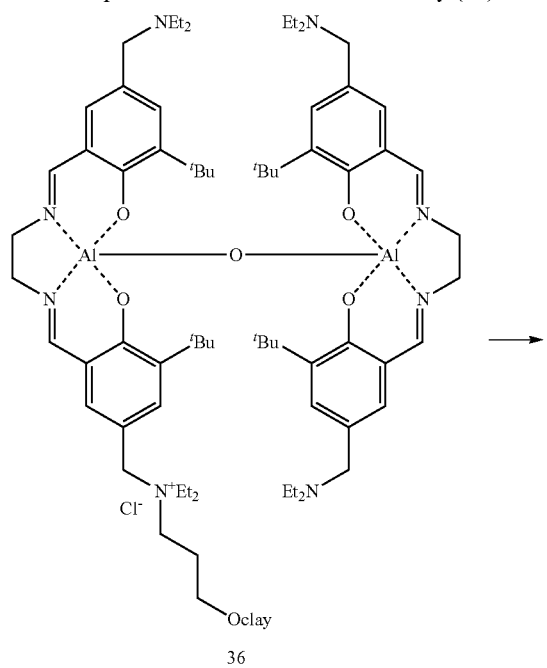

36

37

Benzyl bromide (0.09 mL, 0.72 mmol) and tetrabutylammonium bromide (193 mg, 6 mmol) were added to a solution of supported complex (36) (0.220 g, 1 mmol) in CH$_3$CN (40 mL) and the resulting mixture was refluxed overnight. Subsequently, the mixture was filtered and washed with EtOAc (4×50 mL) to give clay supported complex (37) as a yellow powder. max 3415, 1627 and 1028 cm$^{-1}$.

Example 9

Synthesis of Styrene Carbonate Using Supported Catalysts (35) and (37)

Styrene oxide (0.2 g, 1.66 mmol) and catalyst (35) or (37) (0.083 g, 0.5 mmol/g support) were placed in a sample vial fitted with a magnetic stirrer bar and placed in a large conical flask. The conical flask was placed in an oil bath thermostatted at 26° C. Cardice pellets were added to the conical flask which was fitted with a rubber stopper pierced by a deflated balloon. The contents of the reaction vial were stirred for 24 hours during which time the balloon inflated as the cardice pellets evaporated. The reaction was filtered to remove supported catalyst and the solution analysed by GC to determine the conversion of styrene oxide into styrene carbonate.

| Catalyst | Conversion (%) |
|---|---|
| 35 | 86 |
| 37 | 21 |

Example 10

(a) Synthesis of Modified MCM-41

(3-Chloropropyl)-triethoxysilane (0.16 mL, 2 mmol), was added to a suspension of activated MCM-41 (2 g) in dry toluene (25 mL) and the mixture refluxed under N$_2$ for 24 hours. The mixture was then filtered and washed with EtOAc (4×50 mL) to give a white powder (94%). $\square_{max}$ 2681, 1711, 1057 and 807 cm$^{-1}$.

(b) Synthesis of [Al(salen)]$_2$O$^+$Cl$^-$ Supported on Modified MCM-41 (38)

3-Chloropropyl modified MCM-41 (0.52 g) was added to a solution of aluminium complex (22) (1.50 g, 0.45 mmol) in CH$_3$CN (40 mL) and the mixture refluxed overnight. Then, the reaction was filtered and washed with EtOAc (6×50 mL) to leave MCM-41 supported complex (38) as a yellow powder (0.86 g, 86%). $\square_{max}$ 3122, 1628, 1057 and 789 cm$^{-1}$.

(c) Synthesis of Benzylated [Al(salen)]$_2$O$^+$Br$^-$ Supported on Modified MCM-41 (39)

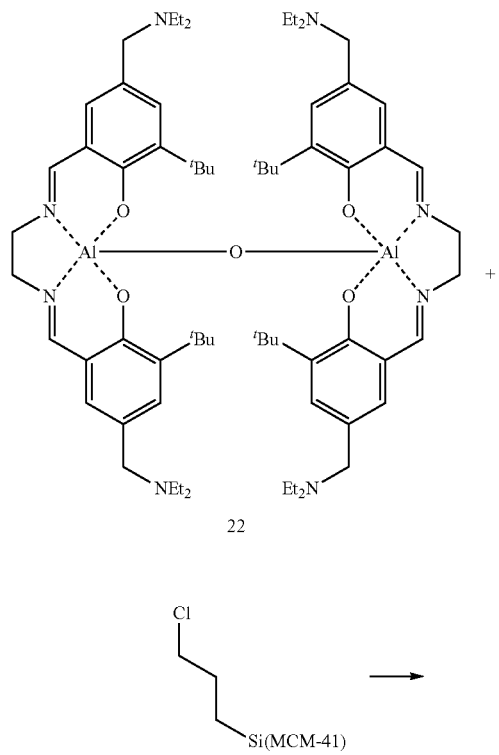

22

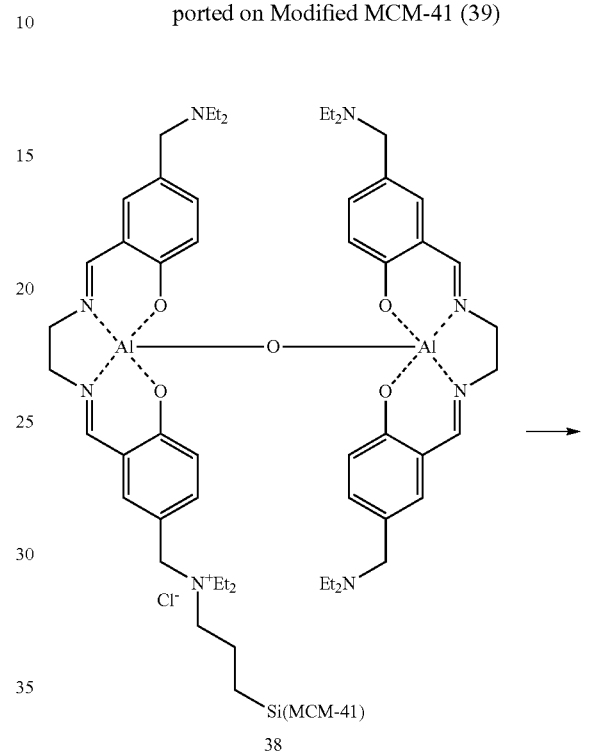

38

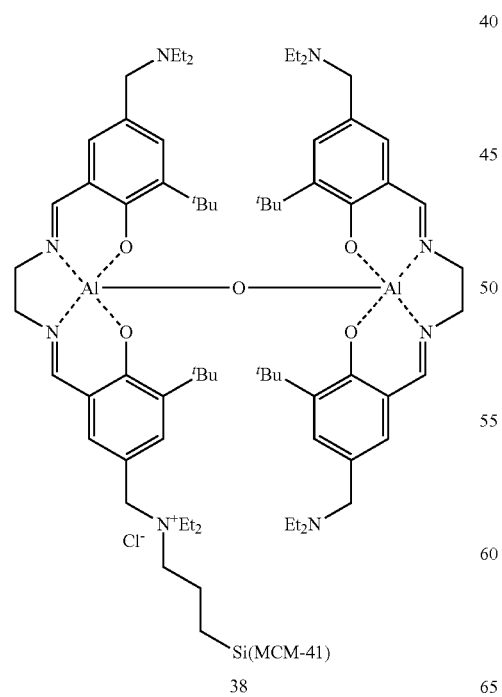

38

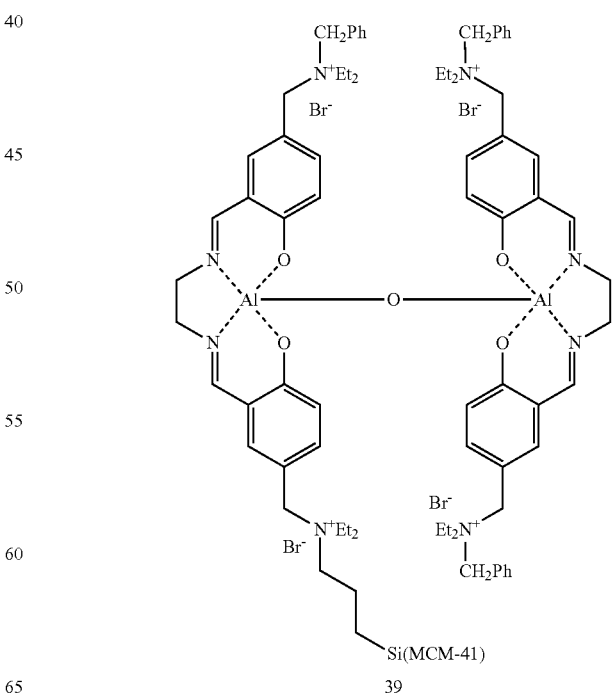

39

Tetrabutylammonium bromide (0.20 g, 0.6 mmol) and benzyl bromide (0.13 g, 1 mmol) were added to a suspension of supported aluminium complex (38) (200 mg, 0.15 mmol) in CH$_3$CN (30 mL) and the mixture was refluxed overnight. Then, the mixture was washed with EtOAc (4×50 mL) to leave MCM-41 supported complex (39) as a yellow powder (0.22 g, 98%). $\square_{max}$ 3452, 1634, 1052 and 947 cm$^{-1}$. ICPMS (5 mg of supported catalyst digested with 5 mL of 1M HCl) gave an aluminium concentration of 22.55 ppm, corresponding to a catalyst loading of 0.47 mmol per gram of support.

Example 11

Synthesis of Styrene Carbonate Using Supported Catalyst (39)

Styrene oxide (1.66 mmol), catalyst (39) (0.0415 mmol) and propylene carbonate (0.845 g) were placed in a sample vial fitted with a magnetic stirrer bar and placed in a large conical flask. The conical flask was placed in an oil bath thermostatted at 26° C. Cardice pellets were added to the conical flask which was fitted with a rubber stopper pierced by a deflated balloon. The reaction was stirred for 24 hours with samples being removed after 3, 6 and 24 hours for analysis by GC/MS to determine the conversion of epoxide to cyclic carbonate. The results were:

| Time (hours) | Conversion (%) |
|---|---|
| 3 | 12 |
| 6 | 23 |
| 24 | 57 |

Example 12

Synthesis of Ethylene Carbonate Using Supported Catalyst (39)

Catalyst (39) (0.0503 mmol) and propylene carbonate (1.0 g) were added to a reaction vial to which pre-cooled ethylene oxide (2.01 mmol) was added. The reaction vial was fitted with a magnetic stirrer and placed inside a stainless steel reaction vessel along with sufficient cardice pellets to pressurise the system to approximately 6 atmospheres. The stainless steel reactor was sealed and the reaction left to stir for 24 hours after which the reaction mixture was taken up in ethyl acetate and filtered to remove the catalyst. The ethyl acetate was evaporated under reduced pressure and the weight of the residue determined. The relative composition of propylene and ethylene carbonates was determined by GC/MS and used to calculate that a 93% conversion of ethylene oxide to ethylene carbonate had been achieved.

Example 13

(a) Synthesis of [Al(salen)]$_2$O$^+$Cl$^-$ Supported on solgel (40)

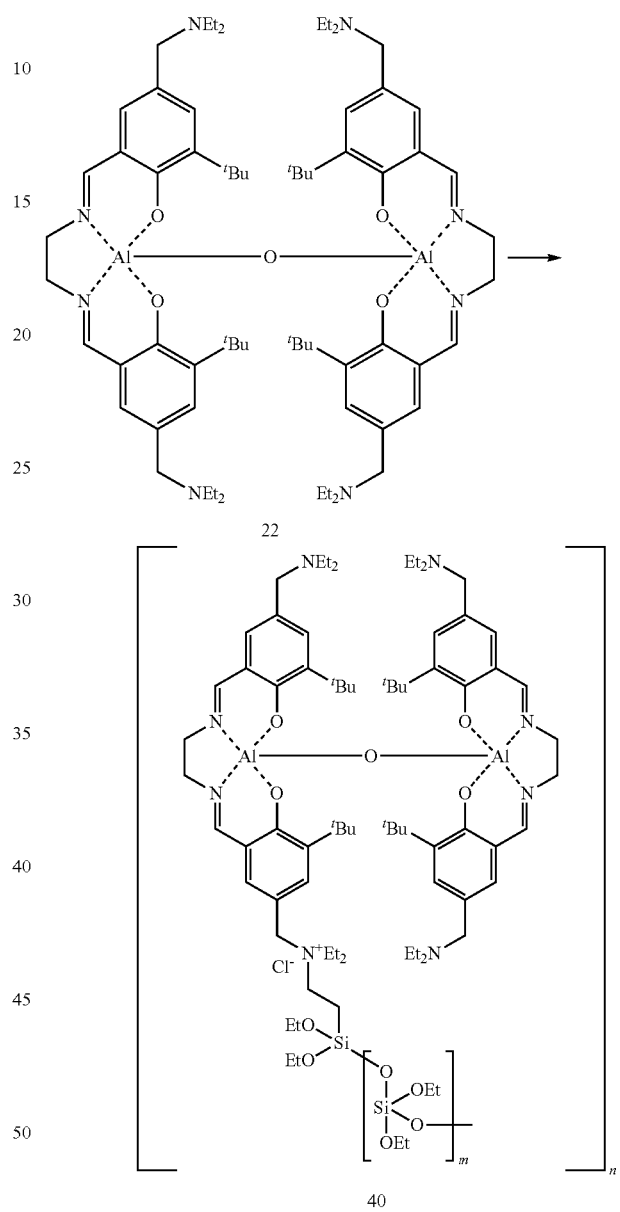

m is approximately 10

(3-Chloropropyl)-triethoxysilane (0.12 g, 0.5 mmol) was added to a solution of aluminium complex (22) (0.55 g, 0.5 mmol) in CH$_3$CN (40 mL) and the reaction was refluxed overnight. Then the solvent was removed to leave a product which was dissolved in EtOH (2 mL). Si(OEt)$_4$ (1.12 mL, 5 mmol) was added to this solution and the mixture stirred for 2 minutes at room temperature. Then, H$_2$O (3 mL) and NH$_4$OH (3 drops) were added and the mixture was vigorously stirred for 5 min. The mixture was left undisturbed for 5 days and then placed in an oven at 110° C. for further two days. The resulting solid was washed with isopropanol (2×25 mL) and CH₃CN (2×25 mL) and dried overnight at 110° C. to leave the solgel supported catalyst (40) (0.42 g, 41%). ☐$_{max}$ 2914, 1633 and 1067 cm⁻¹.

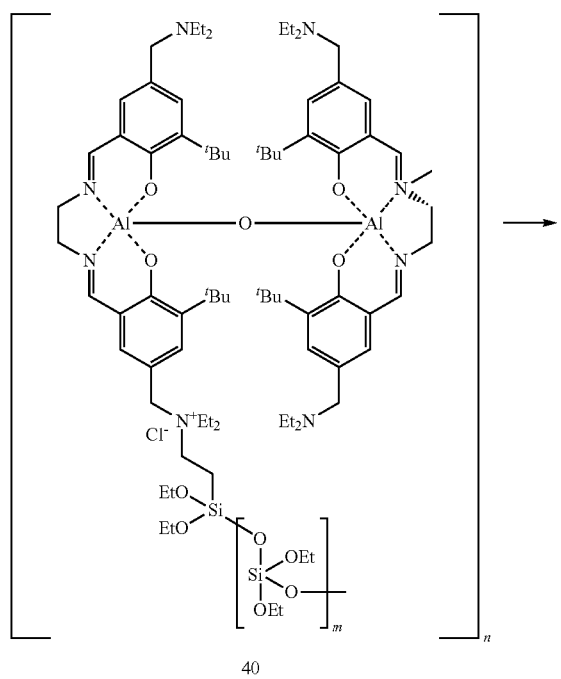

40

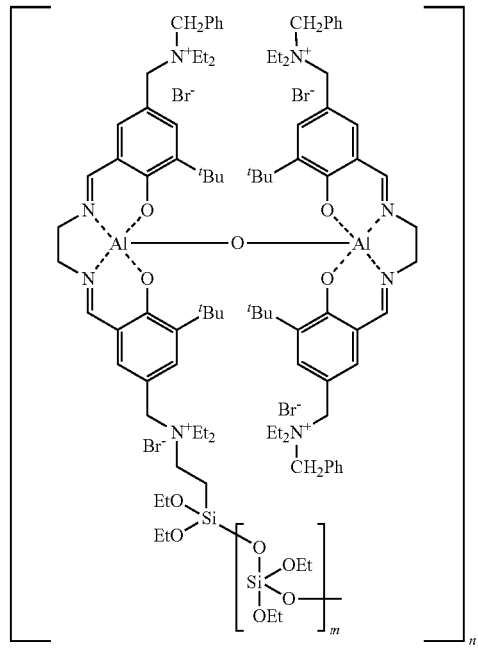

41 m is approximately 10

(b) Synthesis of Benzylated [Al(salen)]₂O⁺Br⁻ Supported on solgel (41)

Tetrabutylammonium bromide (0.20 g, 0.6 mmol) and benzylbromide (0.13 g, 1 mmol) were added to a suspension of supported aluminium complex (40) in CH₃CN (30 mL) and the mixture refluxed overnight. Then, the mixture was washed with EtOAc (4×50 mL) to leave solgel supported catalyst (41) as a yellow powder (0.52 g, 96%). ☐$_{max}$ 3562, 1629 and 1052 cm⁻¹. ICPMS (5 mg of supported catalyst digested with 10 mL of 1M HCl) gave an aluminium concentration of 13.65 ppm, corresponding to a catalyst loading of 0.51 mmol per gram of support.

Example 14

Synthesis of Styrene Carbonate Using Supported Catalyst (41)

Styrene oxide (1.66 mmol), catalyst (41) (0.0415 mmol) and propylene carbonate (0.845 g) were placed in a sample vial fitted with a magnetic stirrer bar and placed in a large conical flask. The conical flask was placed in an oil bath thermostatted at 26° C. Cardice pellets were added to the conical flask which was fitted with a rubber stopper pierced by a deflated balloon. The reaction was stirred for 24 hours with samples being removed after 3, 6 and 24 hours for analysis by GC/MS spectroscopy to determine the conversion of epoxide to cyclic carbonate. The results were:

| Time (hours) | Conversion (%) |
|---|---|
| 3 | 10 |
| 6 | 20 |
| 24 | 52 |

Example 15

Synthesis of Ethylene Carbonate Using Supported Catalysts (29), (35) and (41)

(a) Catalyst (41)(0.0503 mmol) and propylene carbonate (1.0 g) were added to a reaction vial to which pre-cooled ethylene oxide (2.01 mmol) was added. The reaction vial was fitted with a magnetic stirrer and placed inside a stainless steel reaction vessel along with sufficient cardice pellets to pressurise the system to approximately 6 atmospheres. The stainless steel reactor was sealed and the reaction left to stir for 24 hours after which the reaction mixture was taken up in ethyl acetate and filtered to remove the catalyst. The ethyl acetate was evaporated in vacuo and the weight of the residue determined. The relative composition of propylene and ethylene carbonates was determined by GC/MS and used to calculate that a 97% conversion of ethylene oxide to ethylene carbonate had been achieved.

(b) The above procedure was used but with catalyst (29) and resulted in 95% conversion of ethylene oxide to ethylene carbonate after a reaction time of 24 hours.

(c) The above procedure was used but with catalyst (35) and resulted in 81% conversion of ethylene oxide to ethylene carbonate after a reaction time of 24 hours.

Example 16

Use of Immobilised Catalysts to Convert Ethylene Oxide into Ethylene Carbonate Under Continuous Flow Conditions The flow reactor is illustrated in FIG. 1. Ethylene oxide was collected from a commercially supplied cylinder as a liquid in a cooled beaker at −78° C. and placed, with a magnetic stirrer bar, inside a 360 mL pre-cooled (−10 to −40° C.) stainless steel pressure vessel (3). The vessel was then sealed. Nitrogen and carbon dioxide gases were supplied from cylinders via mass flow controller units (1) and their respective lines merged to the inlet of the pressure vessel (see diagram). All tubing used in the system was composed of stainless steel with an internal diameter of approximately 1.6 mm. The temperature of the pressure vessel (3) was controlled by a cryostatically cooled bath (2) to provide the required rate of evaporation of ethylene oxide at a particular flow rate of $N_2$ and $CO_2$. This was determined by passing the vessel outlet line directly into a GC system (6) fitted with a column capable of separating the three gases. The vessel outlet line was then connected to a stainless steel tubular reactor (4)(15 cm×10 mm) packed with a solid supported catalyst and plugged at both ends with a small volume of cotton. The tubular reactor (4) was either kept at ambient temperature or immersed in a thermostatted water bath. The mixture of $CO_2$, ethylene oxide and $N_2$ was passed through the reactor column at a steady flow rate. The outlet of the reactor (4) was connected to a sealed glass vial (5) via a needle to collect any non-gaseous products. The outlet from the product receptacle passed to a GC system (6) which was used to determine the concentrations of $CO_2$, $N_2$ and ethylene oxide in the effluent gas stream. The results obtained with both silica and polystyrene supported catalysts are given in the following table.

| Run | Catalyst (amount g) | $N_2$ flow (mL/min) | $CO_2$ flow (mL/min) | Pressure vessel temperature (° C.) | Ethylene oxide consumption (mL/h) | Time (h) | Reactor temperature (° C.) | Ethylene carbonate yield |
|---|---|---|---|---|---|---|---|---|
| 1 | 29 (2.51) | 25  | 25  | −40 | 1.0  | 19  | ambient | 0.14 g, 0.15% |
| 2 | 35 (1.95) | 25  | 25  | −40 | 1.0  | 19  | ambient | 0.08 g, 0.1% |
| 3 | 35 (1.17) | 2.5 | 2.5 | −10 | 0.21 | 120 | ambient | 1.1 g, 1.5% |
| 4 | 35 (1.17) | 2.5 | 1.0 | −10 | 0.15 | 96  | ambient | 1.5 g, 4% |
| 5 | 35 (3.52) | 2.5 | 1.0 | −10 | 0.15 | 46  | ambient | 2.4 g, 21% |
| 6 | 35 (3.52) | 2.5 | 1.0 | −10 | 0.15 | 25  | 50 | 3.4 g, 53% |
| 7 | 35 (3.52) | 2.5 | 1.0 | −10 | 0.15 | 7   | 60 | 1.49 g, 80% |

What is claimed:

1. A process for the production of cyclic carbonates comprising contacting an epoxide with carbon dioxide in the presence of a dimeric aluminium(salen) catalyst of formula I:

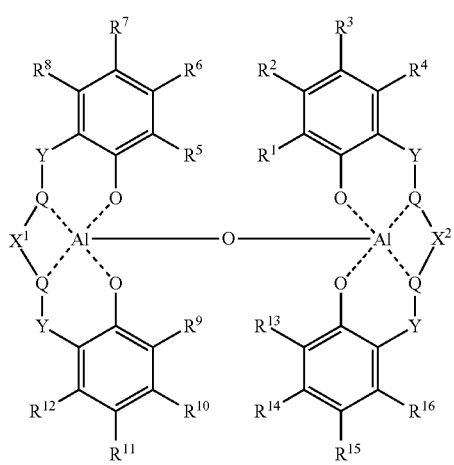

(I)

wherein:

Y-Q is $CR^{C1}$=N, where $R^{C1}$ is selected from H and optionally substituted $C_{1-4}$ alkyl;

each of the substituents $R^1$, $R^2$, $R^3$, $R^5$, $R^6$, $R^7$, $R^9$, $R^{10}$, $R^{11}$, $R^{13}$, $R^{14}$, and $R^{15}$, is independently selected from H, optionally substituted $C_{1-7}$ alkyl, L-A and L-A';

$R^4$=$R^8$=$R^{12}$=$R^{16}$=H;

L is a single bond or an unsubstituted $C_{1-3}$ alkylene group;

A is an ammonium group paired with a counterion selected from Cl, Br and I;

A' is an ammonium linking group bound to a solid support and paired with a counterion selected from Cl, Br and I;

$X^1$ and $X^2$ are independently (i) a $C_{2-5}$ alkylene chain; or (ii) a divalent group selected from $C_{5-7}$ cyclic alkylene;

provided that:

at least one of $R^1$, $R^2$, $R^3$, $R^5$, $R^6$, $R^7$, $R^9$, $R^{10}$, $R^{11}$, $R^{13}$, $R^{14}$, and $R^{15}$ is L-A'.

2. The process according to claim 1, carried out at a temperature of between 0 and 140° C. and/or a pressure of between 0.5 and 5 atm.

3. The process of claim 1, wherein the catalysed reaction is:

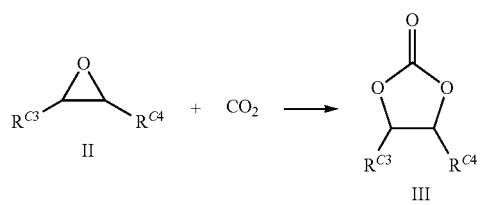

wherein $R^{C3}$ and $R^{C4}$ are independently selected from H, optionally substituted $C_{1-10}$ alkyl, optionally substituted $C_{3-20}$ heterocyclyl and optionally substituted $C_{5-20}$ aryl, or $R^{C3}$ and $R^{C4}$ form an optionally substituted linking group between the two carbon atoms to which they are respectively attached.

4. The process according to claim 3, wherein $R^{C4}$ is H.

5. The process according to claim 3, wherein $R^{C3}$ is selected from optionally substituted $C_{1-4}$ alkyl and optionally substituted $C_{5-7}$ aryl.

6. The process according to claim 1, carried out in a flow reactor or a gas flow reactor.

7. The process according to claim 1, carried out under continuous flow conditions.

8. The process according to claim 1, carried out under solvent-free conditions or using propylene carbonate as a solvent, and/or wherein one of $R^1$, $R^2$, $R^3$, $R^5$, $R^6$, $R^7$, $R^9$, $R^{10}$, $R^{11}$, $R^{13}$, $R^{14}$, and $R^{15}$ is selected from L-A' and A' is selected from —NH(CH$_3$)(CH$_2$)—, —NH(CH(CH$_3$)$_2$)(C(CH$_3$)$_2$)—, —N(CH$_3$)$_2$(CH$_2$)—, —N(CH$_2$CH$_3$)$_2$(CH$_2$CH$_2$)—, —N(CH$_2$CH$_3$)$_2$CH$_2$—, —N(CH$_2$CH$_3$)$_2$(CH$_2$CH$_2$CH$_2$)—, and —NHPh(CH$_2$)—.

9. The process according to claim 1, wherein L is an unsubstituted $C_{1-3}$ alkylene group.

10. The process according to claim 1, wherein $X^1$ and $X^2$ are independently selected from —(CH$_2$)$_n$— and n is 2 or 3 or wherein $X^1$ and $X^2$ independently represent $C_6$ cyclic alkylene or wherein $X^1$ and $X^2$ independently represent a divalent group selected from $C_{5-7}$ cyclic alkylene and is unsubstituted or wherein $X^1$ and $X^2$ are both —C$_2$H$_4$—.

11. The process according to claim 1, wherein the ammonium counter group is Br$^-$.

12. The process according to claim 1, wherein the ammonium group A is chosen from —N(CH$_2$CH$_3$)$_3$ and —N(CH$_2$CH$_3$)$_2$(CH$_2$Ph) or wherein the solid support is optionally a silica support.

13. The process according to claim 1, wherein $X^1$=$X^2$=$C_2$ alkylene or $C_6$ cyclic alkylene.

14. The process according to claim 1, wherein $C_{1-7}$ alkyl is butyl.

15. The process according to claim 1, wherein $R^{C1}$ is H.

* * * * *

UNITED STATES PATENT AND TRADEMARK OFFICE
CERTIFICATE OF CORRECTION

| | |
|---|---|
| PATENT NO. | : 9,273,024 B2 |
| APPLICATION NO. | : 13/887787 |
| DATED | : March 1, 2016 |
| INVENTOR(S) | : Michael North |

It is certified that error appears in the above-identified patent and that said Letters Patent is hereby corrected as shown below:

In the Specification

Column 21, In line 12, after "step." no new paragraph

Column 21, In line 21, after ".4795" replace "." with --,--

Column 22, In line 65, after "(30)." no new paragraph

Signed and Sealed this
Second Day of August, 2016

Michelle K. Lee
*Director of the United States Patent and Trademark Office*

Column 29, lines 32 to 54, should read:
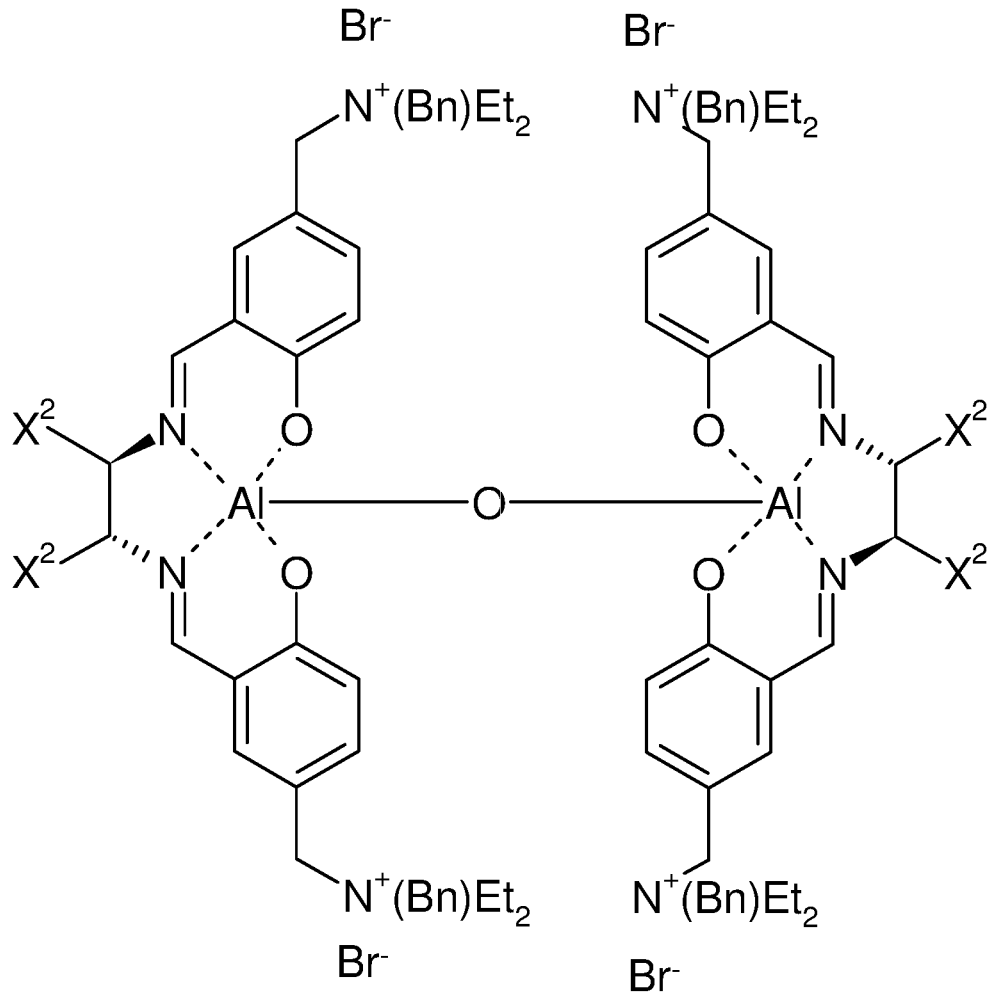
25: $X^2$ = $(CH_2)_4$
26: $X^2$ = H